(12) United States Patent
Rosenwald et al.

(10) Patent No.: US 9,133,522 B2
(45) Date of Patent: Sep. 15, 2015

(54) COMPOSITIONS AND METHODS FOR THE DIAGNOSIS AND PROGNOSIS OF MESOTHELIOMA

(75) Inventors: Shai Rosenwald, Nes Ziona (IL); Hila Benjamin, Kiryat Uno (IL); Nitzan Rosenfeld, Rehovot (IL)

(73) Assignee: Rosetta Genomics Ltd., Rehovot (IL)

( * ) Notice: Subject to any disclaimer, the term of this patent is extended or adjusted under 35 U.S.C. 154(b) by 580 days.

(21) Appl. No.: 12/740,256

(22) PCT Filed: Oct. 29, 2008

(86) PCT No.: PCT/IL2008/001428
§ 371 (c)(1),
(2), (4) Date: Apr. 28, 2010

(87) PCT Pub. No.: WO2009/057113
PCT Pub. Date: May 7, 2009

(65) Prior Publication Data
US 2010/0323903 A1    Dec. 23, 2010

Related U.S. Application Data

(60) Provisional application No. 60/983,944, filed on Oct. 31, 2007, provisional application No. 61/083,181, filed on Jul. 24, 2008.

(51) Int. Cl.
*C12Q 1/68* (2006.01)

(52) U.S. Cl.
CPC .............. *C12Q 1/6886* (2013.01); *C12Q 1/68* (2013.01); *C12Q 2600/112* (2013.01); *C12Q 2600/178* (2013.01)

(58) Field of Classification Search
CPC .......................................................... C12Q 1/68
USPC ........................................................ 435/6.1
See application file for complete search history.

(56) References Cited

U.S. PATENT DOCUMENTS

| | | | |
|---|---|---|---|
| 2005/0014190 A1* | 1/2005 | Blumenfeld et al. | 435/6 |
| 2005/0107325 A1 | 5/2005 | Manoharan et al. | |
| 2005/0182005 A1 | 8/2005 | Tuschl et al. | |

FOREIGN PATENT DOCUMENTS

| | | |
|---|---|---|
| WO | WO 93/23569 | 11/1993 |
| WO | WO 94/02595 | 2/1994 |
| WO | WO 99/04819 | 2/1999 |
| WO | WO 99/05094 | 2/1999 |
| WO | WO 2005/078139 A2 | 8/2005 |
| WO | WO 2006/069584 A2 | 7/2006 |

OTHER PUBLICATIONS

Yamihara et al. Cancer Cell (2006) 9: 189-198.*
Pritchard et al. Cancer Prevention Research (2012) 5(3): 492-497.*
Ferracin et al. Journal of Pathology (2011) 225: 43-53.*
Gee et al. International Journal of Cancer (2010) 127: 2859-2869.*
Trupiano et al. Modern Pathology (2004) 17: 476-481.*
Jean et al. American Journal of Pathology (2011) 178: 881-894.*
U.S. Appl. No. 11/429,720, filed May 8, 2009, Bentwich, et al.
U.S. Appl. No. 11/418,870, filed May 4, 2006, Bentwich, et al.
U.S. Appl. No. 11/384,049, filed Mar. 17, 2006, Bentwich et al.
Bartel et al.,"MicroRNAs: At the Root of Plant Development," Plant Physiology, (2003), pp. 709-717, vol. 132.
Brennecke et al., "Principles of MicroRNA—Target Recognition," PLoS Biology, (2005), pp. 0001-0015, vol. 3, No. 3.
Calin et al., "A MicroRNA Signature Associated with Prognosis and Progression in Chronic Lymphocytic Leukemia," The New England Journal of Medicine, (2005), pp. 1793-1801, vol. 353, No. 17.
Doench et al., "Specificity of microRNA target selection in translational repression," Genes & Development, (2004), pp. 1-8.
Hofacker et al., "Fast Folding and Comparison of RNA Secondary Structures," Monatshefte für Chemie (Chemical Monthly), (1994), pp. 167-188, vol. 125.
Krek et al., "Combinatorial microRNA target predictions," Nature Genetics, (2005), pp. 1-6.
Krutzfeldt et al., "Silencing of microRNAs in vivo with 'antagomirs'," Nature, (2005), pp. 1-5.
Lewis et al., "Conserved Seed Pairing, Often Flanked by Adenosines, Indicates that Thousands of Human Genes are MicroRNA Targets," Cell, (2005), pp. 15-20, vol. 120.
McManus. M. T., "MicroRNAs and cancer," Seminars in Cancer Biology, (2003), pp. 253-258, vol. 13, [XP-002358494].
Soutschek et al., "Therapeutic silencing of an endogenous gene by systemic administration of modified siRNAs," Nature, (2004), pp. 173-178, vol. 432.
Thomson et al., "A custom microarray platform for analysis of microRNA gene expression," Nature Methods, (2004), pp. 1-7, vol. 1, No. 1.
Yekta et al., "MicroRNA-Directed Cleavage of *HOXB8* mRNA," Science, (2004), pp. 594-596, vol. 304.
"Sequence 220 from Patent EP1627925," [XP002513324], (2006), p. 1.
"Sequence 1352 from Patent EP1777301," [XP002513325], (2007), p. 1.
"Human probe for miRNA No. 194," [XP002513329], (2006), pp. 1-2.
"Human microRNA (miRNA) mir-192," [XP002513330], (2005), pp. 1-2.
Partial Search Report received in the corresponding International Patent Application No. PCT/IL2008/001428, dated Feb. 25, 2009.

* cited by examiner

*Primary Examiner* — Ardin Marschel
(74) *Attorney, Agent, or Firm* — Ron Galant; Polsinelli PC

(57) ABSTRACT

The present invention provides nucleic acid sequences that are used for identification and diagnosis of specific cancers. The nucleic acid sequences can also be used for prognosis evaluation of a subject based on the expression profile of a biological sample.

7 Claims, 24 Drawing Sheets

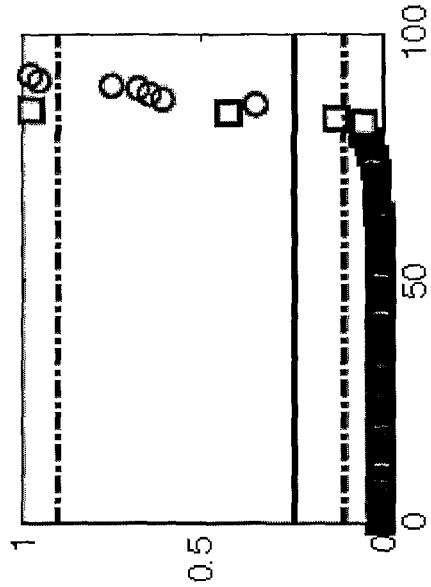
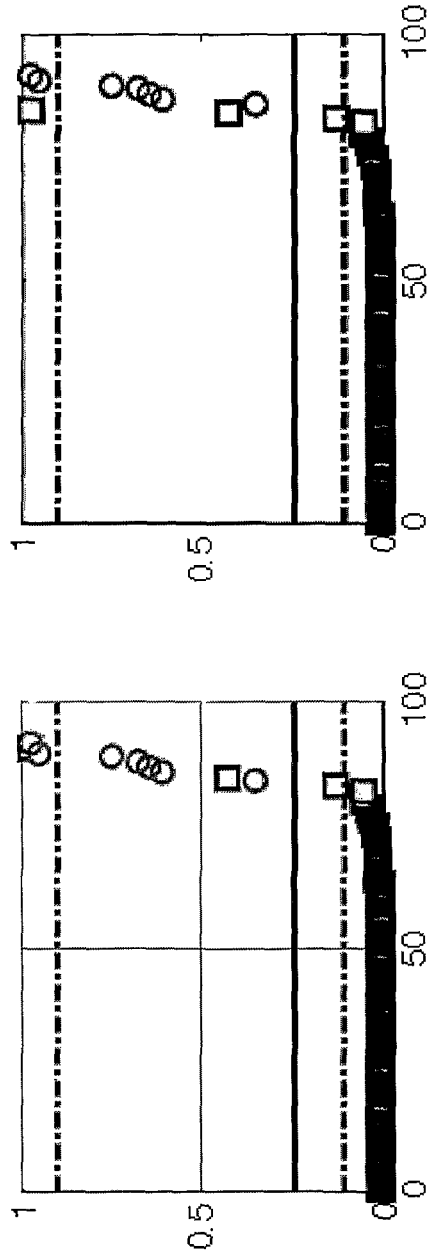
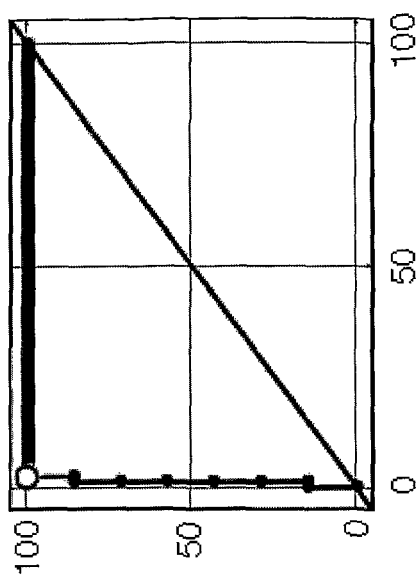
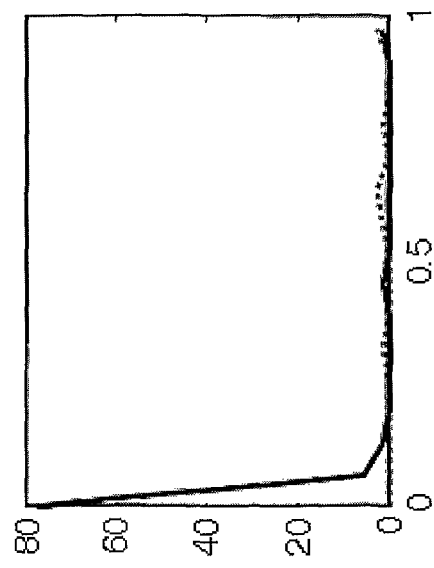

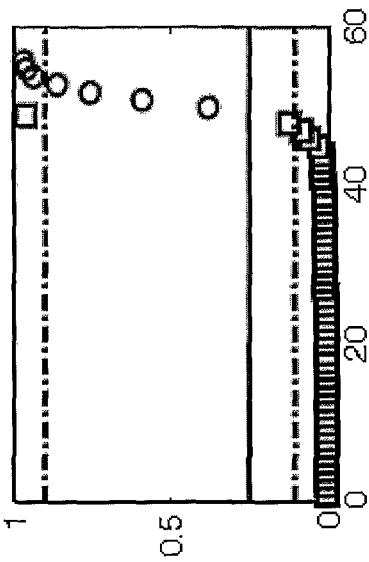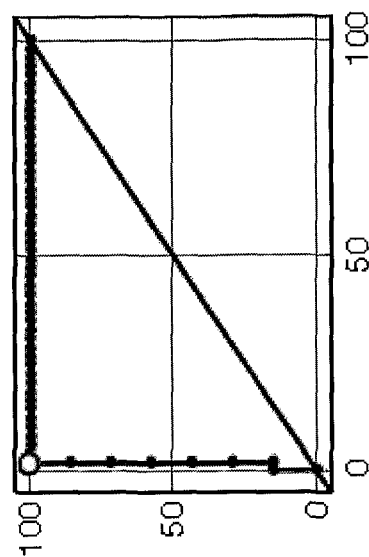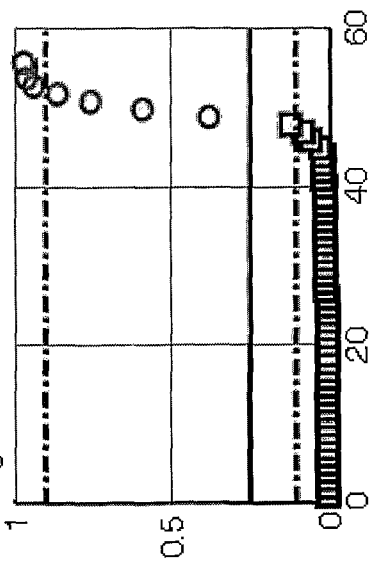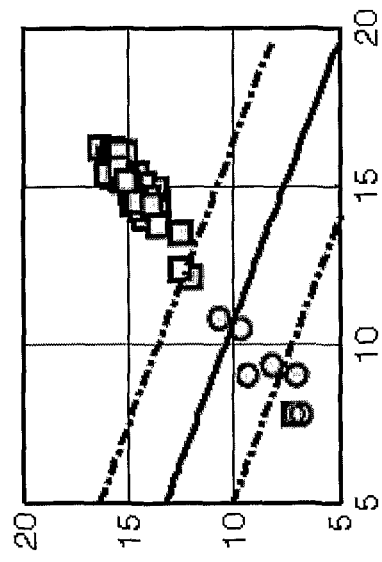

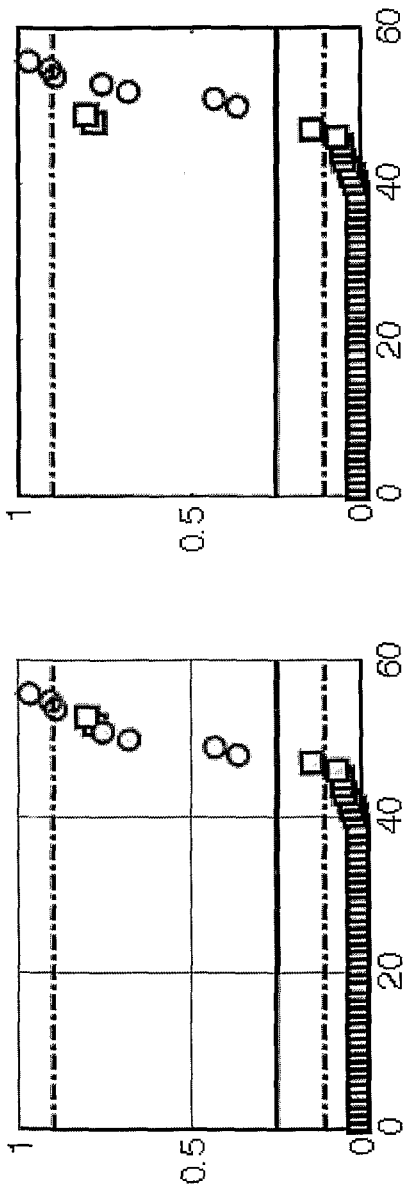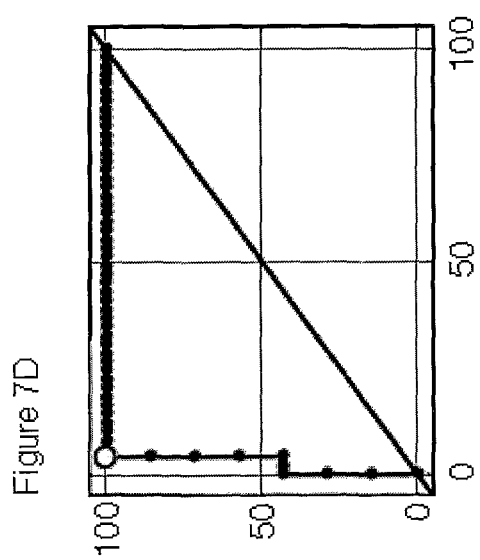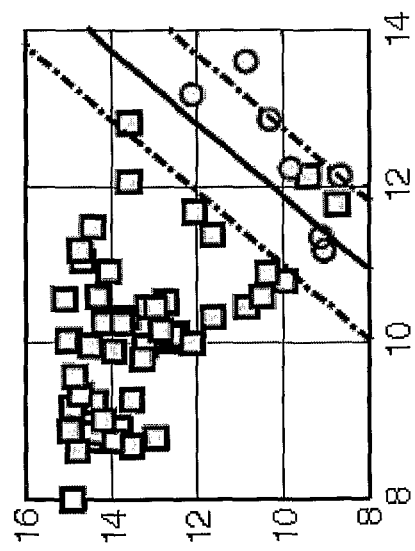
Figure 7A Figure 7B Figure 7C Figure 7D

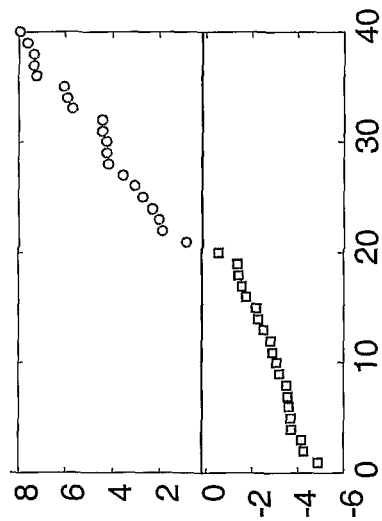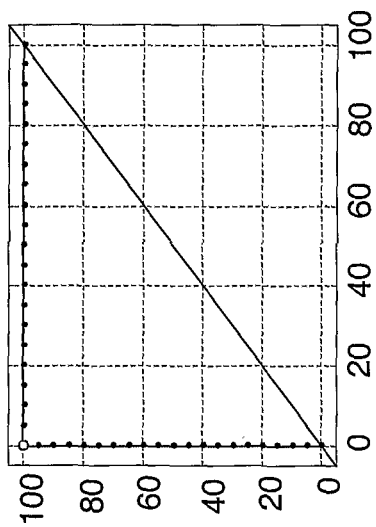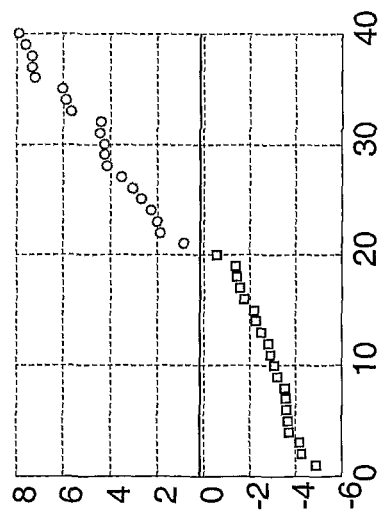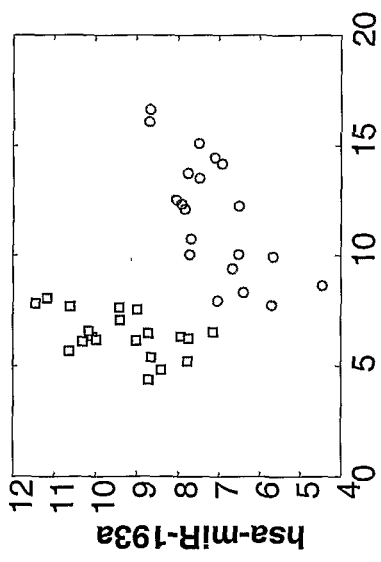
Figure 8A
Figure 8B
Figure 8C
Figure 8D

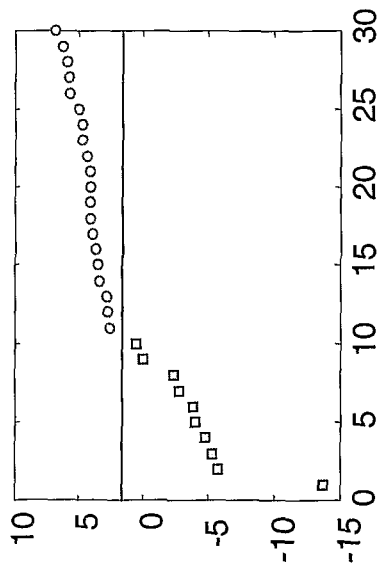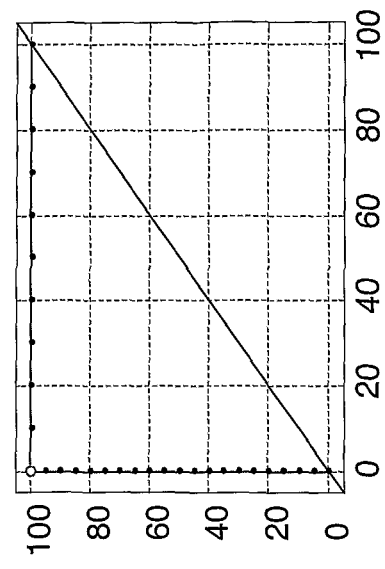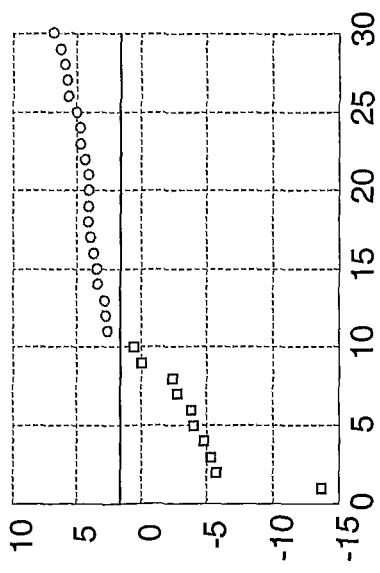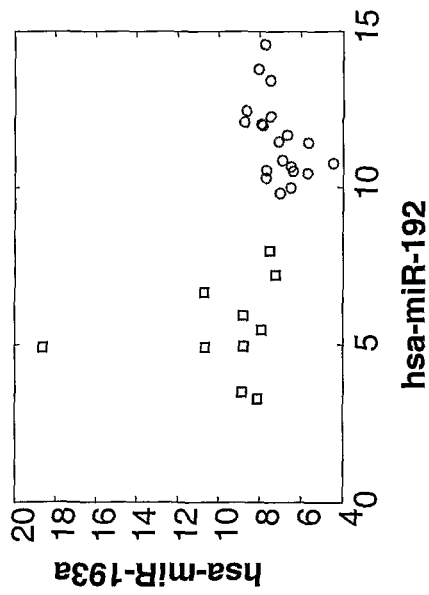
Figure 10A
Figure 10B
Figure 10C
Figure 10D

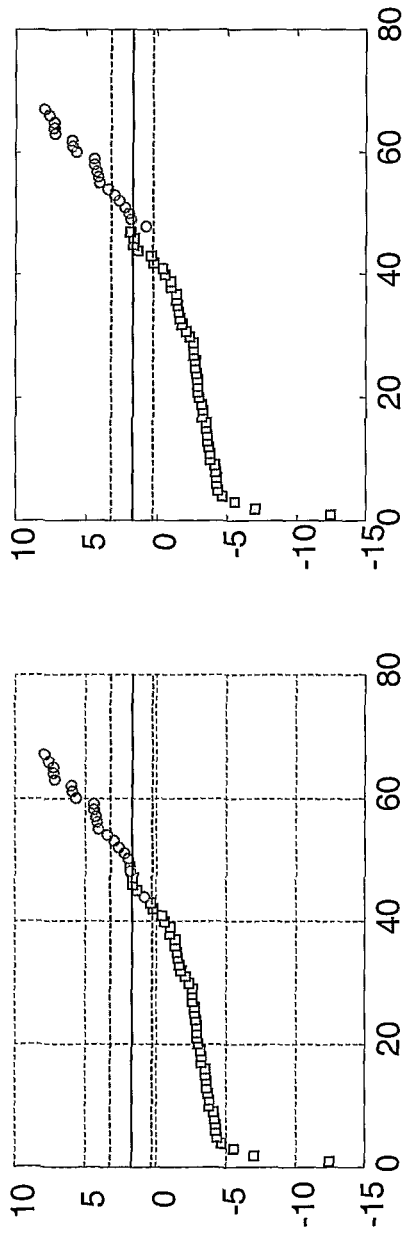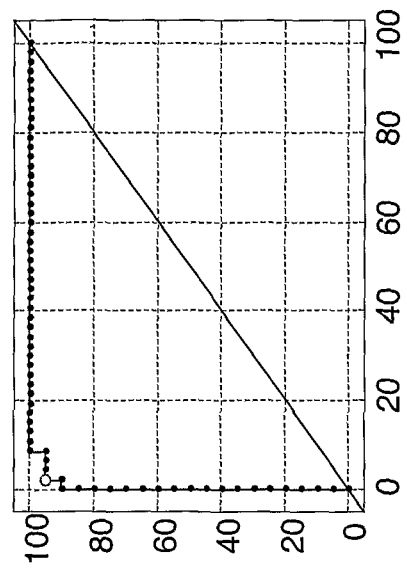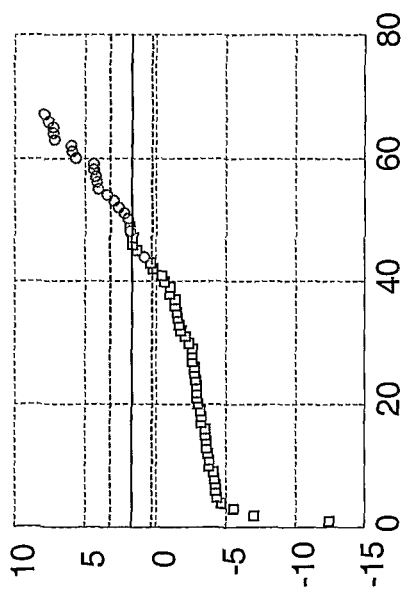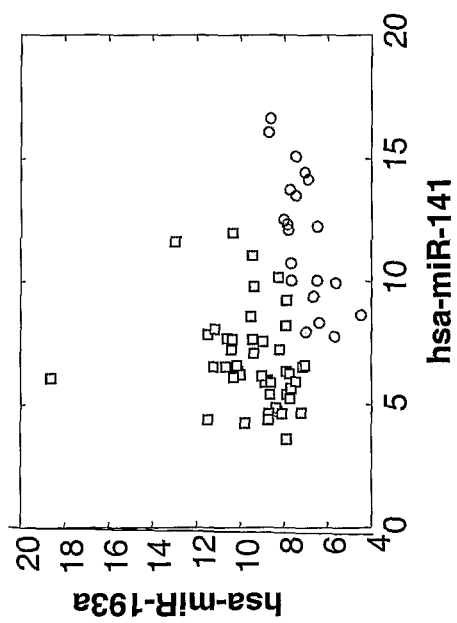
Figure 17A
Figure 17B
Figure 17C
Figure 17D

COMPOSITIONS AND METHODS FOR THE DIAGNOSIS AND PROGNOSIS OF MESOTHELIOMA

CROSS-REFERENCE TO RELATED PATENT APPLICATIONS

This application is the U.S. National Phase of PCT/IL2008/001428, filed Oct. 29, 2008, which claims priority from U.S. Provisional Application No. 60/983,944, filed Oct. 31, 2007 and 60/083,181, filed Jul. 24, 2008, all of which are incorporated herein by reference in entirety.

FIELD OF THE INVENTION

The invention relates in general to microRNA molecules associated with specific types of cancers, as well as various nucleic acid molecules relating thereto or derived therefrom.

BACKGROUND OF THE INVENTION

In recent years, microRNAs (miRs, miRNAs) have emerged as an important novel class of regulatory RNA, which has profound impact on a wide array of biological processes. These small (typically 18-24 nucleotides long) non-coding RNA molecules can modulate protein expression patterns by promoting RNA degradation, inhibiting mRNA translation, and also affecting gene transcription. miRs play pivotal roles in diverse processes such as development and differentiation, control of cell proliferation, stress response and metabolism. There are currently about 850 known human miRs. The expression of many miRs was found to be altered in numerous types of human cancer, and in some cases strong evidence has been put forward in support of the conjecture that such alterations may play a causative role in tumor progression. MicroRNA expression is highly tissue specific and informative for identification of tumor tissue origin.

Mesothelioma is a tumor that occurs in the mesothelium that covers the surface of the pleura, pericardium and peritoneum that respectively envelop the organs of the chest cavity such as the lungs and heart, and abdominal organs such as the digestive tract and liver. In the case of diffuse pleural mesothelioma, chest pain is caused by invasion of the intercostal nerves on the side of the chest wall pleura, and respiratory and circulatory disorders may occur due to tumor growth and accumulation of pleural fluid in the pleura on the organ side. There is eventually proliferation into the adjacent mediastinal organs, progressing to direct invasion of the heart or development into the abdominal cavity by means of the diaphragm, or there may be development outside the chest cavity as a result of additional lymphatic or circulatory metastasis.

Numerous different classifications of the clinical disease stages have been used for mesothelioma, and since the methods for classifying the disease stage used differ, previous therapeutic reports on mesothelioma have encountered difficulties when comparing the results of treatment (Nakano, Respiration, Vol. 18, No. 9, pp. 916-925, 1999). In addition, malignant mesothelioma has a causative relationship with exposure to asbestos, and this has also been demonstrated in animal experiments (Tada, Journal of Clinical and Experimental Medicine (March Supplement), "Respiratory Diseases", pp. 406-408, 1999). Asbestos that has been inhaled into the respiratory tract reaches a location directly beneath the pleura where a tumor eventually develops due to chronic irritation for at least about 20 years, and this tumor spreads in a thin layer over the entire surface of the pleura. Consequently, although malignant mesothelioma is classified as an asbestos-related disease, not all malignant mesothelioma is caused by asbestos, and well-documented exposure is only observed in about half of all patients. Malignant pleural mesothelioma is resistant to treatment, associated with an extremely poor prognosis, and requires that countermeasures be taken immediately (Nakano, Respiration, Vol. 18, No. 9, pp. 916-925, 1999).

The prognosis for malignant mesothelioma is influenced by the stage of the disease. Surgery, as well as adjuvant immunological treatments (e.g., interferon or interleukin) can be effective treatment, but only in the rare event of an early stage diagnosis.

When dealing with the possibility of a mesothelioma in the pleura or the peritoneum few differential indications should be considered. Both the pleura and the peritoneum can have secondary malignancies with primaries at different rates, hence differentiation between mesothelioma and secondary malignancy or another primary from different source is important. Pathological diagnosis can have significant interobserver variability, and in the absence of specific markers mesothelioma is difficult to identify from other epithelial cancers.

Lung cancer is one of the most common cancers and has become a predominant cause of cancer-related death throughout the world. Scientists strive to explore biomarkers and their possible role in the diagnosis, treatment and prognosis of specific lung cancers.

Making the correct diagnosis and specifically the distinction between lung squamous carcinoma and other Non Small Cell Lung Carcinoma (NSCLC) such as but not limited to lung adenocarcinoma, has practical importance for choice of therapy. Severe or fatal hemorrhage is a black box warning for lung squamous carcinoma patients undergoing bevacizumab (Avastin) therapy. To-date there is no objective standardized test for differentiating squamous from non squamous NSCLC.

The search for biomarkers for the early detection and accurate diagnosis of various NSCLC has met with little success. Much emphasis has been placed on the discovery and characterization of a unique tumor marker. However, no marker has been identified that has adequate sensitivity or specificity to be clinically useful, although a combination of multiple markers has been shown to increase diagnostic accuracy.

There is an unmet need for specific and accurate markers associated with specific types of cancers.

SUMMARY OF THE INVENTION

The present invention provides specific nucleic acid sequences that are used for the identification, classification and diagnosis of various cancers.

The invention provides a method of classifying a specific cancer comprising obtaining a biological sample from a subject determining an expression profile of a nucleic acid sequence selected from the group consisting of SEQ ID NOS: 2, 10, 11, 24, 41, 1, 3-9, 12-23, 25, 26, 44-50, 55, and 58-87 a fragment thereof or a sequence having at least about 80% identity thereto from said sample; and comparing said expression profile to a reference expression profile, wherein the results of said comparison allows for classification of said specific cancer.

The invention further provides a method of diagnosing mesothelioma comprising obtaining a biological sample from a subject, determining an expression profile of a nucleic acid sequence selected from the group consisting of SEQ ID NOS: 2, 10, 11, 24, 41, 1, 3-9, 12-23, 25, 26 and 58-72, a fragment thereof and a sequence having at least about 80% identity thereto from said sample; and comparing said expression profile to a reference expression profile, wherein the comparison of said determined expression profile to said reference expression profile allows for the diagnosis of mesothelioma.

The invention also provides a method to distinguish between mesothelioma and other cancers, the method comprising obtaining a biological sample from a subject, determining an expression profile of a nucleic acid sequence selected from the group consisting of SEQ ID NOs: 2, 10, 11, 24, 41, 1, 3-9, 12-23, 25, 26 and 58-72, a fragment thereof and a sequence having at least about 80% identity thereto in said sample, and comparing said expression profile to a reference expression profile, wherein the comparison of said determined expression profile to a reference expression profile is indicative of one of mesothelioma and said other cancers.

According to some embodiments the mesothelioma is pleural mesothelioma. According to some embodiments the mesothelioma is mesothelioma of the peritoneum.

According to some embodiments the other cancer is adenocarcinoma. The adenocarcinoma may be an adenocarcinoma of an organ selected from the group consisting of lung, stomach, kidney, colon, prostate, cervix, esophagus, pancreas, small intestine and breast. According to some embodiments the other cancer originates from an organ selected from the group consisting of colon, kidney, liver, pancreas and stomach. The cancer originating from the kidney, may be renal cell carcinoma, and the cancer originating from the liver, may be hepatocellular carcinoma.

According to some embodiments the nucleic acid sequence is selected from the group consisting of SEQ ID NOs: 2, 10, 11, 24 and 41, a fragment thereof and a sequence having at least about 80% identity thereto. According to other embodiments the nucleic acid sequence is selected from the group consisting of SEQ ID NOs: 2, 10, 11 and 41, a fragment thereof and a sequence having at least about 80% identity thereto. According to other embodiments the nucleic acid sequence is selected from the group consisting of SEQ ID NOs: 2, 10, 24 and 41, a fragment thereof and a sequence having at least about 80% identity thereto.

According to additional embodiments the other cancer is adenocarcinoma, the nucleic acid sequence is selected from the group consisting of SEQ ID NOs: 1-22, a fragment thereof and a sequence having at least about 80% identity thereto, and relatively high expression levels of any of SEQ ID NOs: 1, 2, 4-9, 11-14 and 16-22, a fragment thereof and a sequence having at least about 80% identity thereto, as compared to said reference expression profile, is indicative of adenocarcinoma. According to other embodiments the other cancer is adenocarcinoma, the nucleic acid sequence is selected from the group consisting of SEQ ID NOs: 1-22, a fragment thereof and a sequence having at least about 80% identity thereto, and relatively low expression levels of any of SEQ ID NOs: 3, 10 and 15, a fragment thereof and a sequence having at least about 80% identity thereto, as compared to said reference expression profile, is indicative of adenocarcinoma.

According to some embodiments the other cancer is a cancer originated from an organ selected from the group consisting of colon, kidney, liver, pancreas and stomach, the nucleic acid sequence is selected from the group consisting of SEQ ID NOs: 1-7, 9-20 and 22, a fragment thereof and a sequence having at least about 80% identity thereto, and relatively high expression levels of any of SEQ ID NOs: 1, 2, 4-7, 11-14 and 16-20, a fragment thereof and a sequence having at least about 80% identity thereto, as compared to said reference expression profile, is indicative of a cancer originated from an organ selected from the group consisting of colon, kidney, liver, pancreas and stomach. According to some embodiments the nucleic acid sequence is selected from the group consisting of SEQ ID NOs: 1-7, 9-20 and 22, a fragment thereof and a sequence having at least about 80% identity thereto, and relatively low expression levels of any of SEQ ID NOs: 3, 10 and 15, a fragment thereof and a sequence having at least about 80% identity thereto, as compared to said reference expression profile, is indicative of a cancer originated from an organ selected from the group consisting of colon, kidney, liver, pancreas and stomach.

According to some embodiments the other cancer is lung cancer, the nucleic acid sequence is selected from the group consisting of SEQ ID NOs: 1,3, 5-13, 15 and 18-22, a fragment thereof and a sequence having at least about 80% identity thereto, and relatively high expression levels of any of SEQ ID NOs: 1, 5-9, 11-14 and 18-22, a fragment thereof and a sequence having at least about 80% identity thereto, as compared to said reference expression profile, is indicative of lung cancer. According to other embodiments the other cancer is lung cancer, the nucleic acid sequence is selected from the group consisting of SEQ ID NOs: 1, 3, 5-13, 15 and 18-22, a fragment thereof and a sequence having at least about 80% identity thereto, and relatively low expression levels of any of SEQ ID NOs: 3, 10 and 15, a fragment thereof and a sequence having at least about 80% identity thereto, as compared to said reference expression profile, is indicative of lung cancer. The lung cancer may be selected from the group consisting of lung squamous cell carcinoma, lung undifferentiated small cell carcinoma, lung undifferentiated large cell carcinoma, lung adenocarcinoma, nonsmall-cell lung cancer (NSCLC), lung carcinoid and neuroendocrine-large cell carcinoma.

According to some embodiments the other cancer is liver cancer, the nucleic acid sequence is selected from the group consisting of SEQ ID NOs: 2, 14 and 23-25, a fragment thereof and a sequence having at least about 80% identity thereto, and relatively high expression levels of any of said nucleic acid sequence, as compared to said reference expression profile, is indicative of liver cancer.

According to some embodiments the biological sample is selected from the group consisting of bodily fluid, a cell line and a tissue sample. According to additional embodiments the tissue is a fresh, frozen, fixed, wax-embedded or formalin fixed paraffin-embedded (FFPE) tissue. According to some embodiments the biological sample is obtained from a subject with cancer of unknown primary (CUP), with a primary cancer or with a metastatic cancer. According to additional embodiments the method further comprises a classifier algorithm. The classifier may be selected from the group consisting of decision tree classifier, logistic regression classifier, nearest neighbor classifier, neural network classifier, Gaussian mixture model (GMM) and Support Vector Machine (SVM) classifier.

According to some embodiments the nucleic acid sequence expression profile is determined by a method selected from the group consisting of nucleic acid hybridization and nucleic acid amplification. According to some embodiments the nucleic acid hybridization is performed using a solid-phase nucleic acid biochip array or in situ hybridization.

According to some embodiments the nucleic acid amplification method is real-time PCR. The real-time PCR method may comprise forward and reverse primers. According to some embodiments the forward primer comprises a sequence selected from the group consisting of SEQ ID NOs: 27, 29, 31, 33, 35, 37 and 39 and a sequence at least about 80% identical thereto. According to additional embodiments the real-time PCR method further comprises a probe. According to some embodiments the probe comprises a sequence selected from the group consisting of a sequence that is complementary to a sequence selected from SEQ ID NOs: 1, 2, 10, 11, 23, 24 and 41, a fragment thereof and a sequence having at least about 80% identity thereto. According to additional embodiments the probe comprises a sequence selected from the group consisting of SEQ ID NOs: 28, 30, 32, 34, 36, 38, 40 and 43, a fragment thereof and a sequence having at least about 80% identity thereto.

An additional aspect provided by the invention is a kit for distinguishing between mesothelioma and other cancers, the kit comprising a probe comprising a sequence selected from the group consisting of a sequence that is complementary to a sequence selected from SEQ ID NOs: 1, 2, 10, 11, 23, 24, and 41, a fragment thereof and a sequence having at least about 80% identity thereto. According to another embodiment the probe comprises a sequence selected from the group consisting of SEQ ID NOs: 28, 30, 32, 34, 36, 38, 40 and 43, a fragment thereof and a sequence having at least about 80% identity thereto. In some embodiments the other cancer is adenocarcinoma. In other embodiments the other cancer originates from an organ selected from the group consisting of colon, kidney, liver, pancreas stomach and lung.

The invention further provides a method to distinguish between squamous Non Small Cell Lung Carcinoma (NSCLC) and non-squamous NSCLC comprising, the method comprising obtaining a biological sample from a subject, determining an expression profile of a nucleic acid sequence selected from the group consisting of SEQ ID NOs: 8, 21, 25, 44-50 and 55, a fragment thereof and a sequence having at least about 80% identity thereto in said sample, and comparing said expression profile to a reference expression profile, wherein comparison of said determined expression profile to a reference expression profile is indicative of one of squamous NSCLC and non-squamous NSCLC.

According to some embodiments a relatively high expression level of any of SEQ ID NOs: 8 and 21, a fragment thereof and a sequence having at least about 80% identity thereto, as compared to said reference expression profile, is indicative of non-squamous NSCLC. According to other embodiments a relatively low expression level of any of SEQ ID NOs: 49-50, a fragment thereof and a sequence having at least about 80% identity thereto, as compared to said reference expression profile, is indicative of non-squamous NSCLC.

According to some embodiments the non-squamous NSCLC is adenocarcinoma, and relatively high expression levels of any of SEQ ID NOs: 8, 21, 25, 44-48, a fragment thereof and a sequence having at least about 80% identity thereto, as compared to said reference expression profile, is indicative of adenocarcinoma. According to other embodiments the non-squamous NSCLC is adenocarcinoma, and relatively high expression levels of any of SEQ ID NOs: 49-50, a fragment thereof and a sequence having at least about 80% identity thereto, as compared to said reference expression profile, is indicative of squamous NSCLC. The adenocarcinoma may be an adenocarcinoma of an organ selected from the group consisting of lung, stomach, kidney, colon, prostate, cervix, esophagus, pancreas, small intestine and breast.

According to some embodiments the biological sample is selected from the group consisting of bodily fluid, a cell line and a tissue sample. According to additional embodiments the tissue is a fresh, frozen, fixed, wax-embedded or formalin fixed paraffin-embedded (FFPE) tissue. According to some embodiments the biological sample is obtained from a subject with cancer of unknown primary (CUP), with a primary cancer or with a metastatic cancer. According to additional embodiments the method further comprises a classifier algorithm. The classifier may be selected from the group consisting of decision tree classifier, logistic regression classifier, nearest neighbor classifier, neural network classifier, Gaussian mixture model (GMM) and Support Vector Machine (SVM) classifier.

According to some embodiments the nucleic acid sequence expression profile is determined by a method selected from the group consisting of nucleic acid hybridization and nucleic acid amplification. According to some embodiments the nucleic acid hybridization is performed using a solid-phase nucleic acid biochip array or in situ hybridization.

According to some embodiments the nucleic acid amplification method is real-time PCR. The real-time PCR method may comprise forward and reverse primers. According to some embodiments the forward primer comprises a sequence selected from the group consisting of SEQ ID NOS: 39, 51, 53 and 56 and a sequence at least about 80% identical thereto.

According to some embodiments the real-time PCR method further comprises a probe. According to additional embodiments the probe comprises a sequence selected from the group consisting of a sequence that is complementary to a sequence selected from SEQ ID NOs: 8, 41, 49, 55, a fragment thereof and a sequence having at least about 80% identity thereto. According to additional embodiments the probe comprises a sequence selected from the group consisting of SEQ ID NOs: 40, 52, 54 and 57, a fragment thereof and a sequence having at least about 80% identity thereto.

An additional aspect provided is a kit for distinguishing between squamous NSCLC and non-squamous NSCLC, the kit comprising a probe comprising a sequence selected from the group consisting of a sequence that is complementary to a sequence selected from SEQ ID NOs: 8, 41, 49, 55, a fragment thereof and a sequence having at least about 80% identity thereto. According to another embodiment the kit comprises a probe comprising a sequence selected from the group consisting of SEQ ID NOs: 40, 52, 54 and 57, a fragment thereof and a sequence having at least about 80% identity thereto.

These and other embodiments of the present invention will become apparent in conjunction with the figures, description and claims that follow.

BRIEF DESCRIPTION OF THE DRAWINGS

FIG. 2 demonstrates an exemplified classifier which is used to distinguish between lung pleura mesothelioma (circles) and adenocarcinoma (squares) based on expression levels of four miRs: hsa-miR-200a (SEQ ID NO. 5), hsa-miR-200b (SEQ ID NO. 6), hsa-miR-200c (SEQ ID NO. 11), and hsa-miR-141 (SEQ ID NO. 1) using logistic regression.

FIG. 2a shows the probability function based on Logistic regression performed on the logarithm of the expression level signal (by microarray) of the four miRNAs (y-axis). Samples (x-axis) are sorted according to their probability score.

FIG. 2b shows the probability function based on logistic regression of the four miRNAs (y-axis). Samples within each group are sorted separately according to their probability score (x-axis).

FIG. 2c shows the histogram of values of the probability function within each group showing the number of occurrences (Y-axis) for each range of values of the probability function (X-axis).

FIG. 2d shows the Area Under the Curve (AUC) of the exemplified classifier. The Y-axis represents the sensitivity and the X-axis represents (1-Specifity).

FIG. 4 demonstrates an exemplified classifier which is used to distinguish between lung pleura mesothelioma (circle) and a cancer originated from an organ selected from the group consisting of colon, kidney, liver, pancreas and stomach (squares) based on expression levels of two miRs: hsa-miR-200c (SEQ ID NO. 11) and hsa-miR-194 (SEQ ID NO. 4) using logistic regression.

FIG. 6 demonstrates an exemplified classifier which is used to distinguish between lung pleura mesothelioma (circles) and lung tumors (squares) based on expression levels two miRs: hsa-miR-200c (SEQ ID NO. 11) and hsa-miR-141 (SEQ ID NO. 1) using logistic regression.

FIG. 6a shows the probability function based on the Logistic regression performed on the logarithm of the expression level signal (by microarray) of the two miRNAs (y-axis). Samples (x-axis) are sorted according to their probability score.

FIG. 6b shows the probability function based on logistic regression of the two miRNAs (y-axis). Samples within each group are sorted separately according to their probability score (x-axis).

FIG. 6c shows the miRNA microarray of hsa-miR-200c (SEQ ID NO. 11) (x-axis) against the normalized Ct of hsa-miR-141 (SEQ ID NO. 1) (y-axis).

FIG. 6d shows the Area Under the Curve (AUC) of the exemplified classifier. The Y-axis represents the sensitivity and the X-axis represents (1-Specifity).

FIG. 7 demonstrates an exemplified classifier which is used to distinguish between lung pleura mesothelioma and lung tumors based on expression levels of two miRs: hsa-miR-193a (SEQ ID NO. 3) and hsa-miR-200a (SEQ ID NO. 5) using logistic regression.

FIG. 7a shows the probability function based on the Logistic regression performed on the logarithm of the expression level signal (by microarray) of the two miRNAs (y-axis). Samples (x-axis) are sorted according to their probability score.

FIG. 7b shows the probability function based on logistic regression of the two miRNAs (y-axis). Samples within each group are sorted separately according to their probability score (x-axis).

FIG. 7c shows the miRNA microarray of hsa-miR-193a (SEQ ID NO. 3) (x-axis) against the normalized Ct of hsa-miR-200a (SEQ ID NO. 5) (y-axis).

FIG. 7d shows the Area Under the Curve (AUC) of the exemplified classifier. The Y-axis represents the sensitivity and the X-axis represents (1-Specifity).

FIG. 8 demonstrates an exemplified classifier used to distinguish between lung pleura mesothelioma samples (circles) and lung adenocarcinoma samples (squares) using qRT-PCR based on two miRs: hsa-miR-141 (SEQ ID NO. 1) and hsa-miR-193a-3p (SEQ ID NO.10), using a linear combination, on 40 samples:

FIG. 8a shows the linear combination of the two miRNAs (y-axis). Samples (x-axis) are sorted according to their linear combination score.

FIG. 8b shows the linear combination of the two miRNAs (y-axis). Samples within each group are sorted separately according to their linear combination score (x-axis).

FIG. 8c shows the miRNA normalized Ct of hsa-miR-141 (SEQ ID NO. 1) (x-axis) against the normalized Ct of hsa-miR-193a-3p (SEQ ID NO. 10) (y-axis).

FIG. 8d shows the Area Under the Curve (AUC) of the exemplified classifier, wherein AUC=1. The Y-axis represents the sensitivity and the X-axis represents (1-Specifity).

FIG. 9 demonstrates an exemplified classifier used to distinguish between lung pleura mesothelioma samples (circles) and liver samples (squares) using qRT-PCR based on two miRs: hsa-miR-192 (SEQ ID NO. 2) and hsa-miR-122a (SEQ ID NO. 23), using a linear combination, on 25 samples:

FIG. 10 demonstrates an exemplified classifier used to distinguish between lung pleura mesothelioma samples (circles) and samples from either the pancreas or colon (squares) using qRT-PCR based on two miRs: hsa-miR-192 (SEQ ID NO. 2) and hsa-miR-193a-3p (SEQ ID NO. 10), using a linear combination, on 30 samples.

FIG. 10a shows the linear combination of the two miRNAs (y-axis). Samples (x-axis) are sorted according to their linear combination score.

FIG. 10b shows the linear combination of the two miRNAs (y-axis). Samples within each group are sorted separately according to their linear combination score (x-axis).

FIG. 10c shows the miRNA normalized Ct of hsa-miR-192 (SEQ ID NO. 2) (x-axis) against the normalized Ct of hsa-miR-193a-3p (SEQ ID NO. 10) (y-axis).

FIG. 10d shows the Area Under the Curve (AUC) of the exemplified classifier, wherein AUC=1. The Y-axis represents the sensitivity and the X-axis represents (1-Specifity).

FIG. 11 demonstrates an exemplified classifier used to distinguish between lung pleura mesothelioma samples (circles) and bladder samples (squares) using qRT-PCR based on two miRs: hsa-miR-141 (SEQ ID NO. 1) and hsa-miR-193a-3p (SEQ ID NO. 10), using a linear combination, on 25 samples:

FIG. 12 demonstrates an exemplified classifier used to distinguish between lung pleura mesothelioma samples (circles) and ovary and breast samples (squares) using qRT-PCR based on two miRs: hsa-miR-141 (SEQ ID NO. 1) and hsa-miR-193a-3p (SEQ ID NO.10) using a linear combination, on 25 samples:

FIG. 13 demonstrates an exemplified classifier which is used to distinguish between lung pleura mesothelioma samples (circles) and kidney samples (squares) using qRT-PCR based on two miRs: hsa-miR-192 (SEQ ID NO. 2) and hsa-miR-122a (SEQ ID NO. 23) using a linear combination, on 26 samples:

FIG. 14 shows the first step of the classifier, using the normalized Ct of hsa-miR-122 (SEQ ID NO. 24) (y-axis) and the normalized Ct of hsa-miR-192 (SEQ ID NO. 2) (x-axis). The solid lines represent the thresholds below which a sample was identified as "non-mesothelioma". The dashed lines represent Low Confidence interval. Seventeen samples for which the normalized Ct of hsa-miR-122 (SEQ ID NO. 24) was lower than 5.5 (lowest dashed line), or the normalized Ct of hsa-miR-192 (SEQ ID NO. 2) was lower than 7 (left-most dashed line) were considered Non-mesothelioma with high confidence.

FIG. 15 shows the second step of the classifier, using a linear combination of hsa-miR-200c (SEQ ID NO. 11) (x-axis) and hsa-miR-193a-3p (SEQ ID NO. 10) (y-axis), on 62 samples. The solid line represents the classifier. The dashed lines represent Low Confidence interval.

FIGS. 16 and 17 demonstrate a two step exemplified classifier used to distinguish between lung pleura mesothelioma samples (circles) and tumor samples of the following types: liver, kidney, pancreas, colon, bladder, ovary, breast and lung (squares).

FIG. 16 shows the first step of the classifier, using a linear combination of hsa-miR-192 (SEQ ID NO. 2) and hsa-miR-122a (SEQ ID NO. 23), on 29 samples. Samples that scored low on the combination of the two miRNAs were identified as "non-mesothelioma". The remaining samples continued to the next step.

FIG. 17 shows the second step of the classifier, using a linear combination of hsa-miR-141 (SEQ ID NO. 1) and hsa-miR-193a-3p (SEQ ID NO. 10), on 65 samples. Samples that scored low on the combination of the two miRNAs were identified as "non-mesothelioma". Samples that scored high on the combination of the two miRNAs were identified as "mesothelioma".

FIG. 17a shows the linear combination of the two miRNAs (y-axis). Samples (x-axis) are sorted according to their linear combination score.

FIG. 17b shows the linear combination of the two miRNAs (y-axis). Samples within each group are sorted separately according to their linear combination score (x-axis).

FIG. 17c shows the normalized Ct of hsa-miR-141 (SEQ ID NO. 1) (x-axis) against the normalized Ct of hsa-miR-193a-3p (SEQ ID NO. 10) (y-axis).

FIG. 17d shows the Area Under the Curve (AUC) of the exemplified classifier, wherein AUC=0.99468. The Y-axis represents the sensitivity and the X-axis represents (1-Specifity).

DETAILED DESCRIPTION OF THE INVENTION

Figure 1:
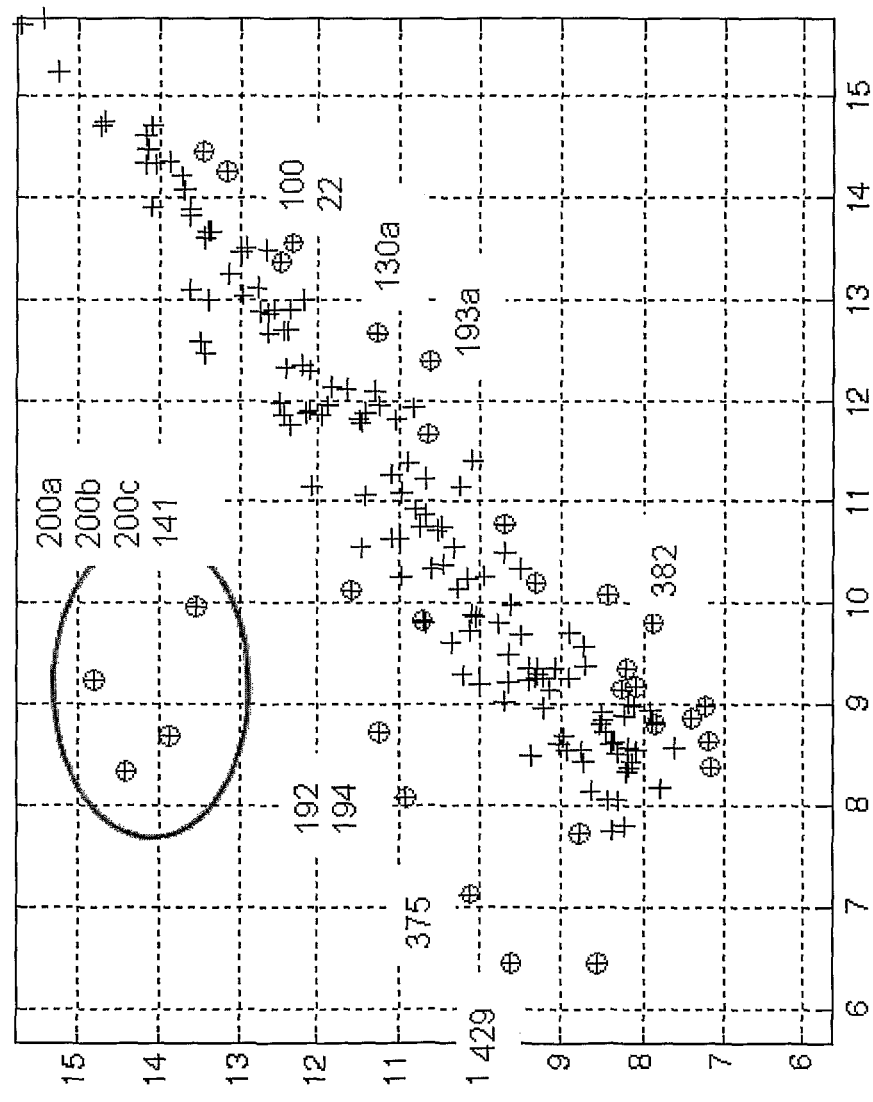
FIG. 1 shows the analysis of the microRNA array results (in log 2(fluorescence)) of lung pleura mesothelioma vs. adenocarcinoma. The x-axis shows the mean normalized expression level of 7 lung pleura mesothelioma samples and the y-axis shows the mean normalized expression level of 85 adenocarcinoma samples of different origins. As shown, miRs with higher expression levels in adenocarcinoma include hsa-miR-141 (SEQ ID NO. 1), hsa-miR-192 (SEQ ID NO. 2), hsa-miR-194 (SEQ ID NO. 4), hsa-miR-200a (SEQ ID NO. 5), hsa-miR-200b (SEQ ID NO. 6), hsa-miR-200c (SEQ ID NO. 11), hsa-miR-375 (SEQ ID NO. 8), and hsa-miR-429 (SEQ ID NO. 9).

The invention is based on the discovery that specific nucleic acids (SEQ ID NOS: 1-87) may be used for the identification, classification and diagnosis of specific cancers.

The present invention provides a sensitive, specific and accurate method which may be used to distinguish between different tumor origins.

The present invention further provides a method which may be used to distinguish between mesothelioma and other types of cancer including but not limited to adenocarcinoma, lung tumors, and tumors from a cancer originated from an organ selected from the group consisting of colon, kidney, liver, pancreas and stomach, and also a method to distinguish between Non Small Cell Lung Carcinoma (NSCLC) and non-squamous NSCLC.

Malignant Pleural Mesothelioma

Malignant pleural mesothelioma (MPM) is a relatively rare and aggressive tumor for which no effective therapy is still available, despite the discovery of many possible molecular and genetic targets. It is a solid, locally aggressive tumor of the pleura that covers and later invades the lung parenchyma, which leads to a severe clinically symptomatic disease with very poor median survival. A number of risk factors for the development of this malignancy have been described, foremost among them being exposure to asbestos and probably infection with the SV40 virus. Genetic susceptibility and familial clustering of cases have also been observed and apparently exposure to radiation and chronic infection are also risk factors. Yet, the late stage of the disease at which MPM is diagnosed, and the long latency that exists between some of the exposures and the diagnosis of the disease, have made it difficult to comprehensively evaluate the contribution of each of these risk factors and their downstream molecular effects to the pathogenesis of the disease.

The incidence of mesothelioma has clearly grown in recent years in all developed countries of Western Europe and North America, and most probably in developing counties as well, and thus the estimated number of patients that will develop the disease in coming years is also growing. Exposure to asbestos is still a major factor that contributes to the continuing growth in number of cases. The continuing growth in number of patients developing mesothelioma has also highlighted the importance of developing better means for early diagnosis and for the detection of the premalignant changes. Though no effective therapy is yet available, the much improved prognosis of patients with tumors at early stages strongly suggests that early detection may improve significantly survival and may possibly even prevent development of the tumor.

The term MPM is often misleading, since it includes different types of tumors with different cellular makeup, namely, epithelial, sarcomatous, and mixed. In a large study of mesotheliomas, epithelial mesothelioma was the most prevalent type (61.5%), followed by mixed/biphasic type (22%) and sarcomatous type (16.5%). Though the distinction between sarcomatous and epithelial types of mesothelioma is relatively easy, the distinction between the epithelial subtypes (including the mixed types), and adenocarcinoma of the lung that involves the pleura is often not easy and straightforward. Since over 70% of primary lung cancer will eventually involve the pleura, and a large number of other malignancies will metastasize to the lung and the pleura, the correct diagnosis of malignant mesothelioma and its distinction from other cancers is clearly of great importance. Because of the interobserver variations between pathologists in diagnosing mesothelioma and in distinguishing it from other cancers of the lung and pleura, and because of the absence of a single specific and reliable biomarker for the diagnosis of mesothelioma, there is an obvious need for a reliable and objective assay that would help the pathologist make this distinction with greater confidence.

The pathologic assessment of pleural lesions includes a variety of neoplastic and reactive conditions that may be difficult to distinguish. The most common diagnostic problems involve the distinction between epithelial malignant mesothelioma and adenocarcinoma, and between reactive epithelial or fibrous proliferations, and epithelial or sarcomatoid mesothelioma. This is made even more difficult when only pleural effusion fluid or small tissue samples are available for pathologic assessment. Over the past 20 years, immunohistochemistry has become the most extensively investigated technique in search of reliable objective tools for the diagnosis of mesothelioma. In spite of this intensive effort, there is no single immunostain that is entirely conclusive for either malignant mesothelioma or metastatic tumor. Furthermore, for most antibodies recorded in the literature and commercially available, the diagnostic value of each of them and the value of their combinations in immunohistochemical panels is still under debate. It is also true that many pathologists are not familiar enough with the histology of malignant mesothelioma, due to the low overall incidence of this tumor, and have therefore come to rely on immunodiagnosis almost entirely with the resultant increasing inaccuracies in diagnosis.

In spite of the advances made in immunohistochemistry, electron microscopy continues to be the "gold standard" for the differential diagnosis of mesothelioma from other tumors affecting the serosal surfaces. Electron microscopy has been most contributory in the diagnosis of the epithelial variant and is less helpful in the identification of sarcomatoid mesotheliomas. However due to the very limited amount of tissues available for EM diagnosis and the very big sampling error inherent in taking small pieces of tissue, the need for EM diagnosis comes only after all regular histological and immunohistochemical assessments have been exhausted. And even then the pitfalls for reaching the correct diagnosis are many.

Differential gene expression between malignant mesothelioma and normal pleura, as determined by microarrays, as well as by subtractive complementary DNA (cDNA) hybridization, has been able to show several genes that are associated with mesothelioma and can constitute a potential signature to the tumor. Thus, upregulation of c-myc, fra-1 and EGFR was demonstrated at different stages of carcinogenesis. Upregulation of osteopontin, zyxin and integrin-linked kinase found in mesothelioma, and later of CD44 and c-met, have also led to their application as potential tumor markers, some of which can also be detected in serum. It has also been possible to show that gene expression profiles in MPM can predict time to progression and survival patterns among separate groups of patients who underwent thoracic surgery. Surprisingly, no frequent changes in the classical members of tumor suppressor genes have been found in this context. Although p53 mutations have been found in MPM cell lines, there is a general sense that the contributions of p53 mutations in MPM pathogenesis are minor. However, homozygous deletion of p16/CDKN2A which is closely related to the activity of the pRb suppressor gene, has been reported in >70% of malignant mesotheliomas and has been associated with poor prognosis.

MicroRNAs (miRs, miRNAs) and Their Processing

A gene coding for a miRNA may be transcribed leading to production of a miRNA primary transcript known as the pri-miRNA. The pri-miRNA may comprise a hairpin with a stem and loop. The stem of the hairpin may comprise mismatched bases. The pri-miRNA may comprise several hairpins in a polycistronic structure.

The hairpin structure may be recognized by Drosha, which is an RNase III endonuclease. Drosha may recognize terminal loops in the pri-miRNA and cleave approximately two helical turns into the stem to produce a 60-70 nt precursor known as the pre-miRNA. Drosha may cleave the pri-miRNA with a staggered cut typical of RNase III endonucleases yielding a pre-miRNA stem loop with a 5' phosphate and ~2 nucleotide 3' overhang. Approximately one helical turn of stem (~10 nucleotides) extending beyond the Drosha cleavage site may be essential for efficient processing. The pre-miRNA may then be actively transported from the nucleus to the cytoplasm by Ran-GTP and the export receptor Ex-portin-5.

The pre-miRNA may be recognized by Dicer, which is also an RNase III endonuclease. Dicer may recognize the double-stranded stem of the pre-miRNA. Dicer may cleave off the terminal loop two helical turns away from the base of the stem loop leaving an additional 5' phosphate and ~2 nucleotide 3' overhang. The resulting siRNA-like duplex, which may comprise mismatches, comprises the mature miRNA and a similar-sized fragment known as the miRNA*. The miRNA and miRNA* may be derived from opposing arms of the pri-miRNA and pre-miRNA. miRNA* sequences may be found in libraries of cloned miRNAs but typically at lower frequency than the miRNAs.

Although initially present as a double-stranded species with miRNA*, the miRNA may eventually become incorporated as a single-stranded RNA into a ribonucleoprotein complex known as the RNA-induced silencing complex (RISC). Various proteins can form the RISC, which can lead to variability in specificity for miRNA/miRNA* duplexes, binding site of the target gene, activity of miRNA (repress or activate), and which strand of the miRNA/miRNA* duplex is loaded in to the RISC.

When the miRNA strand of the miRNA:miRNA* duplex is loaded into the RISC, the miRNA* may be removed and degraded. The strand of the miRNA:miRNA* duplex that is loaded into the RISC may be the strand whose 5' end is less tightly paired. In cases where both ends of the miRNA:miRNA* have roughly equivalent 5' pairing, both miRNA and miRNA* may have gene silencing activity.

The RISC may identify target nucleic acids based on high levels of complementarity between the miRNA and the mRNA, especially by nucleotides 2-7 of the miRNA. Only one case has been reported in animals where the interaction between the miRNA and its target was along the entire length of the miRNA. This was shown for miR-196 and Hox B8 and it was further shown that miR-196 mediates the cleavage of the Hox B8 mRNA (Yekta et al 2004, Science 304-594). Otherwise, such interactions are known only in plants (Bartel & Bartel 2003, Plant Physiol 132-709).

A number of studies have looked at the base-pairing requirement between miRNA and its mRNA target for achieving efficient inhibition of translation (reviewed by Bartel 2004, Cell 116-281). In mammalian cells, the first 8 nucleotides of the miRNA may be important (Doench & Sharp 2004 GenesDev 2004-504). However, other parts of the microRNA may also participate in mRNA binding. Moreover, sufficient base pairing at the 3' can compensate for insufficient pairing at the 5' (Brennecke et al, 2005 PLoS 3-e85). Computation studies, analyzing miRNA binding on whole genomes have suggested a specific role for bases 2-7 at the 5' of the miRNA in target binding but the role of the first nucleotide, found usually to be "A" was also recognized (Lewis et at 2005 Cell 120-15). Similarly, nucleotides 1-7 or 2-8 were used to identify and validate targets by Krek et al (2005, Nat Genet 37-495).

The target sites in the mRNA may be in the 5' UTR, the 3' UTR or in the coding region. Interestingly, multiple miRNAs may regulate the same mRNA target by recognizing the same or multiple sites. The presence of multiple miRNA binding sites in most genetically identified targets may indicate that the cooperative action of multiple RISCs provides the most efficient translational inhibition.

MiRNAs may direct the RISC to downregulate gene expression by either of two mechanisms: mRNA cleavage or translational repression. The miRNA may specify cleavage of the mRNA if the mRNA has a certain degree of complementarity to the miRNA. When a miRNA guides cleavage, the cut may be between the nucleotides pairing to residues 10 and 11 of the miRNA. Alternatively, the miRNA may repress translation if the miRNA does not have the requisite degree of complementarity to the miRNA. Translational repression may be more prevalent in animals since animals may have a lower degree of complementarity between the miRNA and binding site.

It should be noted that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

Nucleic Acids

Nucleic acids are provided herein. The nucleic acid may comprise the sequence of SEQ ID NOS: 1-87 or variants thereof. The variant may be a complement of the referenced nucleotide sequence. The variant may also be a nucleotide sequence that is substantially identical to the referenced nucleotide sequence or the complement thereof. The variant may also be a nucleotide sequence which hybridizes under stringent conditions to the referenced nucleotide sequence, complements thereof, or nucleotide sequences substantially identical thereto.

The nucleic acid may have a length of from 10 to 250 nucleotides. The nucleic acid may have a length of at least 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 125, 150, 175, 200 or 250 nucleotides. The nucleic acid may be synthesized or expressed in a cell (in vitro or in vivo) using a synthetic gene described herein. The nucleic acid may be synthesized as a single strand molecule and hybridized to a substantially complementary nucleic acid to form a duplex. The nucleic acid may be introduced to a cell, tissue or organ in a single- or double-stranded form or capable of being expressed by a synthetic gene using methods well known to those skilled in the art, including as described in U.S. Pat. No. 6,506,559 which is incorporated by reference.

Nucleic Acid Complexes

The nucleic acid may further comprise one or more of the following: a peptide, a protein, a RNA-DNA hybrid, an antibody, an antibody fragment, a Fab fragment, and an aptamer.

Pri-miRNA

The nucleic acid may comprise a sequence of a pri-miRNA or a variant thereof. The pri-miRNA sequence may comprise from 45-30,000, 50-25,000, 100-20,000, 1,000-1,500 or 80-100 nucleotides. The sequence of the pri-miRNA may comprise a pre-miRNA, miRNA and miRNA*, as set forth herein, and variants thereof. The sequence of the pri-miRNA may comprise the sequence of SEQ ID NOS: 1-22, 44-50, 55 and 58-87 or variants thereof.

The pri-miRNA may form a hairpin structure. The hairpin may comprise a first and a second nucleic acid sequence that are substantially complimentary. The first and second nucleic acid sequence may be from 37-50 nucleotides. The first and second nucleic acid sequence may be separated by a third sequence of from 8-12 nucleotides. The hairpin structure may have a free energy less than −25 Kcal/mole as calculated by the Vienna algorithm with default parameters, as described in Hofacker et al., Monatshefte f. Chemie 125: 167-188 (1994), the contents of which are incorporated herein. The hairpin may comprise a terminal loop of 4-20, 8-12 or 10 nucleotides. The pri-miRNA may comprise at least 19% adenosine nucleotides, at least 16% cytosine nucleotides, at least 23% thymine nucleotides and at least 19% guanine nucleotides.

Pre-miRNA

The nucleic acid may also comprise a sequence of a pre-miRNA or a variant thereof. The pre-miRNA sequence may comprise from 45-90, 60-80 or 60-70 nucleotides. The sequence of the pre-miRNA may comprise a miRNA and a miRNA* as set forth herein. The sequence of the pre-miRNA may also be that of a pri-miRNA excluding from 0-160 nucleotides from the 5' and 3' ends of the pri-miRNA. The sequence of the pre-miRNA may comprise the sequence of SEQ ID NOS: 1-22, 44-50, 55 and 58-87 as described in the Sanger miRBase registry (release 9.1 or 10) or variants thereof.

MiRNA

The nucleic acid may also comprise a sequence of a miRNA (including miRNA*) or a variant thereof. The miRNA sequence may comprise from 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be the first 13-33 nucleotides of the pre-miRNA. The sequence of the miRNA may also be the last 13-33 nucleotides of the pre-miRNA. The sequence of the miRNA may comprise the sequence of SEQ ID NOS: 1-12, 23-25, 44, 47, 49, 55 and 58-72 as described in the Sanger miRBase registry (release 9.1 or 10) or variants thereof.

Anti-miRNA

The nucleic acid may also comprise a sequence of an anti-miRNA that is capable of blocking the activity of a miRNA or miRNA*, such as by binding to the pri-miRNA, pre-miRNA, miRNA or miRNA* (e.g. antisense or RNA silencing), or by binding to the target 30 binding site. The anti-miRNA may comprise a total of 5-100 or 10-60 nucleotides. The anti-miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the anti-miRNA may comprise (a) at least 5 nucleotides that are substantially identical or complimentary to the 5' of a miRNA and at least 5-12 nucleotides that are substantially complimentary to the flanking regions of the target site from the 5' end of the miRNA, or (b) at least 5-U nucleotides that are substantially identical or complimentary to the 3' of a miRNA and at least 5 nucleotide that are substantially 5 complimentary to the flanking region of the target site from the 3' end of the miRNA. The sequence of the anti-miRNA may comprise the compliment of SEQ ID NOS: 1-12,23-25,44,47,49, 55 and 58-72 as described in the Sanger miRBase registry (release 9.1 or 10) or variants thereof.

Synthetic Gene

A synthetic gene is also provided comprising a nucleic acid described herein operably linked to a transcriptional and/or translational regulatory sequence. The synthetic gene may be capable of modifying the expression of a target gene with a binding site for a nucleic acid described herein. Expression of the target gene may be modified in a cell, tissue or organ. The synthetic gene may be synthesized or derived from naturally-occurring genes by standard recombinant techniques. The synthetic gene may also comprise terminators at the 3'-end of the transcriptional unit of the synthetic gene sequence. The synthetic gene may also comprise a selectable marker.

Vector

A vector is also provided comprising a synthetic gene described herein. The vector may be an expression vector. An expression vector may comprise additional elements. For example, the expression vector may have two replication systems allowing it to be maintained in two organisms, e.g., in one host cell for expression and in a second host cell (e.g., bacteria) for cloning and amplification. For integrating expression vectors, the expression vector may contain at least one sequence homologous to the host cell genome, and preferably two homologous sequences which flank the expression construct. The integrating vector may be directed to a specific locus in the host cell by selecting the appropriate homologous sequence for inclusion in the vector. The vector may also comprise a selectable marker gene to allow the selection of transformed host cells.

Probes

A probe is also provided comprising a nucleic acid described herein. Probes may be used for screening and diagnostic methods, as outlined below. The probe may be attached or immobilized to a solid substrate, such as a biochip.

The probe may have a length of from 8 to 500, 10 to 100 or 20 to 60 nucleotides. The probe may also have a length of at least 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 220, 240, 260, 280 or 300 nucleotides. The probe may further comprise a linker sequence of from 10-60 nucleotides.

Biochip

A biochip is also provided. The biochip may comprise a solid substrate comprising an attached probe or plurality of probes described herein. The probes may be capable of hybridizing to a target sequence under stringent hybridization conditions. The probes may be attached at spatially defined addresses on the substrate. More than one probe per target sequence may be used, with either overlapping probes or probes to different sections of a particular target sequence. The probes may be capable of hybridizing to target sequences associated with a single disorder appreciated by those in the art. The probes may either be synthesized first, with subsequent attachment to the biochip, or may be directly synthesized on the biochip.

The solid substrate may be a material that may be modified to contain discrete individual sites appropriate for the attachment or association of the probes and is amenable to at least one detection method. Representative examples of substrates include glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses and plastics. The substrates may allow optical detection without appreciably fluorescing.

The substrate may be planar, although other configurations of substrates may be used as well. For example, probes may be placed on the inside surface of a tube, for flow-through sample analysis to minimize sample volume. Similarly, the substrate may be flexible, such as flexible foam, including closed cell foams made of particular plastics.

The biochip and the probe may be derivatized with chemical functional groups for subsequent attachment of the two. For example, the biochip may be derivatized with a chemical functional group including, but not limited to, amino groups, carboxyl groups, oxo groups or thiol groups. Using these functional groups, the probes may be attached using functional groups on the probes either directly or indirectly using a linker. The probes may be attached to the solid support by either the 5' terminus, 3' terminus, or via an internal nucleotide.

The probe may also be attached to the solid support non-covalently. For example, biotinylated oligonucleotides can be made, which may bind to surfaces covalently coated with streptavidin, resulting in attachment. Alternatively, probes may be synthesized on the surface using techniques such as photopolymerization and photolithography.

Compositions

A pharmaceutical composition is also provided. The composition may comprise a nucleic acid described herein and optionally a pharmaceutically acceptable carrier. The compositions may be used for therapeutic applications. The pharmaceutical composition may be administered by known methods, including wherein a nucleic acid is introduced into a desired target cell in vitro or in vivo.

Methods for the delivery of nucleic acid molecules are described in Akhtar et al., (Trends Cell Bio. 2, 139, 1992). WO 94/02595 describes general methods for delivery of RNA molecules. These protocols can be utilized for the delivery of virtually any nucleic acid molecule. Nucleic acid molecules can be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. Alternatively, the nucleic acid/vehicle combination is locally delivered by direct injection or by use of an infusion pump. Other routes of delivery include, but are not limited to oral (tablet or pill form) and/or intrathecal delivery (Gold, 1997, Neuroscience, 76, 1153-1158). Other approaches include the use of various transport and carrier systems, for example, through the use of conjugates and biodegradable polymers. More detailed descriptions of nucleic acid delivery and administration are provided for example in WO93/23569, WO99/05094, and WO99/04819.

The nucleic acids can be introduced into tissues or host cells by any number of routes, including viral infection, microinjection, or fusion of vesicles. Jet injection may also be used for intra-muscular administration, as described by Furth et al. (Anal Biochem 115 205:365-368, 1992). The nucleic acids can be coated onto gold microparticles, and delivered intradermally by a particle bombardment device, or "gene gun" as described in the literature (see, for example, Tang et al. Nature 356:152-154, 1992), where gold microprojectiles are coated with the DNA, then bombarded into skin cells.

The compositions of the present invention can be formulated into pharmaceutical compositions by combination with appropriate, pharmaceutically acceptable carriers or diluents, and can be formulated into preparations in solid, semi-solid, liquid or gaseous forms, such as tablets, capsules, powders, granules, ointments, solutions, suppositories, injections, inhalants and aerosols. As such, administration of the agents can be achieved in various ways, including oral, buccal, rectal, parenteral, intraperitoneal, intradermal, transdermal, intratracheal, etc.

Diagnostic

A method of diagnosis is also provided. The method comprises detecting a differential expression level of a cancer-associated nucleic acid in a biological sample. The sample may be derived from a patient. Diagnosis of a cancer state in a patient may allow for prognosis and selection of therapeutic strategy. Further, the developmental stage of cells may be classified by determining temporarily expressed disease-associated nucleic acids.

In situ hybridization of labeled probes to tissue arrays may be performed. When comparing the fingerprints between an individual and a standard, the skilled artisan can make a diagnosis, a prognosis, or a prediction based on the findings. It is further understood that the genes which indicate the diagnosis may differ from those which indicate the prognosis and molecular profiling of the condition of the cells may lead to distinctions between responsive or refractory conditions or may be predictive of outcomes.

Kits

A kit is also provided and may comprise a nucleic acid described herein together with any or all of the following: assay reagents, buffers, probes and/or primers, and sterile saline or another pharmaceutically acceptable emulsion and suspension base. In addition, the kits may include instructional materials containing directions (e.g., protocols) for the practice of the methods described herein.

For example, the kit may be a kit for the amplification, detection, identification or quantification of a target nucleic acid sequence. The kit may comprise a poly(T) primer, a forward primer, a reverse primer, and a probe.

DEFINITIONS

It is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

Aberrant Proliferation

As used herein, the term "aberrant proliferation" means cell proliferation that deviates from the normal, proper, or expected course. For example, aberrant cell proliferation may include inappropriate proliferation of cells whose DNA or other cellular components have become damaged or defective. Aberrant cell proliferation may include cell proliferation whose characteristics are associated with an indication caused by, mediated by, or resulting in inappropriately high levels of cell division, inappropriately low levels of apoptosis, or both. Such indications may be characterized, for example, by single or multiple local abnormal proliferations of cells, groups of cells, or tissue(s), whether cancerous or non-cancerous, benign or malignant.

About

As used herein, the term "about" refers to +/−10%.

Antisense

The term "antisense," as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated.

Attached

"Attached" or "immobilized" as used herein to refer to a probe and a solid support may mean that the binding between the probe and the solid support is sufficient to be stable under conditions of binding, washing, analysis, and removal. The binding may be covalent or non-covalent. Covalent bonds may be formed directly between the probe and the solid support or may be formed by a cross linker or by inclusion of a specific reactive group on either the solid support or the probe or both molecules. Non-covalent binding may be one or more of electrostatic, hydrophilic, and hydrophobic interactions. Included in non-covalent binding is the covalent attachment of a molecule, such as streptavidin, to the support and the non-covalent binding of a biotinylated probe to the streptavidin. Immobilization may also involve a combination of covalent and non-covalent interactions.

Biological Sample

"Biological sample" as used herein means a sample of biological tissue or fluid that comprises nucleic acids. Such samples include, but are not limited to, tissue or fluid isolated from subjects. Biological samples may also include sections of tissues such as biopsy and autopsy samples, FFPE samples, frozen sections taken for histological purposes, blood, plasma, serum, sputum, stool, tears, mucus, hair, and skin. Biological samples also include explants and primary and/or transformed cell cultures derived from animal or patient tissues.

Biological samples may also be blood, a blood fraction, urine, effusions, ascitic fluid, saliva, cerebrospinal fluid, cervical secretions, vaginal secretions, endometrial secretions, gastrointestinal secretions, bronchial secretions, sputum, cell line, tissue sample, cellular content of fine needle aspiration (FNA) or secretions from the breast. A biological sample may be provided by removing a sample of cells from an animal, but can also be accomplished by using previously isolated cells (e.g., isolated by another person, at another time, and/or for another purpose), or by performing the methods described herein in vivo. Archival tissues, such as those having treatment or outcome history, may also be used.

Cancer

The term "cancer" is meant to include all types of cancerous growths or oncogenic processes, metastatic tissues or malignantly transformed cells, tissues, or organs, irrespective of histopathologic type or stage of invasiveness. Examples of cancers include but are nor limited to solid tumors and leukemias, including: apudoma, choristoma, branchioma, malignant carcinoid syndrome, carcinoid heart disease, carcinoma (e.g., Walker, basal cell, basosquamous, Brown-Pearce, ductal, Ehrlich tumor, non-small cell lung, oat cell, papillary, bronchiolar, bronchogenic, squamous cell, and transitional cell), histiocytic disorders, leukemia (e.g., B cell, mixed cell, null cell, T cell, T-cell chronic, HTLV-II-associated, lymphocytic acute, lymphocytic chronic, mast cell, and myeloid), histiocytosis malignant, Hodgkin disease, immunoproliferative small, non-Hodgkin lymphoma, plasmacytoma, reticuloendotheliosis, melanoma, chondroblastoma, chondroma, chondrosarcoma, fibroma, fibrosarcoma, giant cell tumors, histiocytoma, lipoma, liposarcoma, mesothelioma, myxoma, myxosarcoma, osteoma, osteosarcoma, Ewing sarcoma, synovioma, adenofibroma, adenolymphoma, carcinosarcoma, chordoma, craniopharyngioma, dysgerminoma, hamartoma, mesenchymoma, mesonephroma, myosarcoma, ameloblastoma, cementoma, odontoma, teratoma, thymoma, trophoblastic tumor, adeno-carcinoma, adenoma, cholangioma, cholesteatoma, cylindroma, cystadenocarcinoma, cystadenoma, granulosa cell tumor, gynandroblastoma, hepatoma, hidradenoma, islet cell tumor, Leydig cell tumor, papilloma, Sertoli cell tumor, theca cell tumor, leiomyoma, leiomyosarcoma, myoblastoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, paraganglioma nonchromaffin, angiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, carcinosarcoma, chondrosarcoma, cystosarcoma, phyllodes, fibrosarcoma, hemangiosarcoma, leimyosarcoma, leukosarcoma, liposarcoma, lymphangiosarcoma, myosarcoma, myxosarcoma, ovarian carcinoma, rhabdomyosarcoma, sarcoma (e.g., Ewing, experimental, Kaposi, and mast cell), neurofibromatosis, and cervical dysplasia, and other conditions in which cells have become immortalized or transformed.

Classification

The term classification refers to a procedure and/or algorithm in which individual items are placed into groups or classes based on quantitative information on one or more characteristics inherent in the items (referred to as traits, variables, characters, features, etc) and based on a statistical model and/or a training set of previously labeled items. A "classification tree" is a decision tree that places categorical variables into classes.

Complement

"Complement" or "complementary" as used herein to refer to a nucleic acid may mean Watson-Crick (e.g., A-T/U and C-G) or Hoogsteen base pairing between nucleotides or nucleotide analogs of nucleic acid molecules. A full complement or fully complementary may mean 100% complementary base pairing between nucleotides or nucleotide analogs of nucleic acid molecules.

Ct

Ct signals represent the first cycle of PCR where amplification crosses a threshold (cycle threshold) of fluorescence. Accordingly, low values of Ct represent high abundance or expression levels of the microRNA.

In some embodiments the PCR Ct signal is normalized such that the normalized Ct remains inversed from the expression level. In other embodiments the PCR Ct signal may be normalized and then inverted such that low normalized-inverted Ct represent low abundance or expression levels of the microRNA.

Data Processing Routine

As used herein, a "data processing routine" refers to a process that can be embodied in software that determines the biological significance of acquired data (i.e., the ultimate results of an assay or analysis). For example, the data processing routine can make determination of tissue of origin based upon the data collected. In the systems and methods herein, the data processing routine can also control the data collection routine based upon the results determined. The data processing routine and the data collection routines can be integrated and provide feedback to operate the data acquisition, and hence provide assay-based judging methods.

Data Set

As use herein, the term "data set" refers to numerical values obtained from the analysis, These numerical values associated with analysis may be values such as peak height and area under the curve.

Data Structure

As used herein the term "data structure" refers to a combination of two or more data sets, applying one or more mathematical manipulations to one or more data sets to obtain one or more new data sets, or manipulating two or more data sets into a form that provides a visual illustration of the data in a new way. An example of a data structure prepared from manipulation of two or more data sets would be a hierarchical cluster.

Detection

"Detection" means detecting the presence of a component in a sample. Detection also means detecting the absence of a component. Detection also means measuring the level of a component, either quantitatively or qualitatively.

Differential Expression

"Differential expression" means qualitative or quantitative differences in the temporal and/or cellular gene expression patterns within and among cells and tissue. Thus, a differentially expressed gene may qualitatively have its expression altered, including an activation or inactivation, in, e.g., normal versus disease tissue. Genes may be turned on or turned off in a particular state, relative to another state thus permitting comparison of two or more states. A qualitatively regulated gene may exhibit an expression pattern within a state or cell type which may be detectable by standard techniques. Some genes may be expressed in one state or cell type, but not in both. Alternatively, the difference in expression may be quantitative, e.g., in that expression is modulated, either up-regulated, resulting in an increased amount of transcript, or down-regulated, resulting in a decreased amount of transcript. The degree to which expression differs need only be large enough to quantify via standard characterization techniques such as expression arrays, quantitative reverse transcriptase PCR, northern analysis, real-time PCR, in situ hybridization and RNase protection.

Expression Profile

"Expression profile" as used herein may mean a genomic expression profile, e.g., an expression profile of microRNAs. Profiles may be generated by any convenient means for determining a level of a nucleic acid sequence e.g. quantitative hybridization of microRNA, labeled microRNA, amplified microRNA, cRNA, etc., quantitative PCR, ELISA for quantification, and the like, and allow the analysis of differential gene expression between two samples. A subject or patient tumor sample, e.g., cells or collections thereof, e.g., tissues, is assayed. Samples are collected by any convenient method, as known in the art. Nucleic acid sequences of interest are nucleic acid sequences that are found to be indicative, including the nucleic acid sequences provided above, where the expression profile may include expression data for 5, 10, 20, 25, 50, 100 or more of, including all of the listed nucleic acid sequences. The expression profile may be based measuring the level or abundance of the nucleic acids, or may be based on a combined metric score thereof.

Expression Ratio

"Expression ratio" as used herein refers to relative expression levels of two or more nucleic acids as determined by detecting the relative expression levels of the corresponding nucleic acids in a biological sample.

FDR

When performing multiple statistical tests, for example in comparing the signal between two groups in multiple data features, there is an increasingly high probability of obtaining false positive results, by random differences between the groups that can reach levels that would otherwise be considered as statistically significant. In order to limit the proportion of such false discoveries, statistical significance is defined only for data features in which the differences reached a p-value (by two-sided t-test) below a threshold, which is dependent on the number of tests performed and the distribution of p-values obtained in these tests.

Fragment

"Fragment" is used herein to indicate a non-full length part of a nucleic acid or polypeptide. Thus, a fragment is itself also a nucleic acid or polypeptide, respectively.

Gene

"Gene" used herein may be a natural (e.g., genomic) or synthetic gene comprising transcriptional and/or translational regulatory sequences and/or a coding region and/or non-translated sequences (e.g., introns, 5'- and 3'-untranslated sequences). The coding region of a gene may be a nucleotide sequence coding for an amino acid sequence or a functional RNA, such as tRNA, rRNA, catalytic RNA, siRNA, miRNA or antisense RNA. A gene may also be an mRNA or cDNA corresponding to the coding regions (e.g., exons and miRNA) optionally comprising 5'- or 3'-untranslated sequences linked thereto. A gene may also be an amplified nucleic acid molecule produced in vitro comprising all or a part of the coding region and/or 5'- or 3'-untranslated sequences linked thereto.

Groove Binder/Minor Groove Binder (MGB)

"Groove binder" and/or "minor groove binder" may be used interchangeably and refer to small molecules that fit into the minor groove of double-stranded DNA, typically in a sequence-specific manner. Minor groove binders may be long, flat molecules that can adopt a crescent-like shape and thus, fit snugly into the minor groove of a double helix, often displacing water. Minor groove binding molecules may typically comprise several aromatic rings connected by bonds with torsional freedom such as furan, benzene, or pyrrole rings. Minor groove binders may be antibiotics such as netropsin, distamycin, berenil, pentamidine and other aromatic diamidines, Hoechst 33258, SN 6999, aureolic antitumor drugs such as chromomycin and mithramycin, CC-1065, dihydrocyclopyrroloindole tripeptide ($DPI_3$), 1,2-dihydro-(3H)-pyrrolo[3,2-e]indole-7-carboxylate ($CDPI_3$), and related compounds and analogues, including those described in Nucleic Acids in Chemistry and Biology, 2d ed., Blackburn and Gait, eds., Oxford University Press, 1996, and PCT Published Application No. WO 03/078450, the contents of which are incorporated herein by reference. A minor groove binder may be a component of a primer, a probe, a hybridization tag complement, or combinations thereof. Minor groove binders may increase the $T_m$ of the primer or a probe to which they are attached, allowing such primers or probes to effectively hybridize at higher temperatures.

Identity

"Identical" or "identity" as used herein in the context of two or more nucleic acids or polypeptide sequences may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

In Situ Detection

"In situ detection" as used herein means the detection of expression or expression levels in the original site hereby meaning in a tissue sample such as biopsy Label "Label" as used herein may mean a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and other entities which can be made detectable. A label may be incorporated into nucleic acids and proteins at any position.

Logistic Regression

Logistic regression is part of a category of statistical models called generalized linear models. Logistic regression allows one to predict a discrete outcome, such as group membership, from a set of variables that may be continuous, discrete, dichotomous, or a mix of any of these. The dependent or response variable can be dichotomous, for example, one of two possible types of cancer. Logistic regression models the natural log of the odds ratio, i.e. the ratio of the probability of belonging to the first group (P) over the probability of belonging to the second group (1-P), as a linear combination of the different expression levels (in log-space). The logistic regression output can be used as a classifier by prescribing that a case or sample will be classified into the first type if P is greater than 0.5 or 50%. Alternatively, the calculated probability P can be used as a variable in other contexts such as a 1D or 2D threshold classifier.

1D/2D Threshold Classifier

"1D/2D threshold classifier" used herein may mean an algorithm for classifying a case or sample such as a cancer sample into one of two possible types such as two types of cancer. For a 1D threshold classifier, the decision is based on one variable and one predetermined threshold value; the sample is assigned to one class if the variable exceeds the threshold and to the other class if the variable is less than the threshold. A 2D threshold classifier is an algorithm for classifying into one of two types based on the values of two variables. A threshold may be calculated as a function (usually a continuous or even a monotonic function) of the first variable; the decision is then reached by comparing the second variable to the calculated threshold, similar to the 1D threshold classifier.

Nucleic Acid

"Nucleic acid" or "oligonucleotide" or "polynucleotide" used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

A nucleic acid will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. N6-methyl adenosine are suitable. The 2'-OH-group may be replaced by a group selected from H, OR, R, halo, SH, SR, $NH_2$, $NHR$, $NR_2$ or CN, wherein R is $C_1$-$C_6$ alkyl, alkenyl or alkynyl and halo is F, Cl, Br or I.

Modified nucleotides also include nucleotides conjugated with cholesterol through, e.g., a hydroxyprolinol linkage as described in Krutzfeldt et al., Nature 438:685-689 (2005), Soutschek et al., Nature 432:173-178 (2004), and U.S. Patent Publication No. 20050107325, which are incorporated herein by reference. Additional modified nucleotides and nucleic acids are described in U.S. Patent Publication No. 20050182005, which is incorporated herein by reference. Modifications of the ribose-phosphate backbone may be done for a variety of reasons, e.g., to increase the stability and half-life of such molecules in physiological environments, to enhance diffusion across cell membranes, or as probes on a biochip. The backbone modification may also enhance resistance to degradation, such as in the harsh endocytic environment of cells. The backbone modification may also reduce nucleic acid clearance by hepatocytes, such as in the liver and kidney. Mixtures of naturally occurring nucleic acids and analogs may be made; alternatively, mixtures of different nucleic acid analogs, and mixtures of naturally occurring nucleic acids and analogs may be made.

Probe

"Probe" as used herein may mean an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids described herein. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled such as with biotin to which a streptavidin complex may later bind.

Promoter

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

Reference Expression Profile

As used herein, the phrase "reference expression profile" refers to a criterion expression value to which measured values are compared in order to determine the detection of a subject with lung cancer. The reference expression profile may be based on the abundance of the nucleic acids, or may be based on a combined metric score thereof.

Selectable Marker

"Selectable marker" used herein may mean any gene which confers a phenotype on a host cell in which it is expressed to facilitate the identification and/or selection of cells which are transfected or transformed with a genetic construct. Representative examples of selectable markers include the ampicillin-resistance gene (Amp$^r$), tetracycline-resistance gene (Tc$^r$), bacterial kanamycin-resistance gene (Kan$^r$), zeocin resistance gene, the AURI-C gene which confers resistance to the antibiotic aureobasidin A, phosphinothricin-resistance gene, neomycin phosphotransferase gene (nptII), hygromycin-resistance gene, beta-glucuronidase (GUS) gene, chloramphenicol acetyltransferase (CAT) gene, green fluorescent protein (GFP)-encoding gene and luciferase gene.

Sensitivity

"sensitivity" used herein may mean a statistical measure of how well a binary classification test correctly identifies a condition, for example how frequently it correctly classifies a cancer into the correct type out of two possible types. The sensitivity for class A is the proportion of cases that are determined to belong to class "A" by the test out of the cases that are in class "A", as determined by some absolute or gold standard.

Specificity

"Specificity" used herein may mean a statistical measure of how well a binary classification test correctly identifies a condition, for example how frequently it correctly classifies a cancer into the correct type out of two possible types. The specificity for class A is the proportion of cases that are determined to belong to class "not A" by the test out of the cases that are in class "not A", as determined by some absolute or gold standard.

Stringent Hybridization Conditions

"Stringent hybridization conditions" used herein may mean conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

Substantially Complementary

"Substantially complementary" used herein may mean that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides, or that the two sequences hybridize under stringent hybridization conditions.

Substantially Identical

"Substantially identical" used herein may mean that a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or with respect to nucleic acids, if the first sequence is substantially complementary to the complement of the second sequence.

Subject

As used herein, the term "subject" refers to a mammal, including both human and other mammals. The methods of the present invention are preferably applied to human subjects.

Target

"Target" as used herein may mean a polynucleotide that may be bound by one or more probes under stringent hybridization conditions.

Target Nucleic Acid

"Target nucleic acid" as used herein means a nucleic acid or variant thereof that may be bound by another nucleic acid. A target nucleic acid may be a DNA sequence. The target nucleic acid may be RNA. The target nucleic acid may comprise a mRNA, tRNA, shRNA, siRNA or Piwi-interacting RNA, or a pri-miRNA, pre-miRNA, miRNA, or anti-miRNA.

The target nucleic acid may comprise a target miRNA binding site or a variant thereof. One or more probes may bind the target nucleic acid. The target binding site may comprise 5-100 or 10-60 nucleotides. The target binding site may comprise a total of 5, 6, 7, 8, 9, 10, 11, 12, 13, 14, 15, 16, 17, 18, 19, 20, 21, 22, 23, 24, 25, 26, 27, 28, 29, 30-40, 40-50, 50-60, 61, 62 or 63 nucleotides. The target site sequence may comprise at least 5 nucleotides of the sequence of a target miRNA binding site disclosed in U.S. patent application Ser. Nos. 11/384,049, 11/418,870 or 11/429,720, the contents of which are incorporated herein.

Threshold Expression Profile

As used herein, the phrase "threshold expression profile" refers to a criterion expression profile to which measured values are compared in order to classify a cancer.

Tissue Sample

As used herein, a tissue sample is tissue obtained from a tissue biopsy using methods well known to those of ordinary skill in the related medical arts. The phrase "suspected of being cancerous" as used herein means a cancer tissue sample believed by one of ordinary skill in the medical arts to contain cancerous cells. Methods for obtaining the sample from the biopsy include gross apportioning of a mass, microdissection, laser-based microdissection, or other art-known cell-separation methods.

Variant

"Variant" used herein to refer to a nucleic acid may mean (i) a portion of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequence substantially identical thereto.

Vector

"Vector" as used herein means a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

Wild Type

As used herein, the term "wild type" sequence refers to a coding, a non-coding or an interface sequence which is an allelic form of sequence that performs the natural or normal function for that sequence. Wild type sequences include multiple allelic forms of a cognate sequence, for example, multiple alleles of a wild type sequence may encode silent or conservative changes to the protein sequence that a coding sequence encodes.

EXAMPLES

The following examples are presented in order to more fully illustrate some embodiments of the invention. They should, in no way be construed, however, as limiting the broad scope of the invention.

Example 1

Microarray Assay to Distinguish Between Mesothelioma and Other Tumors

1a) Samples

Tumor samples were obtained from several sources. Institutional review approvals were obtained for all samples in accordance with each institute's IRB or IRB-equivalent guidelines. For formalin fixed, paraffin-embedded (FFPE) samples, initial diagnosis, histological type, grade and tumor percentages were determined by a pathologist on hematoxilin-eosin (H&E) stained slides, performed on the first and/or last sections of the sample. Clinical records were reviewed for cases of misclassifications.

RNA was extracted from paraffin-embedded (FFPE) tissues originated from the following sources: lung pleura mesothelioma (7 samples), lung adenocarcinoma (15 samples), breast adenocarcinoma (14 samples), cervical adenocarcinoma (3 samples), colon adenocarcinoma (20 samples), esophagus adenocarcinoma (2 samples), esophagus-stomach adenocarcinoma (12 samples), pancreas adenocarcinoma (4 samples), prostate adenocarcinoma (3 samples), small intestine adenocarcinoma (1 sample), adenocarcinoma of unknown origin (11 samples), colon tumors (20 samples), kidney tumors (19 samples), liver tumors (6 samples), pancreas tumors (8 samples), stomach tumors (6 samples), lung carcinoid tumors (7 samples), lung neuroendocrine tumor (1 sample), lung neuroendocrine-large cell carcinoma (1 sample), lung non-small cell carcinoma (1 sample), lung non-small-large cell carcinoma (5 samples), lung tumor (2 samples), lung small cell carcinoma (8 samples) and lung non-small-squamous carcinoma (9 samples).

1b) Array Platform

Custom microarrays were produced by printing DNA oligonucleotide probes representing 688 miRNAs [Sanger database, version 9.1 (miRBase: microRNA sequences, targets and gene nomenclature. Griffiths-Jones S, Grocock R J, van Dongen S, Bateman A, Enright A J. NAR, 2006, 34, Database Issue, D140-D144) and additional Rosetta Genomics validated and predicted miRs]. Each probe carries up to 22-nt linker at the 3' end of the miRNA's complement sequence in addition to an amine group used to couple the probes to coated glass slides. 20 μM of each probe were dissolved in 2×SSC+ 0.0035% SDS and spotted in triplicate on Schott Nexterion® Slide E coated microarray slides using a Genomic Solutions® BioRobotics MicroGrid II according the MicroGrid manufacturer's directions. 64 negative control probes were designed using the sense sequences of different miRNAs. Two groups of positive control probes were designed to hybridize to array (1) synthetic spikes small RNA were added to the RNA before labeling to verify the labeling efficiency and (2) probes for abundant small RNA (e.g. small nuclear RNAs (U43, U49, U24, Z30, U6, U48, U44), 5.8 s and 5 s ribosomal RNA) were spotted on the array to verify RNA quality. The slides were blocked in a solution containing 50 mM ethanolamine, 1M Tris (pH 9.0) and 0.1% SDS for 20 min at 50° C., then thoroughly rinsed with water and spun dry.

1c) Cy-Dye Labeling

15 μg of total RNA was labeled by ligation of a RNA-linker p-rCrU-Cy-dye (Thomson et al., 2004, Nat Methods 1, 47-53) (Dharmacon) to the 3'-end with Cy3 or Cy5. The labeling reaction contained total RNA, spikes (20-0.1 fmoles), 500 ng RNA-linker-dye, 15% DMSO, 1× ligase buffer and 20 units of T4 RNA ligase (NEB) and proceeded at 4° C. for 1 hr followed by 1 hr at 37° C. The labeled RNA was mixed with 3× hybridization buffer (Ambion), heated to 95° C. for 3 min and than added on top of the array. Slides were hybridize 12-16 hr, followed by two washes with 1×SSC and 0.2% SDS and a final wash with 0.1×SSC.

The array was scanned using an Agilent Microarray Scanner Bundle G2565BA (resolution of 10 μm at 100% power). The data was analyzed using SpotReader software.

1d) RNA Extraction

Total RNA from FFPE samples was extracted according to the following protocol: 1 ml Xylene (Biolab) was added to 1-2 mg tissue, incubated at 57° C. for 5 min and centrifuged for 2 min at 10,000 g. The supernatant was removed and 1 ml Ethanol (100%) (Biolab) was added. Following centrifugation for 10 min at 10,000 g, the supernatant was discarded and the washing procedure was repeated. Following air drying for 10-15 min, 500 μl Buffer B (NaCl 10 mM, Tris pH 7.6, 500 mM, EDTA 20 mM, SDS 1%) and 5 ul proteinase K (50 mg/ml) (Sigma) were added. Following incubation at 45° C. for 16 h, inactivation of the proteinase K at 100° C. for 7 min was preformed. Following extraction with acid phenol chloroform (1:1) (Sigma) and centrifugation for 10 min at maximum speed at 4° C., the upper phase was transferred to a new tube with the addition of 3 volumes of 100% Ethanol, 0.1 volume of NaOAc (BioLab) and 8 μl glycogen (Ambion) and left over night at −20° C. Following centrifugation at maximum speed for 40 min at 4° C., washing with 1 ml Ethanol (85%), and drying, the RNA was re-suspended in 45 μl DDW.

The RNA concentration was tested and DNase Turbo (Ambion) was added accordingly (1 μl DNase/10 μg RNA). Following Incubation for 30 min at room temperature and extraction with acid phenol chloroform, the RNA was re-suspend in 45 μl DDW. The RNA concentration was tested again and DNase Turbo (Ambion) was added accordingly (1 μl DNase/ 10 μg RNA). Following incubation for 30 min at room temperature and extraction with acid phenol chloroform, the RNA was re-suspend in 20 μl DDW.

1e) Signal Calculation and Normalization

The initial data set consisted of signals measured for multiple probes for every sample. Triplicate spots were combined to produce one signal for each probe by taking the logarithmic mean of reliable spots. For the analysis, signals were used only for probes that were designed to measure the expression levels of known or validated human microRNAs. All data was log-transformed (natural base) and the analysis was performed in log-space. A reference data vector for normalization R was calculated by taking the median expression level for each probe across all samples. For each sample data vector S, a 2nd degree polynomial F was found so as to provide the best fit between the sample data and the reference data, such that R≈F(S). Remote data points ("outliers") were not used for fitting the polynomial F. For each probe in the sample (element $S_i$ in the vector S), the normalized value (in log-space) $M_i$ is calculated from the initial value $S_i$ by transforming it with the polynomial function F, so that $M_i$=F($S_i$).

1f) Logistic Regression

The aim of a logistic regression model is to use several features, such as expression levels of several microRNAs, to assign a probability of belonging to one of two possible groups. Logistic regression models the natural log of the odds ratio, i.e. the ratio of the probability of belonging to the first group (P) over the probability of belonging to the second group (1-P), as a linear combination of the different expression levels (in log-space). The logistic regression assumes that:

$$\ln\left(\frac{P}{1-P}\right) = \beta_0 + \sum_{i=1}^{N} \beta_i \cdot M_i = \beta_0 + \beta_1 \cdot M_1 + \beta_2 \cdot M_2 + \dots ,$$

where $\beta_0$ is the bias, $M_i$ is the expression level (normalized, in log-space) of the i-th microRNA used in the classification, and $\beta_i$ is its corresponding coefficient.

The probability output of the logistic model (P) is here converted to a binary decision using a 1D threshold classifier by comparing P to a threshold, denoted by $P_{TH}$, i.e. if $P > P_{TH}$ then the sample belongs to a "first group" and vice versa. $P_{TH}$ is chosen such that the number of classification errors is minimized.

Example 1.1

Specific MicroRNAs are Able to Distinguish Between Mesothelioma and Adenocarcinoma The analysis of the arrays results of lung pleura mesothelioma (seven samples) vs. adenocarcinoma (85 samples) are presented in FIG. 1. The results exhibited a significant difference in the expression pattern of several miRs, as indicated in Table 1.

TABLE 1

| miR name | MID | HID | P value |
|---|---|---|---|
| hsa-miR-200a | 5 | 18 | 3.0673e-011 |
| hsa-miR-200b | 6 | 19 | 2.0143e-014 |
| hsa-miR-200c | 11 | 20 | 2.4916e-018 |
| hsa-miR-141 | 1 | 13 | 6.4688e-019 |
| hsa-miR-192 | 2 | 14 | 0.007 |
| hsa-miR-194 | 4 | 16 | 0.0025 |
| hsa-miR-375 | 8 | 21 | 1.9358e-004 |
| hsa-miR-193a | 3 | 15 | 3.1308e-004 |
| hsa-miR-429 | 9 | 22 | 2.6630e-009 | miR name: is the miRBase registry name (release 9.1).
MID: is the SEQ ID NO. of the mature microRNA.
HID: is the SEQ ID NO. of the microRNA hairpin precursor (Pre-microRNA).
p-value: is the result of unpaired two-sided t-test between the two groups of samples.

These miRs can be used to distinguish between mesothelioma and adenocarcinoma tumors (either primary or metastasis). The classification could be done either with a simple threshold (1 or 2 dimension threshold), a logistic regression model or any other classifier.

An exemplified classifier using logistic regression based on four miRs: hsa-miR-200a (SEQ ID NO. 5), hsa-miR-200b (SEQ ID NO. 6), hsa-miR-200c (SEQ ID NO. 11), and hsa-miR-141 (SEQ ID NO. 1) as detected by microarray is demonstrated in FIG. 2. The sensitivity of the detection of lung pleura mesothelioma is 100% and the specificity of the signal is 98%. The p-value of the classifier is 2.74e-24.

Example 1.2

Figure 3:
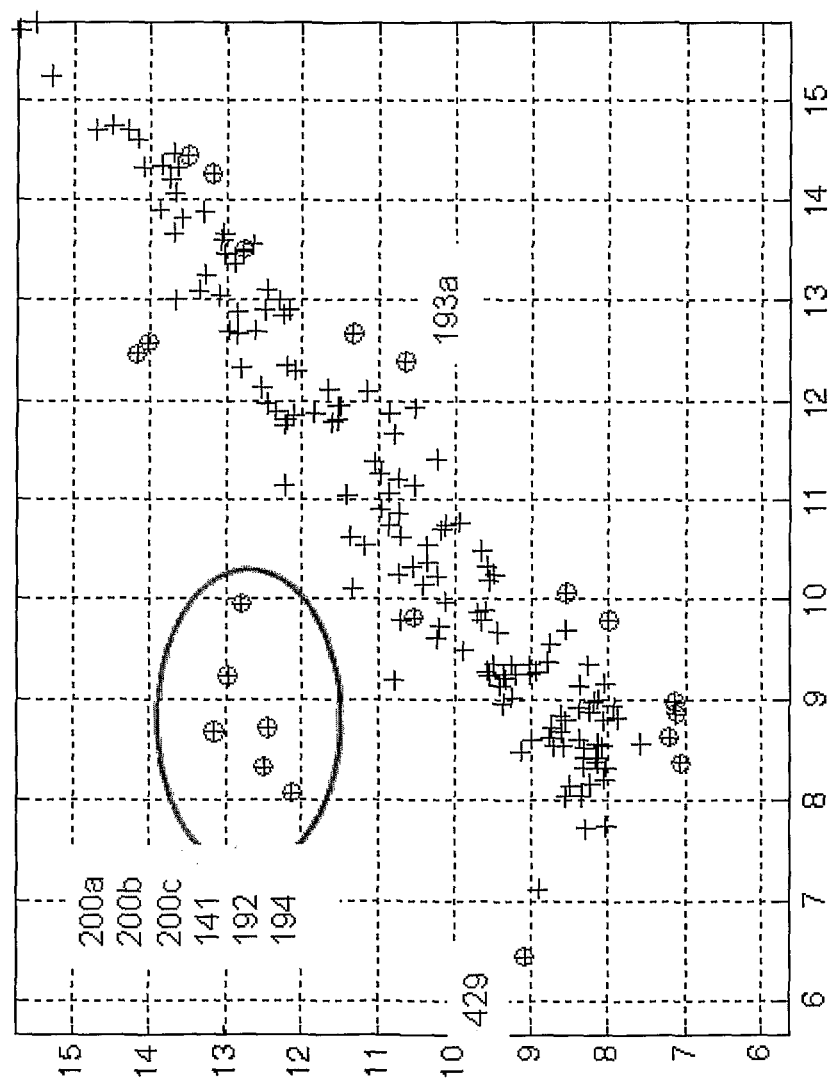
FIG. 3 shows the analysis of the microRNA array results (in log 2(fluorescence)) of mesothelioma vs. a cancer originated from an organ selected from the group consisting of colon, kidney, liver, pancreas and stomach. The x-axis shows the mean normalized expression level of 7 lung pleura mesothelioma samples and the y-axis shows the mean normalized expression level of samples from a cancer originated from an organ selected from the group consisting of colon, kidney, liver, pancreas and stomach. As shown, miRs with significantly higher expression in lung pleura mesothelioma include hsa-miR-193a (SEQ ID NO. 3), and miRs with higher expression levels in samples from a cancer originated from an organ selected from the group consisting of colon, kidney, liver, pancreas and stomach include hsa-miR-141 (SEQ ID NO. 1), hsa-miR-192 (SEQ ID NO. 2), hsa-miR-194 (SEQ ID NO. 4), hsa-miR-200a (SEQ ID NO. 5), hsa-miR-200b (SEQ ID NO. 6), hsa-miR-200c (SEQ ID NO. 11) and hsa-miR-429 (SEQ ID NO. 9).
Figure 4A:
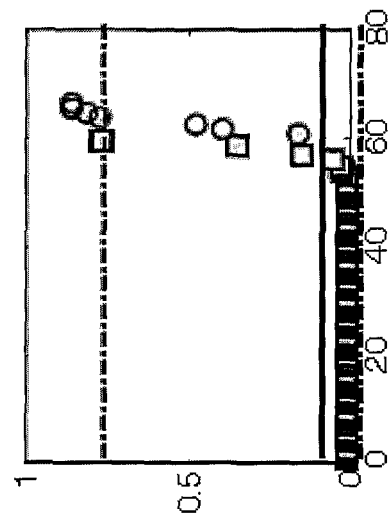
FIG. 4a shows the probability function based on the Logistic regression performed on the logarithm of the expression level signal (by microarray) of the two miRNAs (y-axis). Samples (x-axis) are sorted according to their probability score.
Figure 4B:
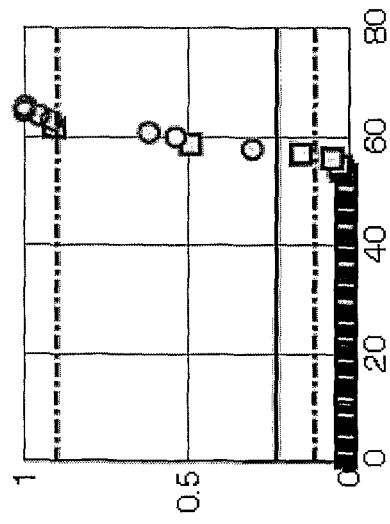
FIG. 4b shows the probability function based on logistic regression of the two miRNAs (y-axis). Samples within each group are sorted separately according to their probability score (x-axis).
Figure 4C:
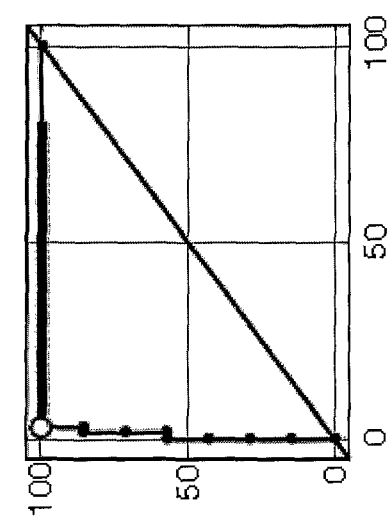
FIG. 4c shows the miRNA microarray of hsa-miR-200c (SEQ ID NO. 11) (x-axis) against the normalized Ct of hsa-miR-194 (SEQ ID NO. 4) (y-axis).
Figure 4D:
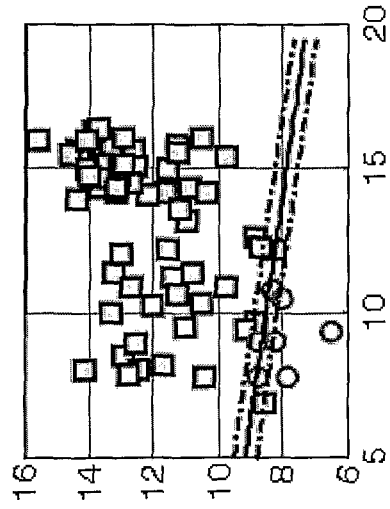
FIG. 4d shows the Area Under the Curve (AUC) of the exemplified classifier. The Y-axis represents the sensitivity and the X-axis represents (1-Specifity).

Specific MicroRNAs are Able to Distinguish Between Mesothelioma and Tumors from Colon, Kidney, Liver, Pancreas or Stomach The analysis of the arrays results of mesothelioma (seven samples) vs. tumors from colon, kidney, liver, pancreas or stomach (59 samples) are presented in FIG. 3. The results exhibited a significant difference in the expression pattern of several miRs, as indicated in Table 2.

TABLE 2

| miR name | MID | HID | p-value |
|---|---|---|---|
| hsa-miR-200a | 5 | 18 | 1.7955e-005 |
| hsa-miR-200b | 6 | 19 | 6.2771e-007 |
| hsa-miR-200c | 11 | 20 | 8.5999e-004 |
| hsa-miR-141 | 1 | 13 | 7.5743e-004 |
| hsa-miR-192 | 2 | 14 | 1.0248e-006 |
| hsa-miR-194 | 4 | 16, 17 | 8.5750e-008 |
| hsa-miR-193a | 3 | 15 | 5.1206e-005 |
| hsa-miR-429 | 9 | 22 | 2.1656e-004 | miR name: is the miRBase registry name (release 9.1).
MID: is the SEQ ID NO of the mature microRNA.
HID: is the SEQ ID NO of the microRNA hairpin precursor (Pre-microRNA).
p-value: is the result of unpaired two-sided t-test between the two groups of samples.

These miRs can be used to distinguish between mesothelioma and tumors (either primary or metastasis) from colon, kidney, liver, pancreas and stomach. The classification could be done either with a simple threshold (1 or 2 dimension threshold), a logistic regression model or any other classifier.

An exemplified classifier using logistic regression based on two miRs: hsa-miR-200c (SEQ ID NO. 11) and hsa-miR-194 (SEQ ID NO. 4) as detected by microarray is demonstrated in FIG. 4.

The sensitivity of the mesothelioma detection by hsa-miR-200c (SEQ ID NO. 11) and hsa-miR-194 (SEQ ID NO. 4) is 100% and the specificity of the signal is 97%. The p-value of the classifier is 6.4186e-008.

Example 1.3

Figure 5:
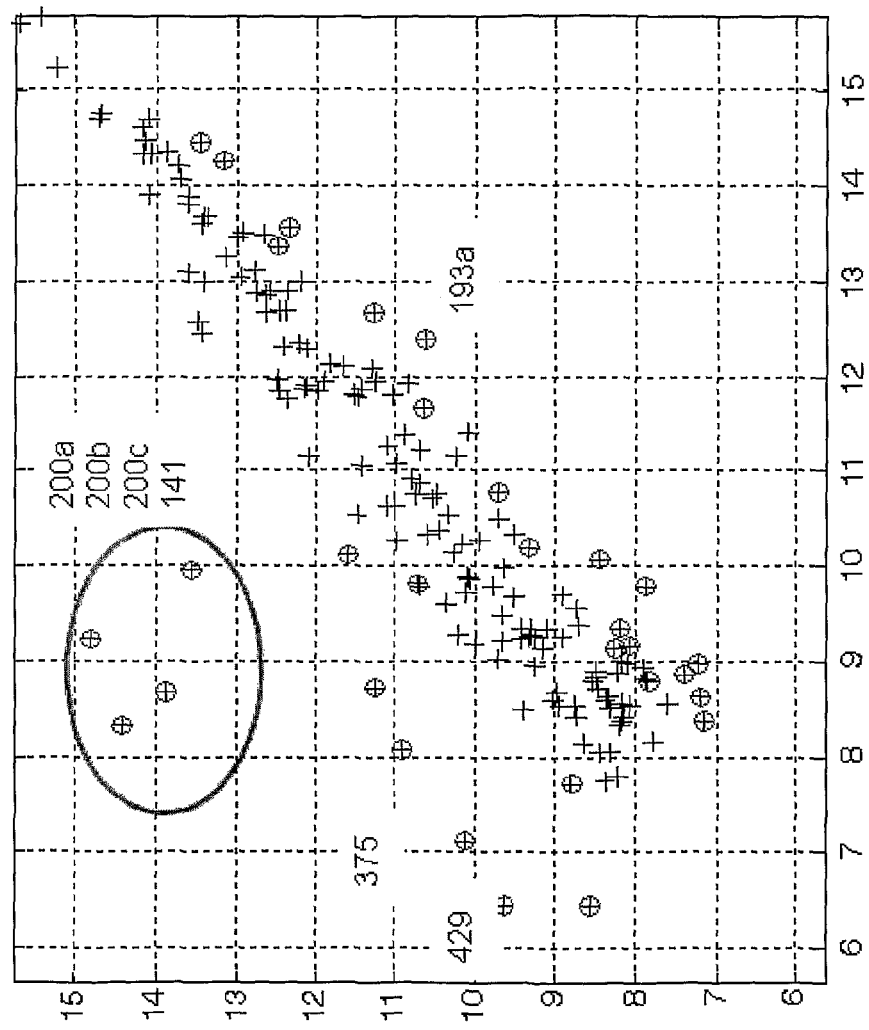
FIG. 5 shows the analysis of the microRNA array results (in log 2(fluorescence)) of lung pleura mesothelioma vs. adenocarcinoma. The x-axis shows the mean normalized expression level of lung pleura mesothelioma samples and the y-axis shows the mean normalized expression level of adenocarcinoma samples of different origins. As shown, miRs with significantly higher expression in lung pleura mesothelioma include hsa-miR-193a (SEQ ID NO. 3), and miRs with higher expression levels in adenocarcinoma include hsa-miR-141 (SEQ ID NO. 1), hsa-miR-200a (SEQ ID NO. 5), hsa-miR-200b (SEQ ID NO. 6), hsa-miR-200c (SEQ ID NO. 11), hsa-miR-375 (SEQ ID NO. 8), and hsa-miR-429 (SEQ ID NO. 9).
Figure 9A:
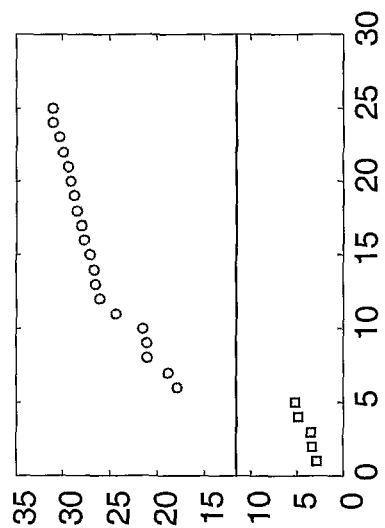
FIG. 9a shows the linear combination of the two miRNAs (y-axis). Samples (x-axis) are sorted according to their linear combination score.
Figure 9B:
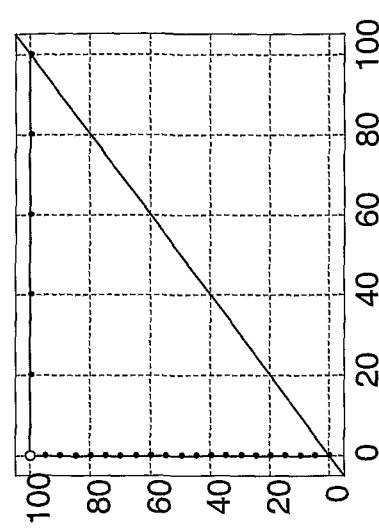
FIG. 9b shows the linear combination of the two miRNAs (y-axis). Samples within each group are sorted separately according to their linear combination score (x-axis).
Figure 9C:
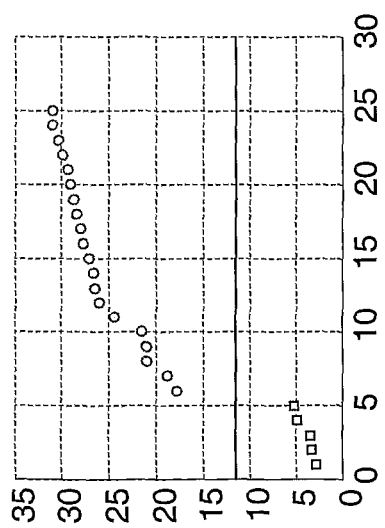
FIG. 9c shows the miRNA normalized Ct of hsa-miR-192 (SEQ ID NO. 2) (x-axis) against the normalized Ct of hsa-miR-122a (SEQ ID NO. 23) (y-axis).
Figure 9D:
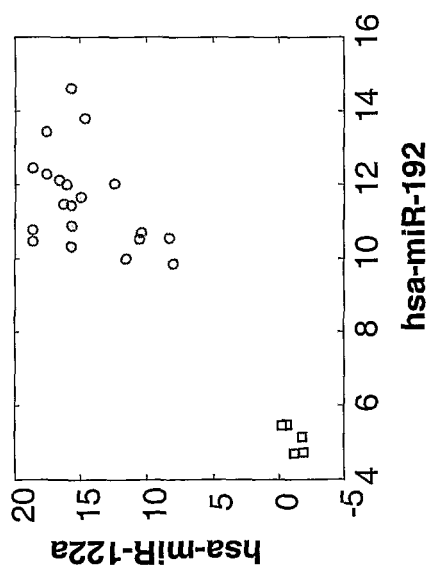
FIG. 9d shows the Area Under the Curve (AUC) of the exemplified classifier, wherein AUC=1. The Y-axis represents the sensitivity and the X-axis represents (1-Specifity).
Figure 11A:
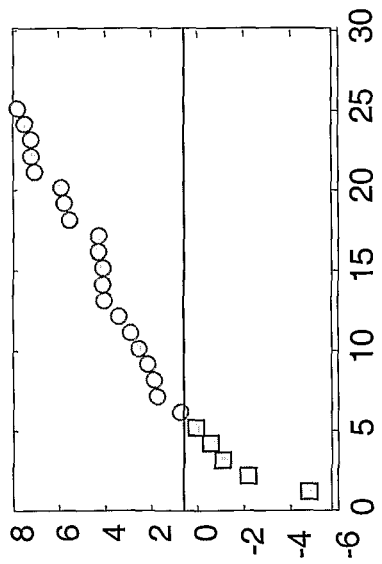
FIG. 11a shows the linear combination of the two miRNAs (y-axis). Samples (x-axis) are sorted according to their linear combination score.
Figure 11B:
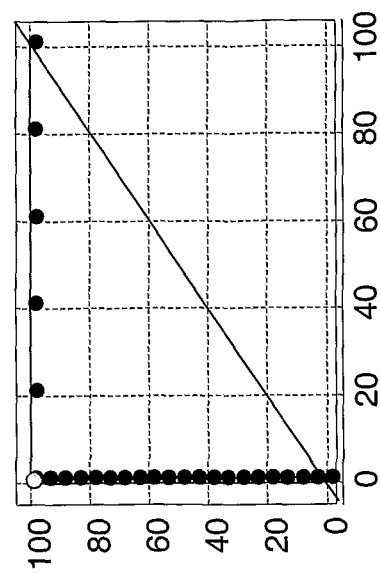
FIG. 11b shows the linear combination of the two miRNAs (y-axis). Samples within each group are sorted separately according to their linear combination score (x-axis).
Figure 11C:
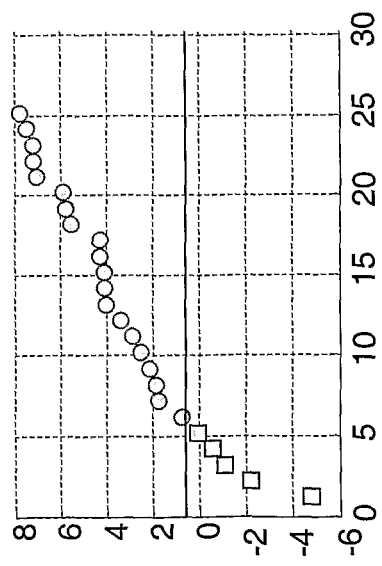
FIG. 11c shows the miRNA normalized Ct of hsa-miR-141 (SEQ ID NO. 1) (x-axis) against the normalized Ct of hsa-miR-193a-3p (SEQ ID NO. 10) (y-axis).
Figure 11D:
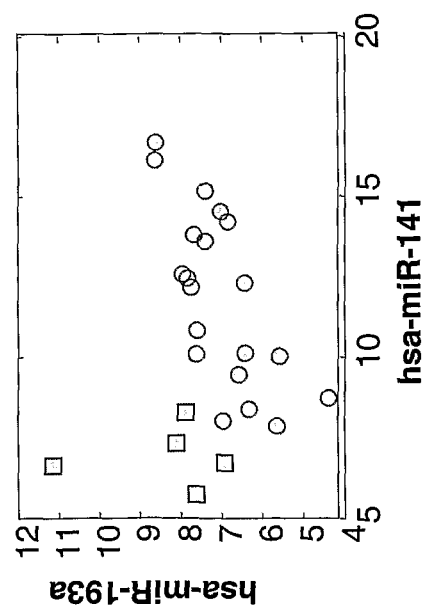
FIG. 11d shows the Area Under the Curve (AUC) of the exemplified classifier, wherein AUC=1. The Y-axis represents the sensitivity and the X-axis represents (1-Specifity).
Figure 12A:
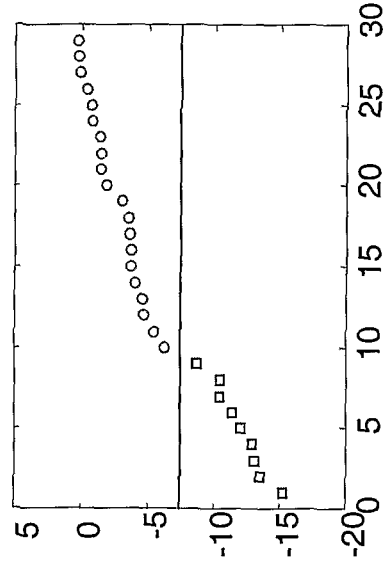
FIG. 12a shows the linear combination of the two miRNAs (y-axis). Samples (x-axis) are sorted according to their linear combination score.
Figure 12B:
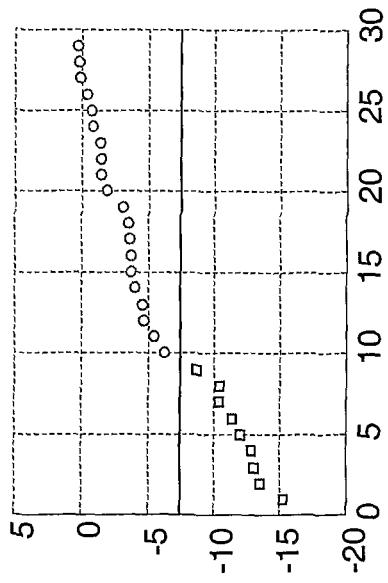
FIG. 12b shows the linear combination of the two miRNAs (y-axis). Samples within each group are sorted separately according to their linear combination score (x-axis).
Figure 12C:
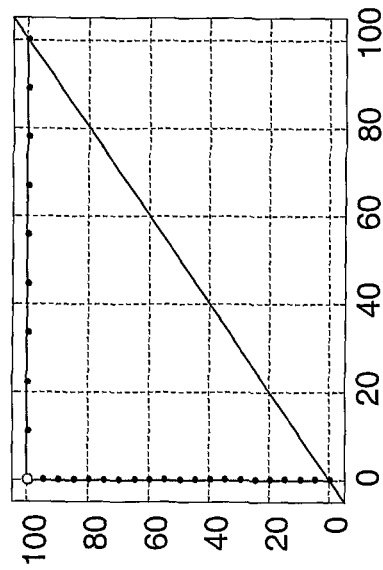
FIG. 12c shows the miRNA normalized Ct of hsa-miR-141 (SEQ ID NO. 1) (x-axis) against the normalized Ct of hsa-miR-193a-3p (SEQ ID NO. 10) (y-axis).
Figure 12D:
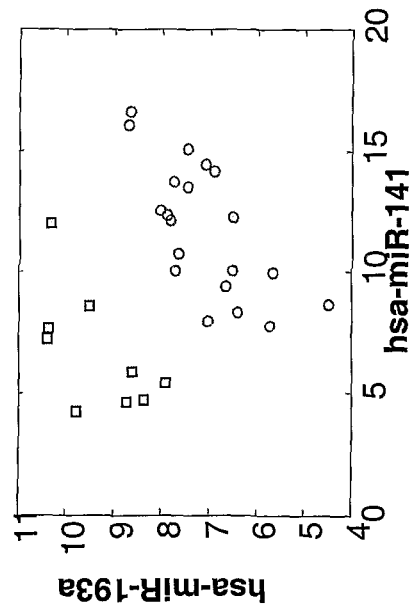
FIG. 12d shows the Area Under the Curve (AUC) of the exemplified classifier, wherein AUC=1. The Y-axis represents the sensitivity and the X-axis represents (1-Specifity).
Figure 13A:
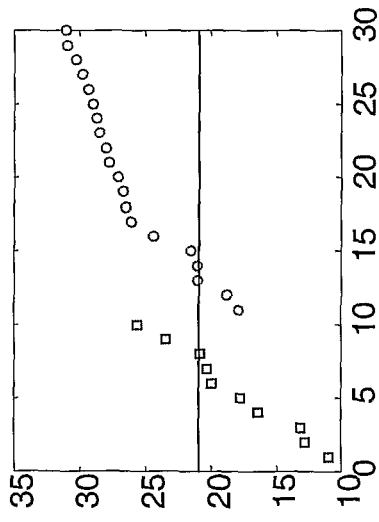
FIG. 13a shows the linear combination of the two miRNAs (y-axis). Samples (x-axis) are sorted according to their linear combination score.
Figure 13B:
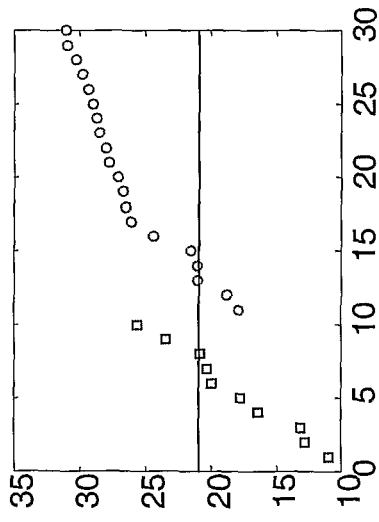
FIG. 13b shows the linear combination of the two miRNAs (y-axis). Samples within each group are sorted separately according to their linear combination score (x-axis).
Figure 13C:
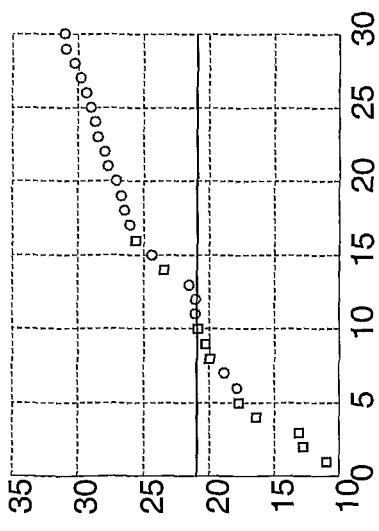
FIG. 13c shows the miRNA normalized Ct of hsa-miR-192 (SEQ ID NO. 2) (x-axis) against the normalized Ct of hsa-miR-122a (SEQ ID NO. 23) (y-axis).
Figure 13D:
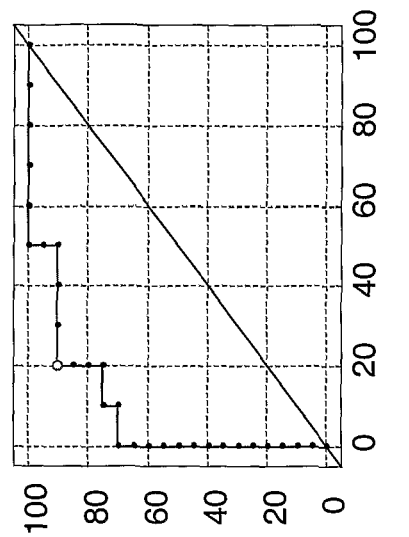
FIG. 13d shows the Area Under the Curve (AUC) of the exemplified classifier, wherein AUC=0.915. The Y-axis represents the sensitivity and the X-axis represents (1-Specifity).

Specific MicroRNAs are Able to Distinguish Between Mesothelioma and Lung Tumors from Different Histological Types The analysis of the arrays results of mesothelioma (seven samples) vs. lung tumors (49 samples) are presented in FIG. 5. The results exhibited a significant difference in the expression pattern of several miRs, as indicated in Table 3.

These miRs can be used to distinguish between mesothelioma and lung tumors (either primary or metastasis). The classification could be done either with a simple threshold (1 or 2 dimension threshold), a logistic regression model or any other classifier.

An exemplified classifier using logistic regression based on two miRs: hsa-miR-200c (SEQ ID NO. 11) and hsa-miR-141 (SEQ ID NO. 1) as detected by microarray is demonstrated in FIG. 6.

The sensitivity of the mesothelioma detection by hsa-miR-200c and hsa-miR-141 is 100% and the specificity of the signal is 98%. The p-value of the classifier is 2.5278e-007.

Another exemplified classifier using logistic regression based on two miRs: hsa-miR-193a (SEQ ID NO. 3) and hsa-miR-200a (SEQ ID NO. 5) as detected by microarray is demonstrated in FIG. 7.

The sensitivity of the mesothelioma detection by hsa-miR-193a and hsa-miR-200a is 100% and the specificity of the signal is 96%. The p-value of the classifier is 3.7521e-007.

TABLE 3

| miR name | MID | HID | p-value |
|---|---|---|---|
| hsa-miR-200a | 5 | 18 | 2.1616e−006 |
| hsa-miR-200b | 6 | 19 | 3.6248e−008 |
| hsa-miR-200c | 11 | 20 | 8.6592e−015 |
| hsa-miR-141 | 1 | 13 | 4.3551e−015 |
| hsa-miR-375 | 8 | 21 | 0.0042 |
| hsa-miR-193a | 3 | 15 | 1.8000e−006 |
| hsa-miR-429 | 9 | 22 | 9.6831e−007 | miR name: is the miRBase registry name (release 9.1).
MID: is the SEQ ID NO of the mature microRNA.
HID: is the SEQ ID NO of the microRNA hairpin precursor (Pre-microRNA).
p-value: is the result of unmatched t-test between samples Example 2 qRT-PCR Assay for Distinguishing Between Mesothelioma and Non-Mesothelioma Tumors from Different Histological Types 2a) Samples Tumor samples were obtained from several sources. Institutional review approvals were obtained for all samples in accordance with each institute's IRB or IRB-equivalent guidelines. For formalin fixed, paraffin-embedded (FFPE) samples, initial diagnosis, histological type, grade and tumor percentages were determined by a pathologist on hematoxilin-eosin (H&E) stained slides, performed on the first and/or last sections of the sample. Clinical records were reviewed for cases of misclassifications.

RNA was extracted from 79 samples of paraffin-embedded (FFPE) tissues originating from the following sources: 20 mesothelioma primary tumor samples in the lung-pleura (2 sarcomatoids, 12 epithelioids and 6 without a known subtype), 20 non-small lung adenocarcinoma primary samples, 10 kidney samples [9 metastases (1 metastasis to the lung pleura and 9 metastases to the lung) and 1 primary tumor], 5 pancreas primaries, 5 colon metastases to the lung, 5 liver primary samples, 5 bladder primary samples, 5 breast metastases to the lung, 4 ovary samples (1 metastasis to the lung-pleura, and 3 primary tumors).

2b) PCR Procedure

A mixture was prepared according to the following:

| Component | Vol/sample |
|---|---|
| 5XE-PAP buffer | 2 µl |
| 25 mM MnCl$_2$ | 1.5 µl |
| 10 mM ATP | 1.5 µl |

-continued

| Component | Vol/sample |
|---|---|
| 1XE-PAP buffer | 0.75 µl |
| Poly A polymerase | 0.25 µl |
| Total Vol | 6 µl |

6 µl of this mixture were added to 4 µl of appropriate RNA sample (or to the ultra pure water of the no RNA control) and incubated for 1 hour at 37° C.

A poly(T) adapter (GCGAGCACAGAATTAATACGACT-CACTATCGGTTTTTTTTTT TTTVN, SEQ ID NO. 42) mixture was prepared according to the following:

| Component | Vol/sample |
|---|---|
| 0.5 µg/µl Poly(T) adapter | 1 µl |
| Ultra pure water | 2 µl |
| Total Vol | 3 µl |

3 µl of this mixture were added to appropriately labeled PCR tubes. 5 µl from the poly-adenylated RNA and No RNA control were transferred to the PCR tubes containing the 3 µl mixture.

The tubes were inserted into a PCR instrument and the annealing process was performed by the following annealing program:

STEP 1: 85° C. for 2 min

STEP 2: 70° C. to 25° C.—decrease of 1° C. in each cycle for 20 sec.

A Reverse Transcription mixture was prepared according to the following:

| Component | Vol/sample |
|---|---|
| 5XRT buffer | 4 µl |
| Trehalose 1.7M | 3 µl |
| 10 mM dNTPs mix | 1 µl |
| DTT (0.1M) | 2 µl |
| Total Vol | 10 µl |

1.5 µl Recombinant Rnasin and 1 µl superscript II RT (per sample) were added to the above mixture. 12.5 µl of the mix were added immediately to each PCR tube containing the annealed PolyA RNA and to the No RNA control.

The tubes were placed immediately in a thermocycler and the following reverse transcription program was performed:

STEP 1: 37° C. for 5 min

STEP 2: 45° C. for 5 min

STEP 3: Repeat steps 1-2, 5 times

STEP 4: End the program at 4° C.

A primer-probe mix was prepared. In each tube 10 µM Fwd primer was mixed with the same volume of 5 µM of the corresponding MGB probe, specific for the same RNA.

The sequences of the Fwd primers and MGB probes are indicated in Table 4.

TABLE 4

Sequences of primers and probes

| Name | Fwd (Forward miR specific) primer | SEQ ID NO | MGB probe | SEQ ID NO |
|---|---|---|---|---|
| miR-122 | CAGTCATTTGGGTGG AGTGTGACAATGG | 27 | CCGTTTTTTTTTTTA AACACCA | 28 |
| miR-192 | CAGTCATTTGGGCTG ACCTATGAATTGA | 29 | CGTTTTTTTTTTTGG CTGTCA | 30 |
| miR-193a-3p | CAGTCATTTGGGAAC TGGCCTACAAAGT | 31 | CCGTTTTTTTTTTTA CTGGGAC | 32 |
| miR-141 | CAGTCATTTGGGTAA CACTGTCTGGTAA | 33 | CCGTTTTTTTTTTTG CCATCTT | 34 |
| miR-122a | CAGTCATTTGGGTGG AGTGTGACAATGG | 35 | CCGTTTTTTTTTTTA CAAACAC | 36 |
| miR-200c | CAGTCATTTGGGTAA TACTGCCGGGTAA | 37 | CGTTTTTTTTTTTCC ATCATT | 38 |
| *miR-141 | CAGTCATTTGGGTAA CACTGTCTGGTAA | 33 | CGTTTTTTTTTTTCC ATCTTT | 43 |
| U6 | GCAAGGATGACACG CAAATTC | 39 | AATATGGAACGCTTC ACG | 40 |

*as cloned at Rosetta Genomics

The cDNA was diluted to a final concentration of 0.5 ng/μl. The PCR mixture according to the following:

| Component | Vol/sample |
|---|---|
| 2 X TaqMan Universal PCR | 10 μl |
| RT-rev-primer-race 10 μM | 1 μl |
| Ultra pure water | 6 μl |
| Total Vol | 17 μl |

119 μl (for No RNA control and for No cDNA control) or 289 μl of the PCR mix were dispense into the appropriately labeled Microtubes. 17 μl cDNA (0.5 ng/μl) were dispensed into the Microtubes containing the mix. The PCR plate was prepared by dispensing 18 μl from the mix into each well using a repeater pipette. 2 μl primer probe mixture was added into each well using a multi-channel pipettor. The plates were put in the PCR instrument and the following program was performed:

Stage 1, Reps=1

STEP 1: Hold @ 95.0 for 10 min (MM:SS), Ramp Rate=100

Stage 2, Reps=40

STEP 1: Hold @ 95.0 for 0:15 (MM:SS), Ramp Rate=100

STEP 2: Hold @ 60.0 for 1:00 (MM:SS), Ramp Rate=100

Standard 7500 Mode

Sample Volume (μL): 20.0

Data Collection Stage 2, Step 2

2c) Processing of Expression Levels Detected by qRT-PCR

The expression levels of the desired nucleic acids were detected by quantitative RT-PCR as described above. PCR Ct signals represent the first cycle where amplification crosses a threshold of fluorescence. Low values of CT represent high abundance or expression levels of the microRNA.

Ct of negative control wells was underdetermined.

The results were processed by one of the following outlines:

A. The weighted Ct of the 3 repeats was calculated as the median of the triplicate. For a median of 32 Cts or less, outliers up to 1 Ct are allowed. For medians above 32 and below 37 Cts, outliers up to 1.5 Cts are allowed. For medians of 37 Cts or more, outliers up to 2 Cts are allowed. If a triplicate had two outliers according to the above definition, it was discarded.

B. The weighted Ct of the 3 repeats was calculated according to the following: If all repeats were within 1 Ct difference, meaning that the difference between the minimal and maximal Cts was less than 1, then their average was calculated as follows:

$Ct\text{max} - Ct\text{min} \leq 1 \rightarrow \text{weighted } Ct = (Ct\text{max} + Ct\text{median} + Ct\text{min})/3$ If each of the outlier Cts has less than 1 Ct difference from the middle value (or equal to 1 Ct) their average was calculated.

Ctmax−Ctmedian≤1 and Ctmedian−Ctmin≤1 → weighted Ct=(Ctmax+ Ctmedian+ Ctmin)/3. If one of the outlier Cts has more than 1 Ct difference from the median Ct—it is not used in the weighted Ct.

Interpretation of the data was according to the following criteria:

U6 should have a weighted Ct between 20 and 32. If not, the experiment failed.

Throughout example 2 the PCR signal (Ct) was normalized for each sample by subtracting the weighted Ct of U6 for this sample from the weighted Ct of each microRNA for this sample. Thus the normalized Ct remains inverse from the expression level, such that low values of normalized Ct represent high abundance or expression levels of the microRNA.

Example 2.1

Specific MicroRNAs are Able to Distinguish Between Lung Pleura Mesothelioma and Lung Adenocarcinoma An exemplified classifier using a linear combination based on two miRs: hsa-miR-141 (SEQ ID NO. 1) and hsa-miR-193a-3p (SEQ ID NO. 10) as detected by PCR is demonstrated in FIG. 8. The sensitivity of the detection is 100% and the specificity of the signal is 100%.

Example 2.2

Specific MicroRNAs are Able to Distinguish Between Lung Pleura Mesothelioma and Liver Tumors An exemplified classifier using a linear combination based on two miRs: hsa-miR-192 (SEQ ID NO. 2) and hsa-miR-122a (SEQ ID NO. 23) as detected by PCR is demonstrated in FIG. 9. The sensitivity of the detection is 100% and the specificity of the signal is 100%.

Example 2.3

Specific MicroRNAs are Able to Distinguish Between Lung Pleura Mesothelioma and Tumors from Either the Colon or Pancreas An exemplified classifier using a linear combination based on two miRs: hsa-miR-192 (SEQ ID NO. 2) and hsa-miR- 193a-3p (SEQ ID NO. 10) as detected by PCR is demonstrated in FIG. 10. The sensitivity of the detection is 100% and the specificity of the signal is 100%.

Example 2.4

Specific MicroRNAs are Able to Distinguish Between Lung Pleura Mesothelioma and Bladder Tumors An exemplified classifier using a linear combination based on two miRs: hsa-miR-141 (SEQ ID NO. 1) and hsa-miR-193a-3p (SEQ ID NO. 10) as detected by PCR is demonstrated in FIG. 11. The sensitivity of the detection is 100% and the specificity of the signal is 100%.

Example 2.5

Specific MicroRNAs are Able to Distinguish Between Lung Pleura Mesothelioma and Ovary and Breast Tumors An exemplified classifier using a linear combination based on two miRs: hsa-miR-141 (SEQ ID NO. 1) and hsa-miR-193a-3p (SEQ ID NO. 10) as detected by PCR is demonstrated in FIG. 12. The sensitivity of the detection is 100% and the specificity of the signal is 100%.

Example 2.6

Specific MicroRNAs are Able to Distinguish Between Lung Pleura Mesothelioma and Kidney Tumors An exemplified classifier using a linear combination based on two miRs: hsa-miR-192 (SEQ ID NO. 2) and hsa-miR-122a (SEQ ID NO. 23) as detected by PCR is demonstrated in FIG. 13. The sensitivity of the detection is 90% and the specificity of the signal is 80%, with 4 errors.

Example 2.7

Establishment of qRT-PCR Assays for Distinguishing Between Mesothelioma and Non-Mesothelioma Tumors from Different Histological Types 2.7.1) Assay #1

The expression levels of hsa-miR-192 (SEQ ID NO. 2), hsa-miR-200c (SEQ ID NO. 11) hsa-miR-193a-3p (SEQ ID NO. 10) and U6 (SEQ ID NO. 41) were measured according to the PCR procedure described in example 2b above.

Using the calculated weighted Ct, the final score for the assay was determined by subtracting the weighted Ct of U6 from each of the weighted Cts calculated for each of the 3 miRs:

NormCt(miR-192)=(weightedCt(miR-192)−weightedCt(U6);

NormCt(miR-193a-3p)=weightedCt(miR-193a-3p)−weightedCt(U6);

NormCt(miR-200c)=weightedCt(miR-200c)−weightedCt(U6);

The analysis of the results of the qRT-PCR assay is performed in two steps:

Step 1: The normalized Cts of hsa-miR-192 (SEQ ID NO. 2) (NormCt(hsa-miR-192)) was compared to a threshold value, as demonstrated in table 5.

Low scoring samples were determined as Non-mesotheliomas;

The rest of the samples continued to the Step 2.

Step 2: A linear combination of the normalized Cts of hsa-miR-200c (SEQ ID NO. 11) and hsa-miR-193a-3p (SEQ ID NO. 10) was calculated and compared to a threshold, as demonstrated in table 5.

The calculations and assay results are demonstrated in table 5.

TABLE 5

| | Step 1 | | | |
| --- | --- | --- | --- | --- |
| Step 2 | M1 > 10 | 8.5 < M1 < 10 | 7 < M1 < 8.5 | M1 < 7 |
| M2 > −4.5 | Meso HC | Meso LC | Non-meso LC | Non-meso HC |
| −6 < M2 < −4.5 | Meso LC | Meso LC | Non-meso LC | Non-meso HC |
| −7.5 < M2 < −6 | Non-meso LC | Non-meso LC | Non-meso LC | Non-meso HC |
| M2 < −7.5 | Non-meso HC | Non-meso HC | Non-meso HC | Non-meso HC |

M1 = NormCt(miR-192);
M2 = NormCt(miR-200c) − 1.5 * NormCt(miR-193a-3p)
LC = Low confidence
HC = High confidence The sensitivity of the mesothelioma detection by hsa-miR-192 (SEQ ID NO. 2), hsa-miR-200c (SEQ ID NO. 11) and hsa-miR-193a-3p (SEQ ID NO. 10) is 95% (19/20) and the specificity is 93% (55/59). The accuracy of the detection for each of the non-mesothelioma cancers is indicated in table 6:

TABLE 6

| | Mesothelioma | Non-mesothelioma | Accuracy |
| --- | --- | --- | --- |
| Mesothelioma (20 samples) | 19 | 1 | 95 |
| Lung (20 samples) | 1 | 19 | 95 |
| Ovary (4 samples) | 0 | 4 | 100 |
| Breast (5 samples) | 0 | 5 | 100 |
| Bladder (5 samples) | 0 | 5 | 100 |
| Liver (5 samples) | 0 | 5 | 100 |
| Colon (5 samples) | 0 | 5 | 100 |
| Pancreas (5 samples) | 0 | 5 | 100 |
| Kidney (10 samples) | 3 | 7 | 70 |

2.7.1) Assay #2

The expression levels of hsa-miR-192 (SEQ ID NO.2), hsa-miR-122 (SEQ ID NO. 24) hsa-miR-200c (SEQ ID NO. 11) hsa-miR-193a-3p (SEQ ID NO. 10) and U6 (SEQ ID NO. 41) were measured according to the PCR procedure described in example 2b above.

Using the calculated weighted Ct, the final score for the assay was determined by subtracting the weighted Ct of U6 from each of the weighted Cts calculated for each of the 4 miRs:

NormCt(miR-192)=(weightedCt(miR-192)−weightedCt(U6);

NormCt(miR-122)=weightedCt(miR-122)−weightedCt(U6);

NormCt(miR-193a-3p)=weightedCt(miR-193a-3p)+ weightedCt(U6);

NormCt(miR-200c)=weightedCt(miR-200c)−weightedCt(U6);

The analysis of the results of the qRT-PCR assay is performed in two steps:
Step 1: The normalized Cts of hsa-miR-192 (SEQ ID NO. 2) and hsa-miR-122 (SEQ ID NO. 24) (NormCt(hsa-miR-192), NormCt(hsa-miR-122)) were compared to threshold values, as demonstrated in table 7.

Low scoring samples were determined as Non-mesotheliomas;

The rest of the samples continued to the Step 2.

Step 2: A linear combination of the normalized Cts of hsa-miR-200c (SEQ ID NO. 11) and hsa-miR-193a-3p (SEQ ID NO. 10) was calculated and compared to a threshold, as demonstrated in table 7.

The calculations and assay results are demonstrated in table 7.

NormCt(miR-192)=(weightedCt(miR-192)−weightedCt(U6);

NormCt(miR-122)=weightedCt(miR-122)−weightedCt(U6);

NormCt(miR-141)=weightedCt(miR-141)−weightedCt(U6);

NormCt(miR-193a-3p)=weightedCt(miR-193a-3p)−weightedCt(U6);

The analysis of the results of the qRT-PCR assay is performed in two steps:
Step I: The normalized average Cts of hsa-mir-192 and hsa-miR-122 were added: Normalized weighted Ct(miR-192)+ Normalized weighted Ct(miR-122).

Low scoring samples were determined as Non-mesotheliomas;

TABLE 7

| | Step 1 | | | |
|---|---|---|---|---|
| Step 2 | M1 > 10 AND M2 > 8.5 | (8.5 < M1 < 10 AND M2 > 7) OR (7 < M2 < 8.5 AND M1 > 8.5) | (7 < M1 < 8.5 AND M2 > 5.5) OR (5.5 < M2 < 7 AND M1 > 7) | M1 < 7 OR M2 < 5.5 |
| M3 > −4.5 | Meso HC | Meso LC | Non-meso LC | Non-meso HC |
| −6 < M3 < −4.5 | Meso LC | Meso LC | Non-meso LC | Non-meso HC |
| −7.5 < M3 < −6 | Non-meso LC | Non-meso LC | Non-meso LC | Non-meso HC |
| M3 < −7.5 | Non-meso HC | Non-meso HC | Non-meso HC | Non-meso HC |

Figure 14:
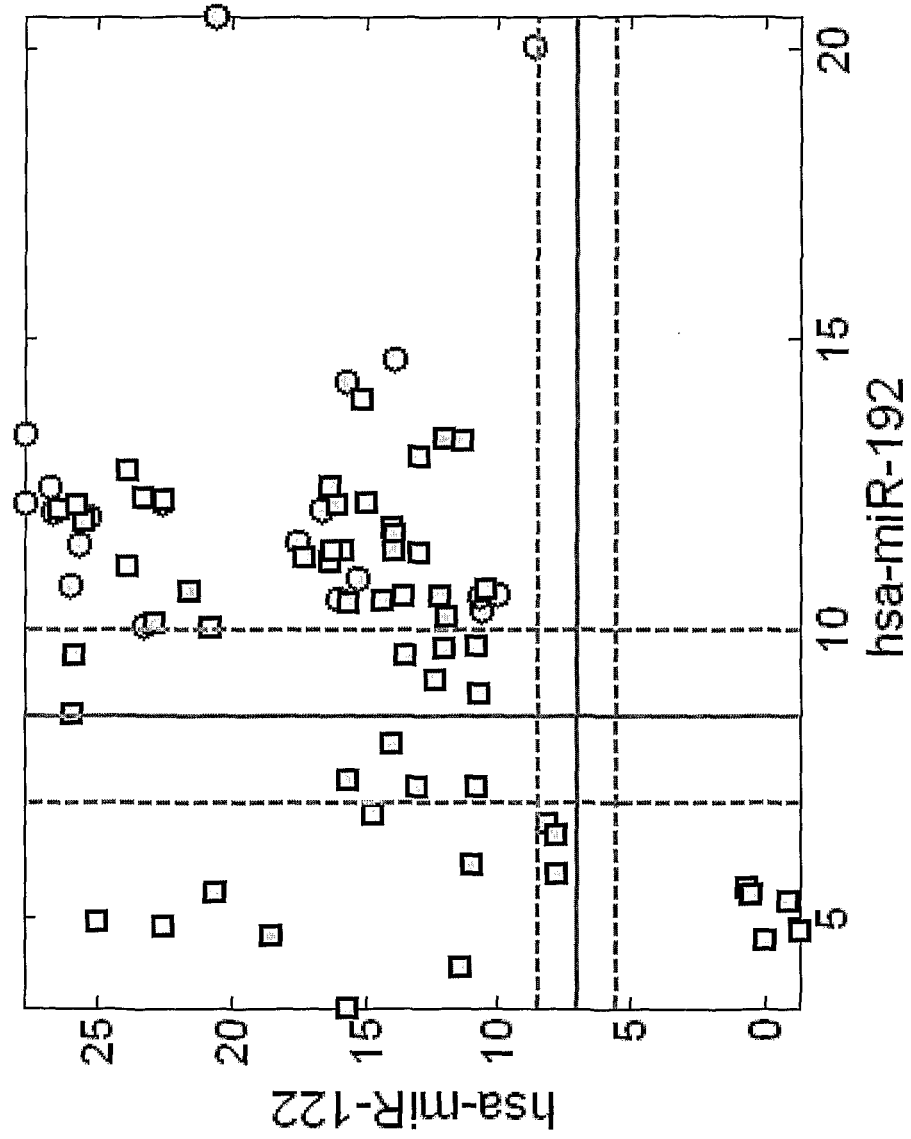
FIGS. 14 and 15 demonstrate a two step exemplified classifier used to distinguish between lung pleura mesothelioma samples (circles) and tumor samples of the following types: liver, kidney, pancreas, colon, bladder, ovary, breast and lung (squares).
Figure 15:
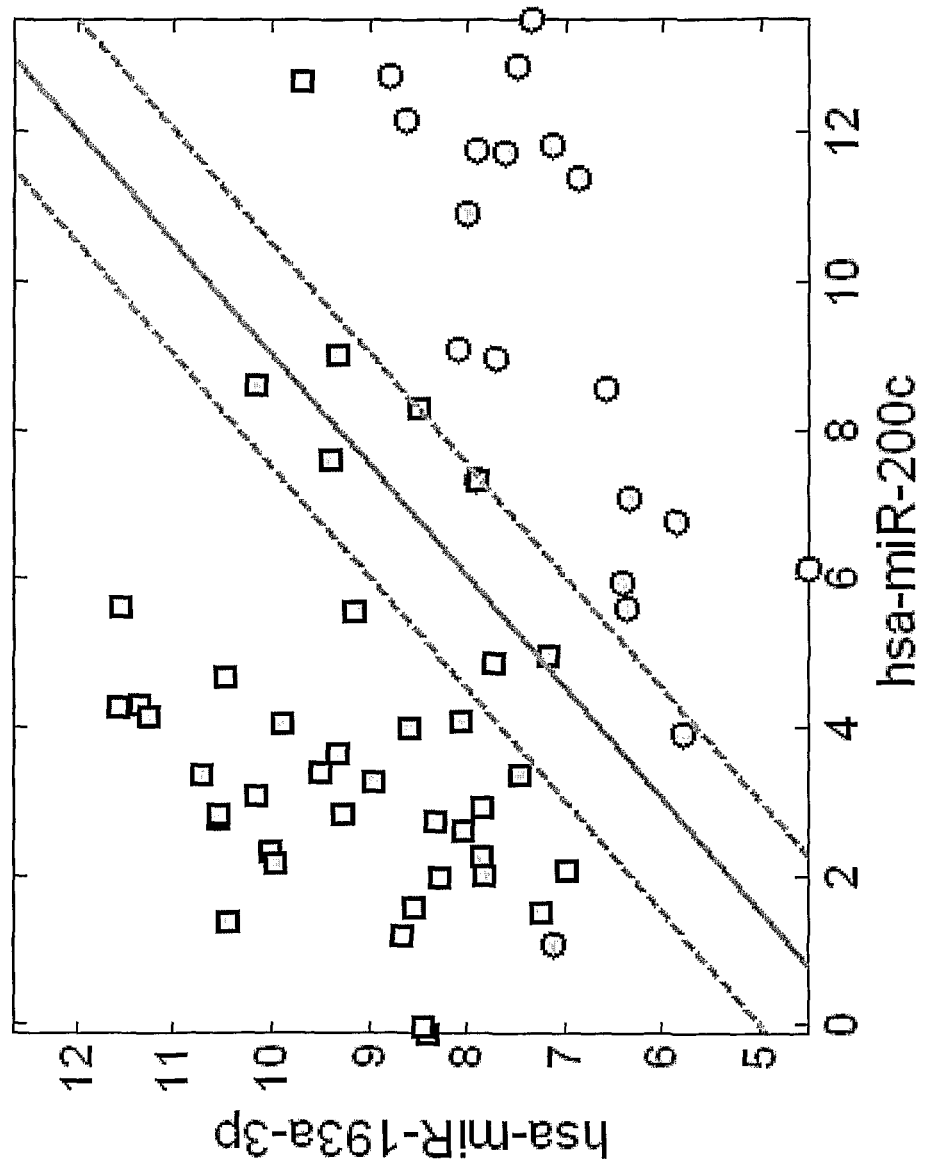
Figure 16A:
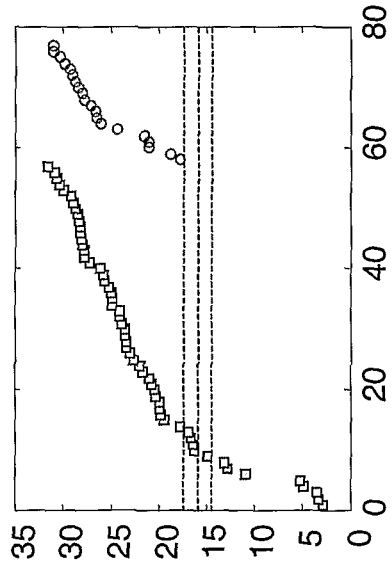
FIG. 16a shows the linear combination of the two miRNAs (y-axis). Samples (x-axis) are sorted according to their linear combination score.
Figure 16B:
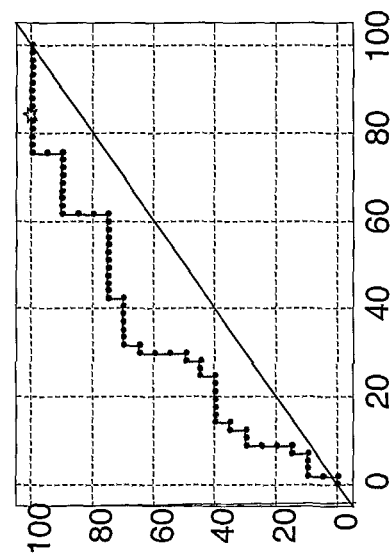
FIG. 16b shows the linear combination of the two miRNAs (y-axis). Samples within each group are sorted separately according to their linear combination score (x-axis). Sensitivity: 100%, Specificity: 16%.
Figure 16C:
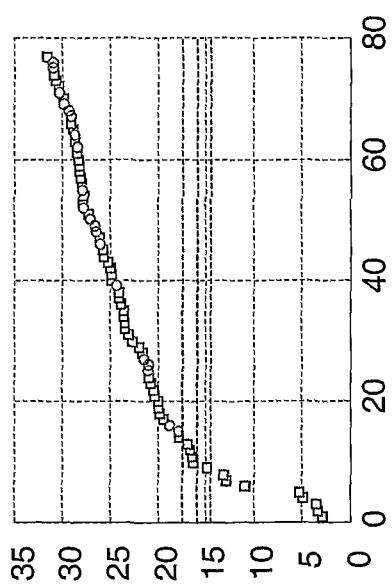
FIG. 16c shows the normalized Ct of hsa-miR-192 (SEQ ID NO. 2) (x-axis) against the normalized Ct of hsa-miR-122a (SEQ ID NO. 23) (y-axis).
Figure 16D:
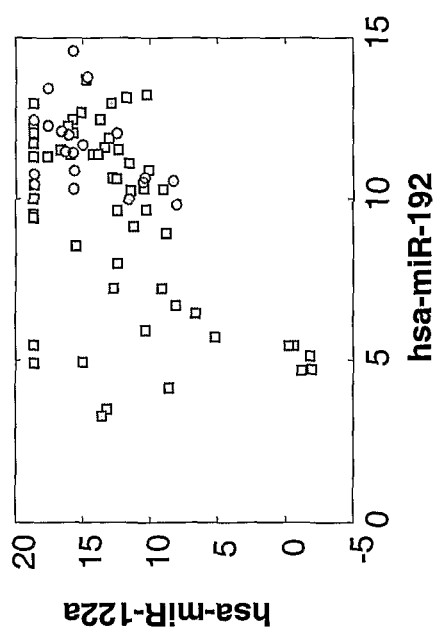
FIG. 16d shows the Area Under the Curve (AUC) of the exemplified classifier, wherein AUC=0.69298. The Y-axis represents the sensitivity and the X-axis represents (1-Specifity).

M1 = NormCt(miR-192);
M2 = NormCt(miR-122);
M3 = NormCt(miR-200c) − 1.5 * NormCt(miR-193a-3p)
LC = Low confidence
HC = High confidence FIG. 14 demonstrates the first step of the classifier of assay #2, using hsa-miR-192 (SEQ ID NO. 2) and hsa-miR-122a (SEQ ID NO. 23) on 79 samples. Samples that scored low on the combination of the two miRNAs were identified as "non-mesothelioma". The remaining samples continued to the next step. The second step of the classifier is demonstrated in FIG. 15.

The sensitivity of the mesothelioma detection by hsa-miR-192 (SEQ ID NO. 2), hsa-miR-122 (SEQ ID NO. 24) hsa-miR-200c (SEQ ID NO. 11) and hsa-miR-193a-3p (SEQ ID NO. 10) is 95% (19/20) and the specificity is 93% (55/59). The accuracy of the detection for each of the non-mesothelioma cancers is indicated in table 6 above.

2.7.2) Assay #3

The expression levels of hsa-miR-192 (SEQ ID NO. 2), hsa-miR-122 (SEQ ID NO. 24) hsa-miR-141 (SEQ ID NO. 1) hsa-miR-193a-3p (SEQ ID NO. 10) and U6 (SEQ ID NO. 41) according to the PCR procedure described in example 2b above.

Using the calculated weighted Ct, the final score for the assay was determined by subtracting the weighted Ct of U6 from each of the weighted Cts calculated for each of the 4 miRs:

High scoring samples were analyzed according to table 8:

TABLE 8

| Normalized weighted Ct(miR-192) + Normalized weighted Ct(miR-122) | Step result |
|---|---|
| >=17.4 | Continue to step II |
| >15.9 and <17.4 | Continue to step II, Low confidence |
| <=14.4 | Non-mesothelioma |
| <=15.9 and >14.4 | Non-mesothelioma, Low confidence |

Step II: The normalized weighted Ct(miR-193a-3p) was subtracted from the normalized weighted Ct(miR-141): Normalized weighted Ct(miR-141)−Normalized weighted Ct(miR-193a-3p).

Low scoring samples were determined non-mesotheliomas;

High scoring samples were determined mesotheliomas, according to table 9:

TABLE 9

| Normalized weighted Ct(miR-141) − Normalized weighted Ct(miR-193a-3p) | Step result |
|---|---|
| >=3.3 | Mesothelioma, High confidence |
| >1.8 and <3.3 | Mesothelioma, Low confidence |
| <=0.3 | Non-mesothelioma, High confidence |
| <=1.8 and >0.3 | Non-mesothelioma, Low confidence |

The first and second steps of the classifier of this assay are further demonstrated in FIGS. 16 and 17 respectively.

The sensitivity of the mesothelioma detection by hsa-miR-192 (SEQ ID NO. 2), hsa-miR-122 (SEQ ID NO. 24) hsa-miR-141 (SEQ ID NO. 1) and hsa-miR-193a-3p (SEQ ID NO. 10) is 95% (19/20) and the specificity is 98% (58/59). The accuracy of the detection for each of the non-mesothelioma cancers is indicated in table 10:

TABLE 10

|  | Mesothelioma | Non-mesothelioma | Accuracy (%) |
|---|---|---|---|
| Mesothelioma (20 samples) | 19 | 1 | 95 |
| Lung adenocarcinoma (20 samples) | 0 | 20 | 100 |
| Kidney (10 samples) | 1 | 9 | 90 |
| breast (5 samples) | 0 | 5 | 100 |
| ovary (4 samples) | 0 | 4 | 100 |
| liver (5 samples) | 0 | 5 | 100 |
| bladder (5 samples) | 0 | 5 | 100 |
| pancreas (5 samples) | 0 | 5 | 100 |
| colon (5 samples) | 0 | 5 | 100 |

Example 3

MicroRNAs Serve as Molecular Markers for Identification of Mesothelioma (MPM) from Adenocarcinomas and Renal Cell Carcinomas (RCC)

104 archival formalin-fixed, paraffin-embedded (FFPE) cancer samples, including 7 MPM samples from the lung pleura, 16 RCC samples, and 81 adenocarcinomas from the colon (n=17), lung (n=15), ovary (n=10), esophagus (n=11), endometrium (n=9), stomach (n=6), pancreas (n=6), breast (n=4) and prostate (n=3), were profiled by use of microRNA micro arrays.

Table 11 presents median values of normalized fluorescence in malignant pleural mesothelioma (MPM), adenocarcinoma, and RCC samples for microRNAs that were differentially expressed between mesothelioma and either adenocarcinoma or RCC. A Benjamini-Hochberg False Discovery Rate of 0.2 was used to identify differentially expressed microRNAs, resulting in p-value cutoffs of 0.05 and 0.04 respectively. For each of the two comparisons, values are shown for p-value (two-sided unpaired t-test), fold-change of median expression (either up-regulated or down-regulated, as is indicated by the median values), and AUC which is the area under the Receiver Operating Characteristic (ROC) curve, indicative of the classification potential of each microRNA. MicroRNAs are sorted by decreasing values of the sum of the AUC of the two comparisons.

TABLE 11

MicroRNAs differentially expressed between malignant pleural mesothelioma (MPM) and adenocarcinoma (Adeno) or renal cell carcinoma (RCC)

|  |  | Median values | | | MPM vs. Adeno | | | MPM vs. RCC | | |
|---|---|---|---|---|---|---|---|---|---|---|
| miR name | SEQ ID NO. | MPM | Adeno | RCC | p-value | fold-change | AUC | p-value | fold-change | AUC |
| hsa-miR-200b | 6 | 550 | 21000 | 5000 | 2.0E−16 | 38.4 | 0.98 | 7.0E−05 | 9.2 | 0.92 |
| hsa-miR-200a | 5 | 880 | 15000 | 4400 | 6.7E−12 | 16.8 | 0.98 | 4.6E−04 | 5.0 | 0.89 |
| hsa-miR-429 | 9 | 73 | 980 | 200 | 2.7E−09 | 13.3 | 0.97 | 4.7E−03 | 2.7 | 0.86 |
| hsa-miR-194 | 4 | 280 | 1900 | 2400 | 7.9E−03 | 6.8 | 0.81 | 3.3E−04 | 8.6 | 0.94 |
| hsa-miR-200c | 11 | 590 | 30000 | 1500 | 2.6E−20 | 50.3 | 0.99 | 5.2E−02 | 2.5 | 0.75 |
| hsa-miR-141 | 1 | 260 | 25000 | 990 | 2.9E−20 | 96.6 | 0.99 | 6.7E−02 | 3.8 | 0.75 |
| hsa-miR-193a-3p | 10 | 6100 | 1500 | 3000 | 3.9E−05 | 4.2 | 0.91 | 6.3E−03 | 2.1 | 0.80 |
| hsa-miR-192 | 2 | 410 | 1800 | 3000 | 1.8E−02 | 4.5 | 0.76 | 1.1E−03 | 7.4 | 0.91 |
| hsa-miR-143 | 58 | 7400 | 13000 | 17000 | 4.8E−02 | 1.8 | 0.74 | 1.6E−03 | 2.3 | 0.92 |
| hsa-miR-221 | 59 | 19000 | 12000 | 7800 | 3.9E−03 | 1.6 | 0.79 | 5.2E−03 | 2.5 | 0.88 |
| hsa-miR-30d | 60 | 8800 | 12000 | 20000 | 1.1E−01 | 1.4 | 0.67 | 1.3E−04 | 2.2 | 0.94 |
| hsa-miR-193b | 61 | 4300 | 1500 | 2500 | 2.1E−03 | 2.9 | 0.85 | 1.2E−01 | 1.7 | 0.72 |
| hsa-miR-494 | 62 | 3100 | 1600 | 1300 | 2.8E−02 | 2.0 | 0.76 | 1.2E−02 | 2.4 | 0.80 |
| hsa-miR-193a-5p | 63 | 2000 | 380 | 540 | 2.5E−05 | 5.3 | 0.83 | 6.8E−02 | 3.7 | 0.73 |
| hsa-miR-152 | 64 | 2200 | 910 | 1600 | 3.5E−03 | 2.4 | 0.89 | 2.9E−01 | 1.4 | 0.64 |
| hsa-miR-30a | 65 | 7400 | 6100 | 16000 | 4.6E−01 | 1.2 | 0.58 | 5.4E−04 | 2.2 | 0.93 |
| hsa-miR-210 | 66 | 5900 | 4000 | 13000 | 2.9E−01 | 1.5 | 0.61 | 3.0E−03 | 2.2 | 0.88 |
| hsa-miR-497 | 67 | 1300 | 2600 | 5500 | 2.1E−01 | 2.0 | 0.64 | 9.0E−03 | 4.3 | 0.85 |
| hsa-miR-130a | 68 | 10000 | 3500 | 5200 | 4.7E−02 | 2.9 | 0.73 | 9.2E−02 | 1.9 | 0.75 |
| hsa-miR-375 | 8 | 120 | 960 | 82 | 7.0E−03 | 7.8 | 0.82 | 4.4E−01 | 1.5 | 0.63 |
| hsa-miR-486-5p | 69 | 500 | 590 | 1600 | 4.3E−01 | 1.2 | 0.56 | 4.2E−03 | 3.2 | 0.84 |
| hsa-miR-126 | 70 | 4300 | 5100 | 15000 | 7.8E−01 | 1.2 | 0.49 | 3.7E−03 | 3.5 | 0.87 |
| hsa-miR-10b | 71 | 350 | 300 | 1200 | 8.3E−01 | 1.2 | 0.50 | 2.3E−02 | 3.4 | 0.85 |
| hsa-miR-451 | 72 | 1300 | 1200 | 2900 | 8.1E−01 | 1.1 | 0.51 | 2.7E−02 | 2.2 | 0.80 |

Figure 18A:
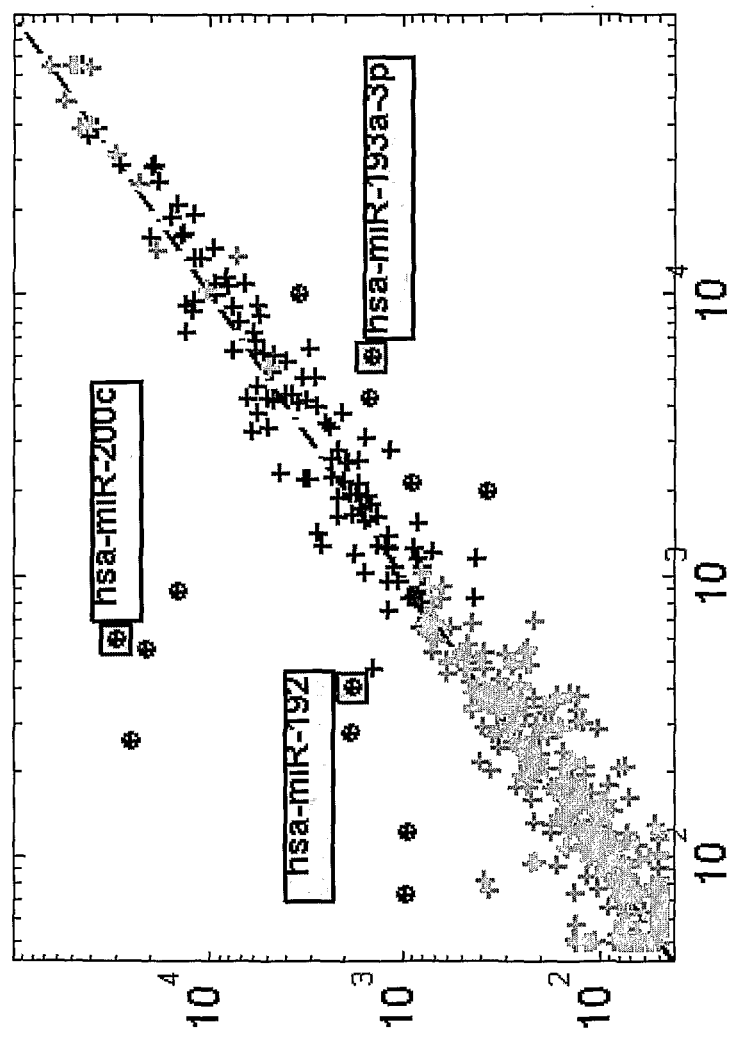
FIG. 18 shows a comparison of microRNA expression levels in malignant pleural mesothelioma (MPM), adenocarcinoma, and renal cell carcinoma (RCC). Median normalized-inverted fluorescence values of each microRNA in 7 MPM samples are plotted (X-Axis) against the median fluorescence values of these microRNAs in 81 adenocarcinoma samples (Y-axis of FIG. 18A) and in 16 RCC samples (Y-axis of FIG. 18B). Light crosses show control probes and microRNAs whose expression level was at background levels (median signal<800) in both groups. MicroRNAs that had signal above the background level in at least one group (dark crosses) were tested for statistical differences by two-sided unpaired t-test. Circles mark microRNAs that had statistically significant differences in expression values at a False Discovery Rate (FDR) of 0.2 (p-values lower than 0.05 and 0.04 respectively). Squares highlight the expression levels of hsa-miR-200c (SEQ ID NO. 11), hsa-miR-192 (SEQ ID NO. 2), and hsa-miR-193a-3p (SEQ ID NO. 10).
FIG. 18C shows box-plots of the expression levels of hsa-miR-200c (SEQ ID NO. 11), hsa-miR-192 (SEQ ID NO. 2), and hsa-miR-193a-3p (SEQ ID NO. 10) in MPM, adenocarcinoma, and RCC samples, showing the median (horizontal line), 25 to 75 percentile (box), and extent of data ("whiskers"). Units show log 2 of the normalized fluorescence signal by microarray.
FIG. 18D shows box-plots of the expression levels (normalized Ct) of these microRNAs in 22 MPM samples, 39 adenocarcinoma samples, and 4 RCC samples measured by qRT-PCR.
Figure 18B:
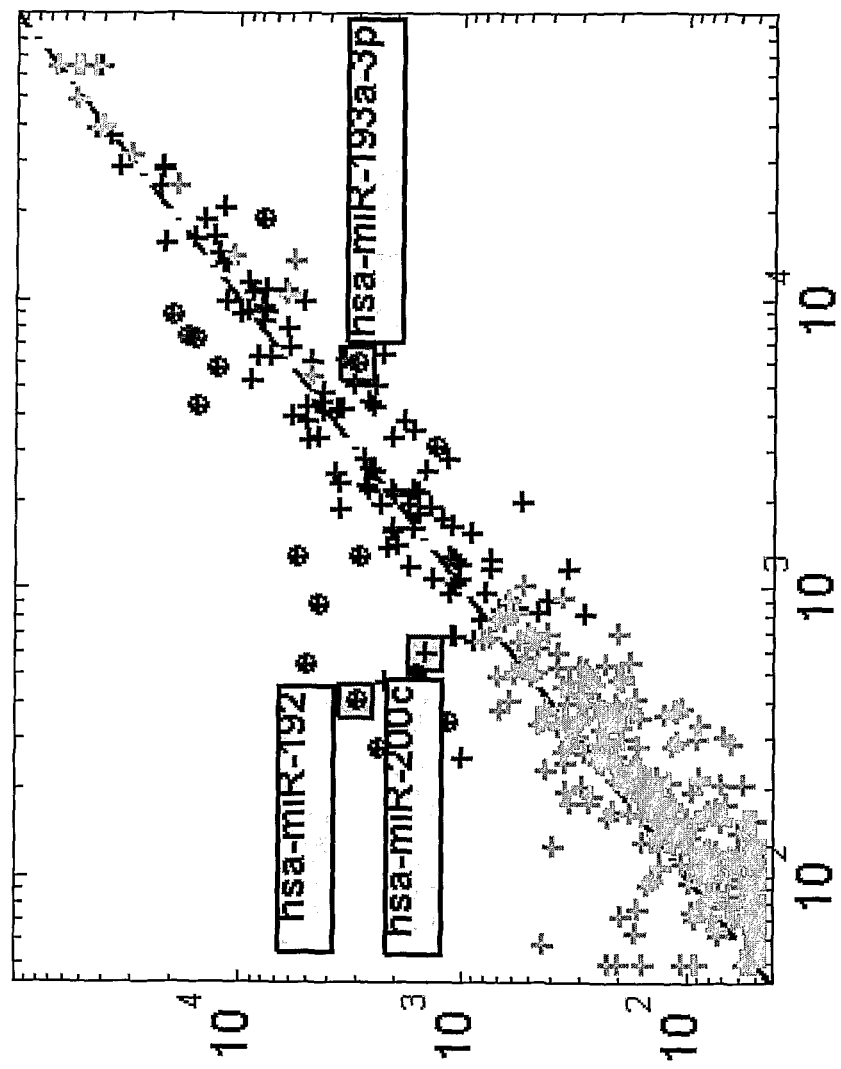

Comparison of microRNA expression between mesothelioma samples and adenocarcinoma samples, and between mesothelioma samples and RCC sample, are presented in FIGS. 18A and 18B respectively.

Figure 18C:
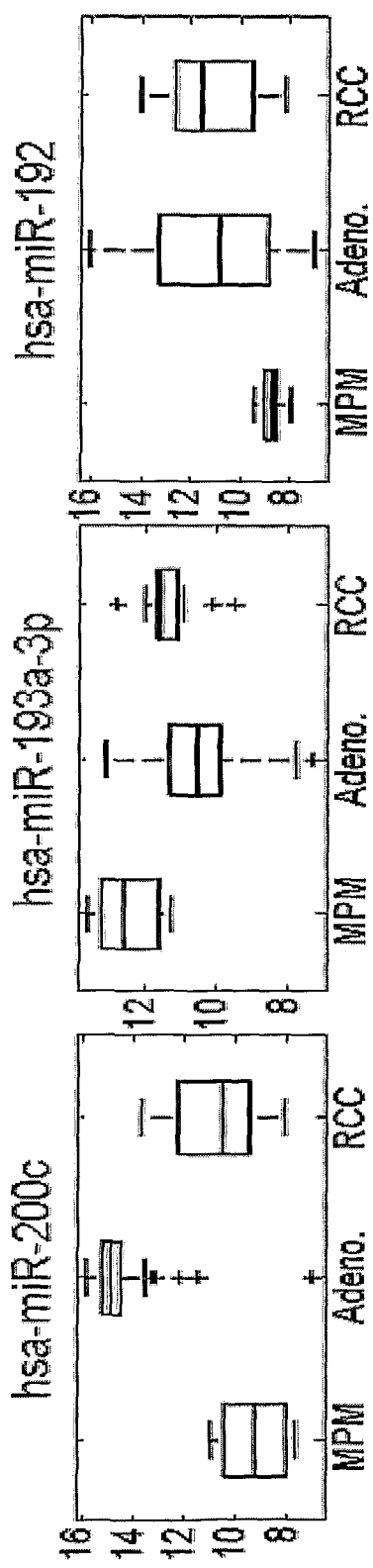

Hsa-miR-193a-3p (SEQ ID NO. 10) was the only microRNA that was significantly over-expressed in mesothelioma compared to both adenocarcinoma and RCC. The hsa-miR-200 family was strongly over-expressed in the adenocarcinoma samples, with hsa-miR-200c (SEQ ID NO. 11) having the strongest signals. Hsa-miR-192 (SEQ ID NO. 2) and hsa-miR-194 (SEQ ID NO. 4) expression was highest in RCC, with a somewhat stronger signal for hsa-miR-192 (SEQ ID NO. 2). Together, these microRNAs comprise a panel with specific expression in each of the studied groups of tumors (FIG. 18C).

Figure 18D:
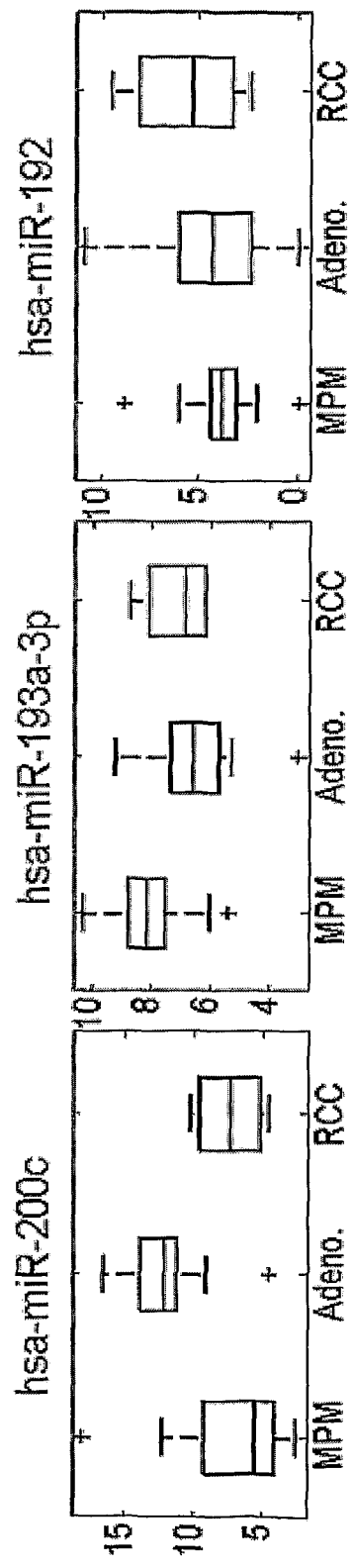

The expression of these microRNAs were validated using a qRT-PCR platform, measuring the expression levels of hsa-miR-200c (SEQ ID NO. 11), hsa-miR-193a-3p (SEQ ID NO. 10), and hsa-miR-192 (SEQ ID NO. 2) in FFPE tumors samples including 22 MPM samples (7 of the samples repeated from the microarray set and 15 new samples), 4 renal cell carcinomas (including two repeated samples), and 39 adenocarcinomas (5 of them repeated) of the lung (n=25), breast (n=4), bladder (n=2), ovary (n=4), colon (n=2) and pancreas (n=2). Expression level of the U6 snRNA (SEQ ID NO. 41) was measured in each sample and used for normalization. PCR Ct signals were normalized for each sample by subtracting the average Ct of U6 for this sample from the average Ct of each microRNA for this sample, and adding back the average Ct of U6 across all samples. The signal was then inverted by subtracting this normalized value from an arbitrarily chosen value of 40. Thus, low values of normalized-inverted Ct represent low abundance or expression levels of the microRNA. Using the qRT-PCR platform and measuring additional independent samples, the expression levels of these microRNAs maintained the same pattern (FIG. 18D) indicating that the differences in expression are a general property of these tissues that can be robustly measured.

Figure 19B:
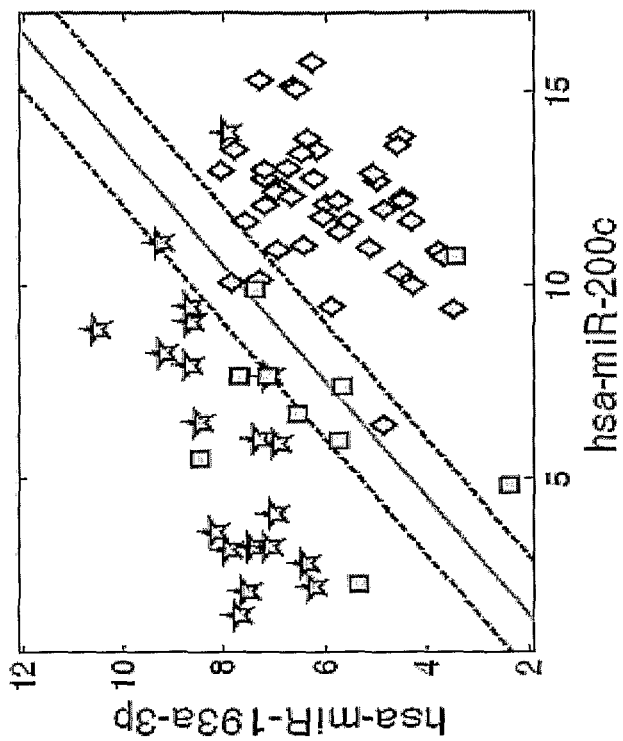
FIG. 19 shows differential diagnosis of mesothelioma (stars) from HCC (Hepatocellular carcinoma, circles), RCC (squares) and adenocarcinoma (diamonds) using expression levels of microRNAs. Expression levels (normalized-inverted Ct) of hsa-miR-192 (SEQ ID NO. 2) and hsa-miR-122 (SEQ ID NO. 24) (FIG. 19A, FIG. 19C) and hsa-miR-200c (SEQ ID NO. 11) and hsa-miR-193a-3p (SEQ ID NO. 10) (FIG. 19B, FIG. 19D) were measured using qRT-PCR in a training set of 20 MPM samples, 10 RCC samples, 5 HCC samples, and 44 adenocarcinomas, of which 10 are from colon or pancreas tissues (FIG. 19A, FIG. 19B), and in an independent blinded test set of 12 MPM samples, 8 RCC samples (5 new), 5 HCC samples, and 42 adenocarcinomas, of which 8 are from colon or pancreas tissues (FIG. 19C, FIG. 19D). Solid lines mark classification thresholds on expression levels of hsa-miR-192 (vertical line in FIG. 19A and FIG. 19C) and combined expression levels of hsa-miR-200c and hsa-miR-193a-3p (diagonal line in FIG. 19B and FIG. 19D). Parallel dotted lines indicate uncertainty margins of 1.5 normalized-inverted Ct units. The horizontal dotted line in FIG. 19A and FIG. 19C demonstrates a possible classification threshold on expression levels of hsa-miR-122 (SEQ ID NO. 24). Two additional mesothelioma samples in the training set had much lower expression of hsa-miR-192 (SEQ ID NO. 2) (normalized-inverted Ct of −5 and −5.5) and were omitted from panel A for optimal scaling. One additional adenocarcinoma sample in the training set and four additional adenocarcinoma samples in the test set had low expression of hsa-miR-193a-3p (normalized-inverted Ct of −3.5 and −1.3, −4, −5.4 and −5.7 respectively) and were omitted from panels B and D for optimal scaling.
Figure 19A:
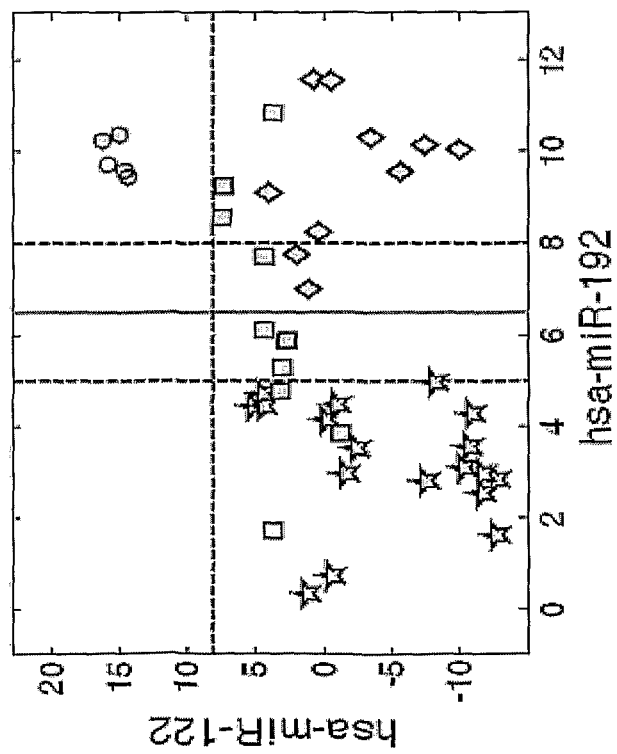
Figure 19D:
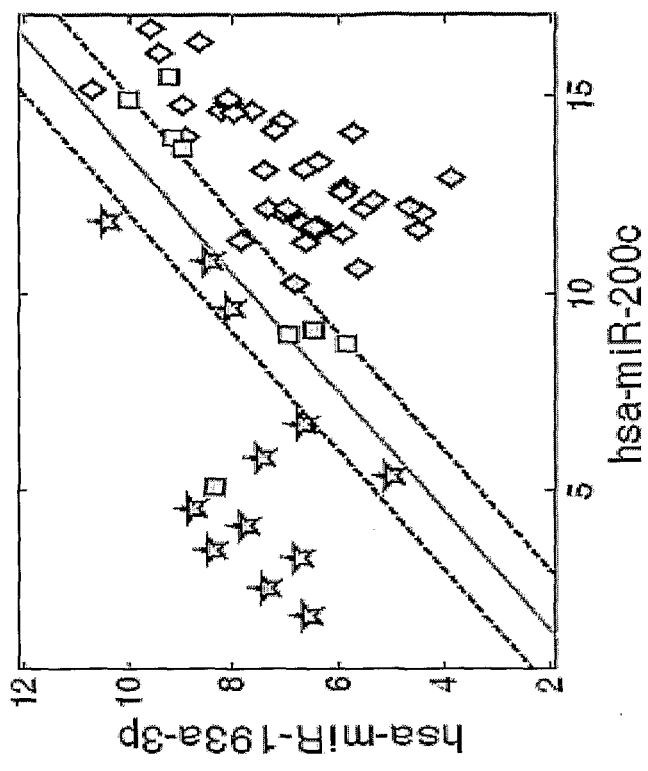
Figure 19C:
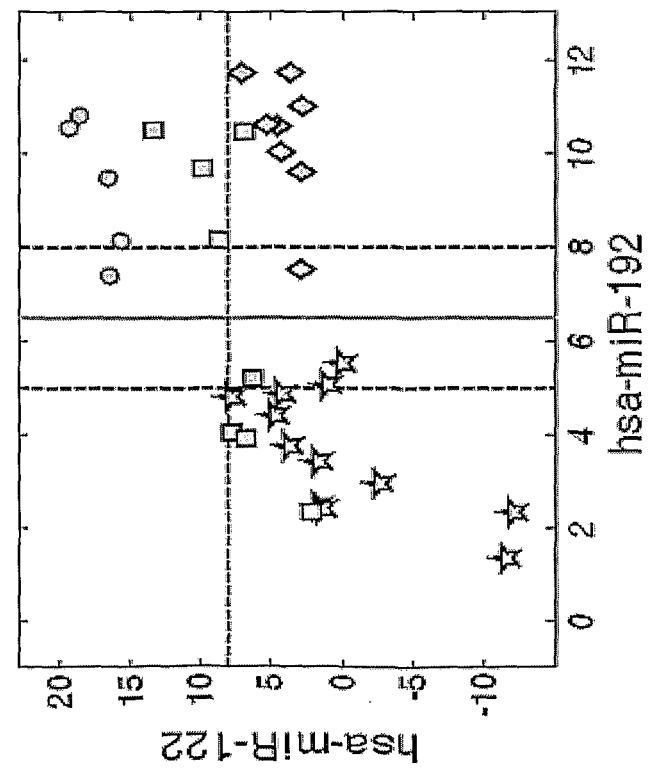

A quantitative diagnostic assay was developed for the differential diagnosis of mesothelioma from adenocarcinoma, RCC or HCC (Hepatocellular carcinoma), by defining explicit classification rules and thresholds of the expression levels of these microRNAs. The qRT-PCR platform was used to measure expression levels of hsa-miR-200c (SEQ ID NO 11), hsa-miR-193a-3p (SEQ ID NO 10), hsa-miR-192 (SEQ ID NO 2), and hsa-miR-122 (SEQ ID NO 24), as well as the U6 (SEQ ID NO 41) snRNA for normalization, [in triplicates] for each sample. The classification rule and thresholds was trained on a set of 79 samples consisting of 20 MPM samples (including 12 samples repeated from previous sets), 10 RCC samples (including 4 repeated samples), 5 HCC samples, and 44 adenocarcinomas (16 of them repeated) of the lung (n=20), bladder (n=5), colon (n=5), pancreas (n=5), breast (n=5), and ovary (n=4). The expression level of hsa-miR-192 (SEQ ID NO. 2) could easily distinguish mesothelioma samples from samples of HCC or adenocarcinomas from colon and pancreas tissues, while RCC samples had a wider distribution of expression levels (FIG. 19A). Hsa-miR-122 (SEQ ID NO. 24) was indeed very strongly over-expressed in the HCC samples (FIG. 19A). The combination of hsa-miR-200c (SEQ ID NO. 11), over-expressed in adenocarcinomas, and hsa-miR-193a-3p (SEQ ID NO. 10), over-expressed in mesotheliomas, accurately distinguished the two groups, with RCC exhibiting a wider distribution of signals (FIG. 19B).

Using these expression measurements, a simple classification rule determining whether a given sample is a mesothelioma sample, was defined. If expression of hsa-miR-192 (SEQ ID NO. 24) (normalzed Ct) is lower than 6.5 (solid vertical line in FIG. 19A), and the expression of hsa-miR-200c (SEQ ID NO. 11) plus 1.5 (normalized Ct units) is lower than 1.5 times the normalized Ct of hsa-miR-193a-3p (SEQ ID NO. 10) (the solid diagonal line in FIG. 19B), the samples is identified as mesothelioma; otherwise, it is identified as another type of tumor, either RCC, HCC or adenocarcinoma. In graphical terms, a sample is identified as mesothelioma if its expression values lie to the left of the solid line in FIG. 19A and above the diagonal line in FIG. 19B. A margin of 1.5 normalized Cts in each side of these decision thresholds (the dotted lines parallel to the solid lines in FIG. 19) was chosen as a region of lower certainty, reflecting the reproducibility of the qRT-PCR assay and providing accurate performance on the training set, while taking into account additional biological variation that may not be represented in the training set. This decision rule, which combines the expression of the three microRNAs with different specificities, reached overall accuracy of 94% on the training set. As demonstrated in table 12, 91% of the samples were classified with high confidence, of which 94% were classified correctly. RCCs had the lowest accuracy due to the wider distribution of expression levels, but the combined decision criteria allowed 7 of the 10 samples to be accurately identified, 5 of them with high accuracy.

TABLE 12

Classification of the training and test samples using the defined differential diagnosis rule on expression levels of hsa-miR-192 (SEQ ID NO. 24), hsa-miR-200c (SEQ ID NO. 11), and hsa-miR-193a-3p (SEQ ID NO. 10).

| | Training set | | | | | Test set | | | |
|---|---|---|---|---|---|---|---|---|---|
| | | Correct | | Errors | | | Correct | | Errors |
| | n | HC | LC | HC | LC | n | HC | LC | HC | LC |
| Lung | 20 | 19 | | | 1 | 15 | 15 | | | |
| Bladder | 5 | 5 | | | | 9 | 9 | | | |
| Ovary | 4 | 4 | | | | 6 | 6 | | | |
| Breast | 5 | 4 | 1 | | | 4 | 2 | 2 | | |
| Colon | 5 | 5 | | | | 5 | 5 | | | |
| Pancreas | 5 | 4 | 1 | | | 3 | 3 | | | |
| All adeno. | 44 | 41 | 2 | | 1 | 42 | 40 | 2 | | |
| HCC | 5 | 5 | | | | 5 | 5 | | | |
| RCC | 10 | 5 | 2 | | 3 | 8 | 5 | 2 | 1 | |
| All non-MPM | 59 | 51 | 4 | | 4 | 55 | 50 | 4 | 1 | |
| Percentage | % | 86 | 6.8 | | 6.8 | % | 91 | 7.3 | 1.8 | |
| MPM | 20 | 17 | 2 | 1 | | 12 | 7 | 5 | | |
| Percentage | % | 85 | 10 | 5 | | % | 58 | 42 | | |
| All samples | 79 | 68 | 6 | 1 | 4 | 67 | 57 | 9 | 1 | |
| Percentage | % | 86 | 7.6 | 1.3 | 5.1 | % | 85 | 13 | 1.5 | |

HC—high confidence; LC—low confidence.

The importance and usefulness of these microRNAs in the differential diagnosis of mesothelioma was demonstrated in different samples sets and platforms. In order to validate the accuracy of the decision rule and decision thresholds chosen, these thresholds were used to classify samples that were not included in the training set, including new samples as well as samples that were used in earlier discovery steps. After the classification rule was defined using the training set, the same protocol was used to measure expression of these microRNAs in a test set (FIGS. 19C and 19D) including 12 mesothelioma samples, 8 RCC samples, 5 HCC samples, and 42 adenocarcinomas of the lung (n=15), bladder (n=9), ovary (n=6), colon (n=5), breast (n=4), and pancreas (n=3). Of the 67 samples in the test set, 44 were independent samples, and 23 samples (9 mesotheliomas, 3 RCCs and 11 adenocarcinomas) were repeated from the earlier discovery steps (FIG. 18), but were not used in training the decision rule or thresholds. Using the pre-defined classification rule, each sample was assigned to one of four categories: "mesothelioma with high confidence"; "mesothelioma with low confidence"; "non-mesothelioma with low confidence"; or "non-mesothelioma with high confidence". As demonstrated in table 12, this classification rule correctly identified 66 of the 67 test samples (98.5%), of which 57 were classified with high confidence. Among the 44 new test samples, 43 were classified correctly, of which 37 were classified with high confidence, resulting in 100% sensitivity and 98% specificity for identification of mesothelioma.

The results show that the microRNA-based assay, using expression levels of 3 microRNAs, is able to accurately diagnose malignant pleural mesothelioma (MPM) and distinguish it from other epithelial malignancies involving the pleura, with very high sensitivity and specificity. This assay is simple to perform and highly reliable in its reproducibility, and is at least a potent addition to the currently available tools used by pathologists to diagnose this cancer. The small number of microRNAs needed for classification, the high tissue specificity of these microRNAs and the ease of their determination from archival fixed tissues embedded in paraffin, make them very attractive candidates for reliable and powerful biomarkers of this disease. The recent demonstration of their preservation in body fluids and serum may also signify their future use in the early and accurate diagnosis of mesothelioma in related pleural effusion and for early detection of mesothelioma in general.

Example 4

Microarray Assay to Distinguish Between Squamous Carcinoma and Adenocarcinoma

4a) Samples

62 NSCLC squamous cell lung carcinoma samples and 60 NSCLC lung adenocarcinoma samples, comprising fresh-frozen and FFPE samples, were obtained from several sources.

Tissue from representative blocks was sectioned into 1.5 ml microcentrifuge tubes (five 10 micrometer sections), and serial hematoxylin and eosin-stained slides were obtained from each block, to evaluate amount of tumor at sectioning. All samples were anonymized and blinded to the investigators performing the validation assays and analyses.

FFPE tissues were deparaffinized with xylene, washed in ethanol, and digested with proteinase K. The RNA was extracted with acid phenol:chloroform followed by ethanol precipitation and DNAse digestion. From frozen tissues, total RNA was extracted using the miRvana microRNA isolation kit (Ambion).

4b) Microrray

Custom microRNA microarrays were prepared as follows: ~650 DNA oligonucleotide probes representing microRNAs were spotted in triplicate on coated microarray slides (Nexterion® Slide E, Schott, Mainz, Germany). 3-5 µg of total RNA were labeled by ligation of an RNA-linker, p-rCrU-Cy/dye (Dharmacon, Lafayette, Colo.; Cy3 or Cy5) to the 3' end. Slides were incubated with the labeled RNA for 12-16 hr at 42° C. and then washed twice. Arrays were scanned at a resolution of 10 µm, and images were analyzed using SpotReader software (Niles Scientific, Portola Valley, Calif.). Microarray spots were combined and signals normalized.

4c) Microarray Data Analysis and Statistics

Median normalized fluorescence signal greater than 300 in at least one of the two groups (squamous cell carcinoma samples or adenocarcinoma samples) was considered reliable expression in the microarray. Significance of differences in expression levels were assessed by a two-sided unpaired t-test. The Bonferroni method was used to control for multiple hypotheses testing by adjusting the p-value threshold to 0.05/141=0.00035.

4d) Assay

Figure 20:
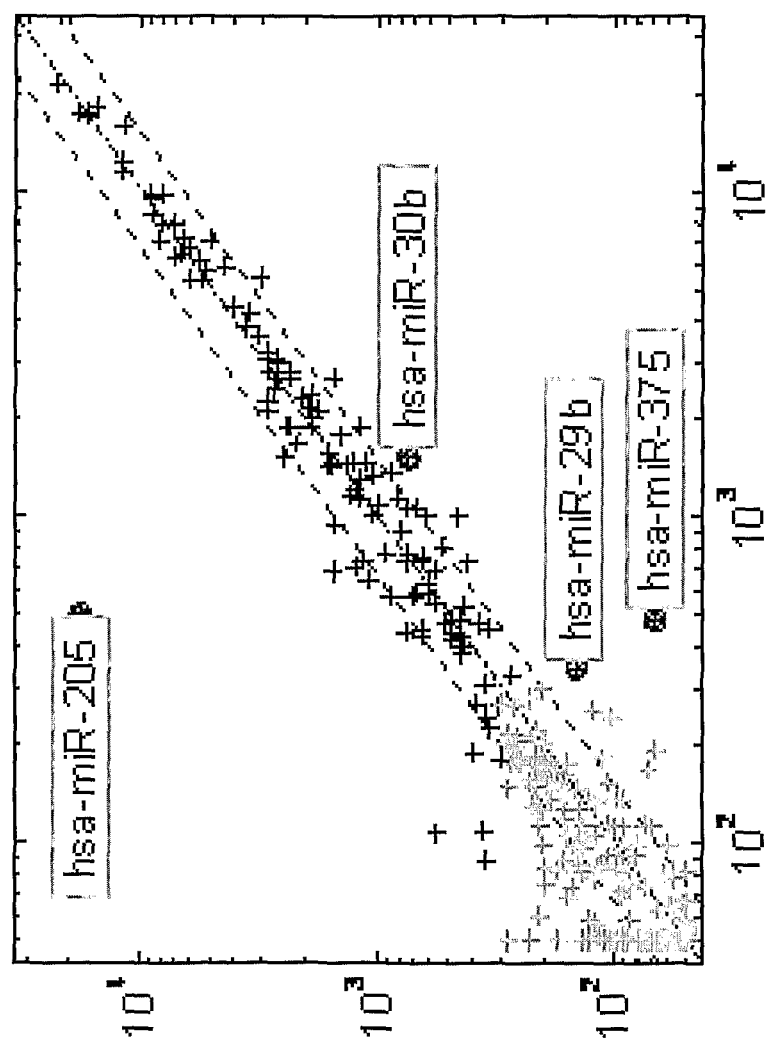
FIG. 20 shows a scatter plot of average miR expression (fluorescence (shown in log-scale)) on microarray data, in which the X-axis represents the mean expression in adenocarcinoma samples (n=60) and the Y-axis represents the mean expression in squamous cell carcinoma samples (n=62). The circled symbols relate to significantly differentially expressed miRs as determined by the Bonferroni method, including hsa-miR-29b (SEQ ID NO. 44), hsa-miR-30b (SEQ ID NO. 47), hsa-miR-375 (SEQ ID NO. 8) and hsa-miR-205 (SEQ ID NO. 49). The middle diagonal line represents the expected expression for non-differentially expressed miRNAs (same expression level in adenocarcinoma and squamous cell carcinoma samples), and the other diagonal lines represent fold 2 factor lines.

The arrays results of squamous cell carcinoma samples vs. adenocarcinoma samples are presented in FIG. 20.

Figure 21:
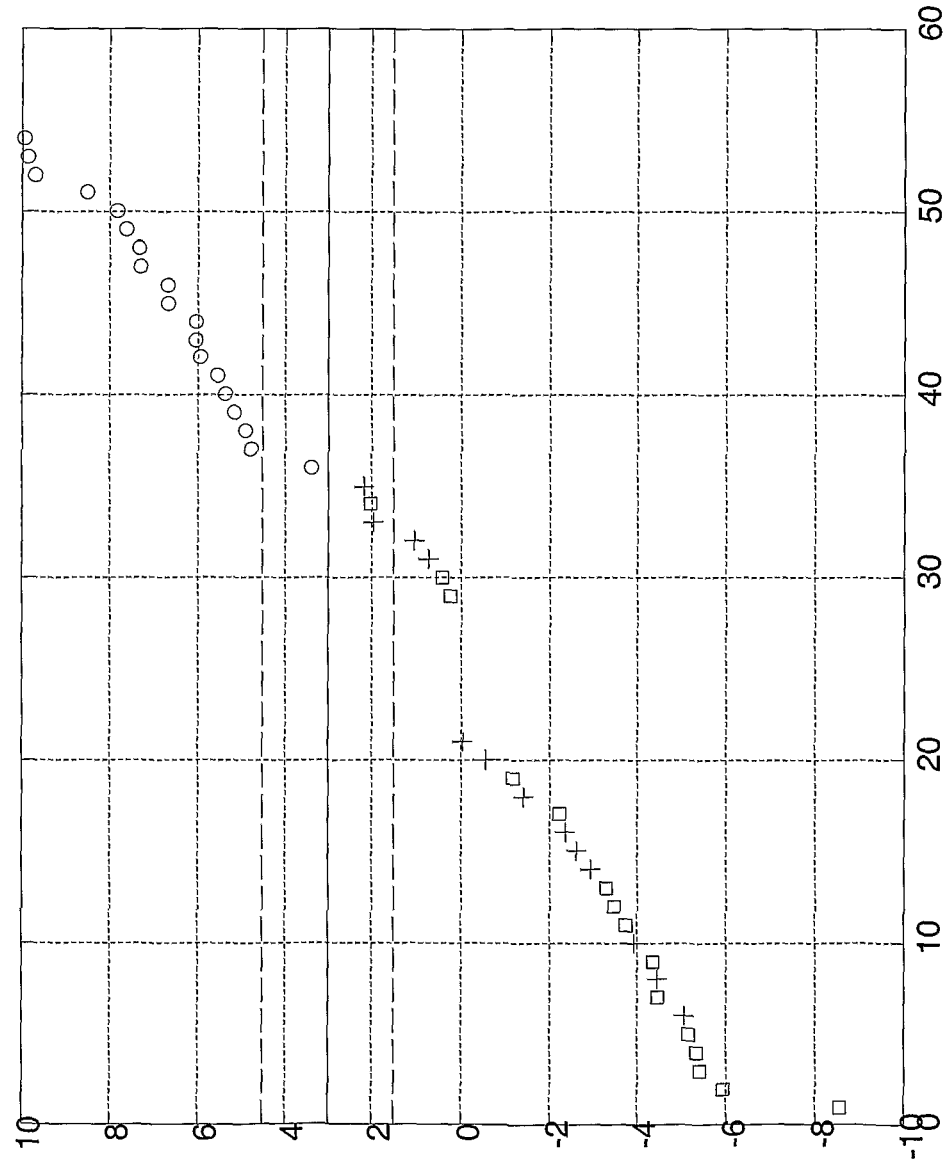
FIG. 21 shows an exemplified classifier which is used to distinguish between samples of Non Small Cell Lung Carcinoma (NSCLC) with squamous histology (circles), and samples of NSCLC with non-squamous histology (squares-adenocarcinoma; pluses-large cell carcinoma), using qRT-PCR. The Y-axis depicts the value obtained by subtracting the expression level, in Ct, of hsa-miR-205 (SEQ ID NO. 49) from the expression level, in Ct, of hsa-miR-375 (SEQ ID NO. 8). (The x-axis is the running order of the samples.)

The expression of hsa-miR-205 (SEQ ID NO. 49) in squamous cell carcinoma samples is significantly higher than its expression in adenocarcinoma samples. Contrastingly, the expression of hsa-miR-29b (SEQ ID NO. 44), hsa-miR-30b (SEQ ID NO. 47) and hsa-miR-375 (SEQ ID NO. 8) in squamous cell carcinoma samples are significantly lower than their expression in adenocarcinoma samples. Accordingly, these miRs may serve as a tool for differentiating between squamous cell carcinoma and adenocarcinoma samples, as indicated in FIG. 21.

Example 5 qRT-PCR Assay for Distinguishing Between Non Small Cell Lung Carcinoma (NSCLC) Samples with Squamous and Non-Squamous Histology 5a) Samples 47 samples, out of which 19 were squamous cell lung carcinoma, 15 were Adenocarcinoma and 13 were Large NSCLC, comprising fresh-frozen and FFPE samples, were obtained from several sources.

Tissue from representative blocks was sectioned into 1.5 ml microcentrifuge tubes (five 10 micrometer sections), and serial hematoxylin and eosin-stained slides were obtained from each block, to evaluate amount of tumor at sectioning. All samples were anonymized and blinded to the investigators performing the validation assays and analyses.

FFPE tissues were deparaffinized with xylene, washed in ethanol, and digested with proteinase K. The RNA was extracted with acid phenol:chloroform followed by ethanol precipitation and DNAse digestion. From frozen tissues, total RNA was extracted using the miRvana microRNA isolation kit (Ambion).

5b) PCR Primers and Probes

The sequences of the Fwd primers and MGB probes used in the PCR are indicated below:

| Name | Fwd (Forward miR specific) primer | SEQ ID NO | MGB probe | SEQ ID NO |
|---|---|---|---|---|
| miR-375 | CAGTCATTTGGGTTTGTCGTTCGGCTC | 53 | CCGTTTTTTTTTTTCACGCGAG | 54 |
| miR-205 | CAGTCATTTGGGTCCTTCATTCCACCGG | 51 | CGTTTTTTTTTTTCAGACTCC | 52 |
| miR-21 | CAGTCATTTGGGTAGCTTATCAGACTGA | 56 | CCGTTTTTTTTTTTCAACATCA | 57 |

| Name | Fwd (Forward miR specific) primer | SEQ ID NO | MGB probe | SEQ ID NO |
|---|---|---|---|---|
| U6 | GCAAGGATGACACG CAAATTC | 39 | AATATGGAACGC TTCACG | 40 |

The expression levels of miR-375 (SEQ ID NO. 8) and miR-205 (SEQ ID NO. 49) were normalized with hsa-miR-21 (SEQ ID NO. 55) and U6 (SEQ ID NO. 41).

5c) Assay

The expression level of miR-375 (SEQ ID NO. 8) is higher in non-squamous samples than in squamous samples, whereas the expression level of miR-205 (SEQ ID NO. 49) is higher in squamous samples than in non-squamous samples.

Subtraction of the expression level of miR-205 (SEQ ID NO. 49) from the expression level of hsa-miR-375 (SEQ ID NO. 8) provides for distinguishing between NSCLC samples with squamous and non-squamous histology, as indicated in FIG. 21.

The decision rule is:

| miR-375 – miR-205 [Ct] | Classification | Confidence |
|---|---|---|
| >4.5 | Squamous | High |
| >3 and <4.5 | Squamous | Low |
| >1.5 <3 | Non-Squamous | Low |
| <1.5 | Non-Squamous | High |

Sensitivity 100%; Specificity 100%; Percentage of samples classified in high confidence is 92.6.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It should be understood that the detailed description and specific examples, while indicating preferred embodiments of the invention, are given by way of illustration only, since various changes and modifications within the spirit and scope of the invention will become apparent to those skilled in the art from this detailed description.

The invention claimed is:

1. A method to distinguish between pleural mesothelioma and adenocarcinoma in a human subject in need of treatment for lung cancer, and determine a therapeutic strategy based on the distinction between pleural mesothelioma and adenocarcinoma, the method comprising:
   (a) obtaining lung samples from the human subject;
   (b) extracting total RNA from the lung samples;

(c) determining the expression profile of SEQ ID NO: 2, SEQ ID NO: 3 or SEQ ID NO: 10 and SEQ ID NO: 11 in the lung samples by nucleic acid amplification using primer pairs comprising SEQ ID NOS: 29-32, 37 and 38, or sequences that are 90% identical to SEQ ID NOS: 29-32, 37 and 38, or by hybridization using a probe which is complimentary to SEQ ID NO: 2, SEQ ID NO: 3, or SEQ ID NO: 10 and SEQ ID NO: 11;

(d) normalizing said expression profile;

(e) distinguishing between pleural mesothelioma and adenocarcinoma based on the expression profile of SEQ ID NO: 2, SEQ ID NO: 3 or SEQ ID NO: 10 and SEQ ID NO: 11 in the lung samples relative to a reference threshold value, wherein an increase in the combined expression values of SEQ ID NO: 2, SEQ ID NO: 3 or SEQ ID NO: 10, and SEQ ID NO: 11 in the lung samples relative to a reference threshold value indicates that the human subject has pleural mesothelioma; and (f) if determining a therapeutic strategy for said human subject in need of treatment for lung cancer based on the distinction between pleural mesothelioma and adenocarcinoma.

2. The method of claim 1, wherein said adenocarcinoma originates from the lung.

3. The method of claim 2, wherein said lung cancer is selected from the group consisting of lung squamous cell carcinoma, lung undifferentiated small cell carcinoma, lung undifferentiated large cell carcinoma, lung adenocarcinoma, nonsmall-cell lung cancer (NSCLC), lung carcinoid and neuroendocrine-large cell carcinoma.

4. The method of claim 1, wherein said lung sample is a fluid or a tissue sample.

5. The method of claim 1, wherein said lung sample is obtained from a human subject with cancer of unknown primary (CUP), with a primary cancer or with a metastatic cancer.

6. The method of claim 1, wherein the step of distinguishing between pleural mesothelioma and adenocarcinoma is performed using a classifier algorithm.

7. A kit for distinguishing between pleural mesothelioma and adenocarcinoma, said kit comprising a set of probes comprising the reverse complementary sequence of SEQ ID NO: 2, SEQ ID NO: 3 and SEQ ID NO: 11 or a sequence that is 90% identical to said sequences.

* * * * *

SEQUENCE LISTING

```
<160> NUMBER OF SEQ ID NOS: 87

<210> SEQ ID NO 1
<211> LENGTH: 22
<212> TYPE: RNA
<213> ORGANISM: Homo sapiens

<400> SEQUENCE: 1
uaacacuguc ugguaaagau gg                                              22

<210> SEQ ID NO 2
<211> LENGTH: 21
<212> TYPE: RNA
<213> ORGANISM: Homo sapiens

<400> SEQUENCE: 2
cugaccuaug aauugacagc c                                               21

<210> SEQ ID NO 3
<211> LENGTH: 21
<212> TYPE: RNA
<213> ORGANISM: Homo sapiens

<400> SEQUENCE: 3
aacuggccua caaaguccca g                                               21

<210> SEQ ID NO 4
<211> LENGTH: 22
<212> TYPE: RNA
<213> ORGANISM: Homo sapiens

<400> SEQUENCE: 4
uguaacagca acuccaugug ga                                              22
```

<210> SEQ ID NO 5
<211> LENGTH: 22
<212> TYPE: RNA
<213> ORGANISM: Homo sapiens

<400> SEQUENCE: 5
uaacacuguc ugguaacgau gu                                              22

<210> SEQ ID NO 6
<211> LENGTH: 23
<212> TYPE: RNA
<213> ORGANISM: Homo sapiens

<400> SEQUENCE: 6
uaauacugcc ugguaaugau gac                                             23

<210> SEQ ID NO 7
<211> LENGTH: 22
<212> TYPE: RNA
<213> ORGANISM: Homo sapiens

<400> SEQUENCE: 7
uaauacugcc ggguaaugau gg                                              22

<210> SEQ ID NO 8
<211> LENGTH: 22
<212> TYPE: RNA
<213> ORGANISM: Homo sapiens

<400> SEQUENCE: 8
uuuguucguu cggcucgcgu ga                                              22

<210> SEQ ID NO 9
<211> LENGTH: 22
<212> TYPE: RNA
<213> ORGANISM: Homo sapiens

<400> SEQUENCE: 9
uaauacuguc ugguaaaacc gu                                              22

<210> SEQ ID NO 10
<211> LENGTH: 22
<212> TYPE: RNA
<213> ORGANISM: Homo sapiens

<400> SEQUENCE: 10
aacuggccua caaaguccca gu                                              22

<210> SEQ ID NO 11
<211> LENGTH: 23
<212> TYPE: RNA
<213> ORGANISM: Homo sapiens

<400> SEQUENCE: 11
uaauacugcc ggguaaugau gga                                             23

<210> SEQ ID NO 12
<211> LENGTH: 22
<212> TYPE: RNA
<213> ORGANISM: Homo sapiens

<400> SEQUENCE: 12
uaauacugcc ugguaaugau ga                                          22

<210> SEQ ID NO 13
<211> LENGTH: 95
<212> TYPE: RNA
<213> ORGANISM: Homo sapiens

<400> SEQUENCE: 13
cggccggccc uggguccauc uuccaguaca guguuggaug gucuaauugu gaagcuccua    60
acacugucug guaaagaugg cucccgggug gguuc                              95

<210> SEQ ID NO 14
<211> LENGTH: 110
<212> TYPE: RNA
<213> ORGANISM: Homo sapiens

<400> SEQUENCE: 14
gccgagaccg agugcacagg gcucugaccu augaauugac agccagugcu cucgucuccc    60
cucuggcugc caauuccaua ggucacaggu auguucgccu caaugccagc              110

<210> SEQ ID NO 15
<211> LENGTH: 88
<212> TYPE: RNA
<213> ORGANISM: Homo sapiens

<400> SEQUENCE: 15
cgaggauggg agcugagggc ugggucuuug cgggcgagau gagggugucg gaucaacugg    60
ccuacaaagu cccaguucuc ggcccccg                                      88

<210> SEQ ID NO 16
<211> LENGTH: 85
<212> TYPE: RNA
<213> ORGANISM: Homo sapiens

<400> SEQUENCE: 16
augguguuau caaguguaac agcaacucca ugggacugu guaccaauuu ccaguggaga     60
ugcuguuacu uuugaugguu accaa                                         85

<210> SEQ ID NO 17
<211> LENGTH: 85
<212> TYPE: RNA
<213> ORGANISM: Homo sapiens

<400> SEQUENCE: 17
ugguucccgc cccuguaac agcaacucca ugggaagug cccacugguu ccaguggggc      60
ugcuguuauc uggggcgagg gccag                                         85

<210> SEQ ID NO 18
<211> LENGTH: 90
<212> TYPE: RNA
<213> ORGANISM: Homo sapiens

<400> SEQUENCE: 18 ccgggcccu gugagcaucu uaccggacag ugcuggauuu cccagcuuga cucuaacacu     60
gucugguaac gauguucaaa ggugacccgc                                    90

<210> SEQ ID NO 19
<211> LENGTH: 95
<212> TYPE: RNA
<213> ORGANISM: Homo sapiens

```
<400> SEQUENCE: 19
ccagcucggg cagccguggc caucuuacug ggcagcauug gauggaguca ggucucuaau    60
acugccuggu aaugaugacg gcggagcccu gcacg                              95

<210> SEQ ID NO 20
<211> LENGTH: 68
<212> TYPE: RNA
<213> ORGANISM: Homo sapiens

<400> SEQUENCE: 20
cccucgucuu acccagcagu guuugggugc gguuggagu cucuaauacu gccggguaau     60
gauggagg                                                            68

<210> SEQ ID NO 21
<211> LENGTH: 64
<212> TYPE: RNA
<213> ORGANISM: Homo sapiens

<400> SEQUENCE: 21
ccccgcgacg agccccucgc acaaaccgga ccugagcguu uguucguuc ggcucgcgug     60 aggc                                                                64

<210> SEQ ID NO 22
<211> LENGTH: 83
<212> TYPE: RNA
<213> ORGANISM: Homo sapiens

<400> SEQUENCE: 22
cgccggccga ugggcgucuu accagacaug guuagaccug gcccucuguc uaauacuguc    60
ugguaaaacc guccauccgc ugc                                           83

<210> SEQ ID NO 23
<211> LENGTH: 23
<212> TYPE: RNA
<213> ORGANISM: Homo sapiens

<400> SEQUENCE: 23
uggaguguga caauggiguguu ugu                                         23

<210> SEQ ID NO 24
<211> LENGTH: 21
<212> TYPE: RNA
<213> ORGANISM: Homo sapiens

<400> SEQUENCE: 24
uggaguguga caauggiguguu u                                           21

<210> SEQ ID NO 25
<211> LENGTH: 85
<212> TYPE: RNA
<213> ORGANISM: Homo sapiens

<400> SEQUENCE: 25
ccuuagcaga gcugiggagu gugacaaugg uguuuguguc uaaacuauca aacgccauua    60
ucacacuaaa uagcuacugc uaggc                                         85

<210> SEQ ID NO 26
<211> LENGTH: 23
<212> TYPE: RNA
```

<213> ORGANISM: Homo sapiens

<400> SEQUENCE: 26
uaacacuguc ugguaaagau ggc                                              23

<210> SEQ ID NO 27
<211> LENGTH: 28
<212> TYPE: DNA
<213> ORGANISM: Artificial Sequence
<220> FEATURE:
<223> OTHER INFORMATION: Synthetic

<400> SEQUENCE: 27
cagtcatttg ggtggagtgt gacaatgg                                         28

<210> SEQ ID NO 28
<211> LENGTH: 23
<212> TYPE: DNA
<213> ORGANISM: Artificial sequence
<220> FEATURE:
<223> OTHER INFORMATION: Synthetic

<400> SEQUENCE: 28 ccgtttttt tttttaaaca cca                                               23

<210> SEQ ID NO 29
<211> LENGTH: 28
<212> TYPE: DNA
<213> ORGANISM: Artificial Sequence
<220> FEATURE:
<223> OTHER INFORMATION: Synthetic

<400> SEQUENCE: 29
cagtcatttg ggctgaccta tgaattga                                         28

<210> SEQ ID NO 30
<211> LENGTH: 22
<212> TYPE: DNA
<213> ORGANISM: Artificial sequence
<220> FEATURE:
<223> OTHER INFORMATION: Synthetic

<400> SEQUENCE: 30
cgtttttttt ttttggctgt ca                                               22

<210> SEQ ID NO 31
<211> LENGTH: 28
<212> TYPE: DNA
<213> ORGANISM: Artificial Sequence
<220> FEATURE:
<223> OTHER INFORMATION: Synthetic

<400> SEQUENCE: 31
cagtcatttg ggaactggcc tacaaagt                                         28

<210> SEQ ID NO 32
<211> LENGTH: 23
<212> TYPE: DNA
<213> ORGANISM: Artificial sequence
<220> FEATURE:
<223> OTHER INFORMATION: Synthetic

<400> SEQUENCE: 32 ccgtttttt ttttttactgg gac                                              23

```
<210> SEQ ID NO 33
<211> LENGTH: 28
<212> TYPE: DNA
<213> ORGANISM: Artificial Sequence
<220> FEATURE:
<223> OTHER INFORMATION: Synthetic

<400> SEQUENCE: 33
cagtcatttg ggtaacactg tctggtaa                                           28

<210> SEQ ID NO 34
<211> LENGTH: 23
<212> TYPE: DNA
<213> ORGANISM: Artificial sequence
<220> FEATURE:
<223> OTHER INFORMATION: Synthetic

<400> SEQUENCE: 34
ccgttttttt tttttgccat ctt                                                23

<210> SEQ ID NO 35
<211> LENGTH: 28
<212> TYPE: DNA
<213> ORGANISM: Artificial Sequence
<220> FEATURE:
<223> OTHER INFORMATION: Synthetic

<400> SEQUENCE: 35
cagtcatttg ggtggagtgt gacaatgg                                           28

<210> SEQ ID NO 36
<211> LENGTH: 23
<212> TYPE: DNA
<213> ORGANISM: Artificial sequence
<220> FEATURE:
<223> OTHER INFORMATION: Synthetic

<400> SEQUENCE: 36
ccgttttttt tttttacaaa cac                                                23

<210> SEQ ID NO 37
<211> LENGTH: 28
<212> TYPE: DNA
<213> ORGANISM: Artificial Sequence
<220> FEATURE:
<223> OTHER INFORMATION: Synthetic

<400> SEQUENCE: 37
cagtcatttg ggtaatactg ccgggtaa                                           28

<210> SEQ ID NO 38
<211> LENGTH: 22
<212> TYPE: DNA
<213> ORGANISM: Artificial sequence
<220> FEATURE:
<223> OTHER INFORMATION: Synthetic

<400> SEQUENCE: 38 cgttttttt ttttccatca tt                                                  22

<210> SEQ ID NO 39
<211> LENGTH: 21
<212> TYPE: DNA
<213> ORGANISM: Artificial sequence
<220> FEATURE:
<223> OTHER INFORMATION: Synthetic
```

```
<400> SEQUENCE: 39
gcaaggatga cacgcaaatt c                                              21

<210> SEQ ID NO 40
<211> LENGTH: 18
<212> TYPE: DNA
<213> ORGANISM: Artificial sequence
<220> FEATURE:
<223> OTHER INFORMATION: Synthetic

<400> SEQUENCE: 40
aatatggaac gcttcacg                                                  18

<210> SEQ ID NO 41
<211> LENGTH: 17
<212> TYPE: RNA
<213> ORGANISM: Homo sapiens

<400> SEQUENCE: 41
gugaagcguu ccauauu                                                   17

<210> SEQ ID NO 42
<211> LENGTH: 46
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (46)..(46)
<223> OTHER INFORMATION: n is a, c, g or t
<220> FEATURE:
<221> NAME/KEY: misc_feature
<222> LOCATION: (45)..(45)
<223> OTHER INFORMATION: v is a, c or g

<400> SEQUENCE: 42
gcgagcacag aattaatacg actcactatc ggttttttttt ttttvn                  46

<210> SEQ ID NO 43
<211> LENGTH: 22
<212> TYPE: DNA
<213> ORGANISM: Artificial sequence
<220> FEATURE:
<223> OTHER INFORMATION: Synthetic

<400> SEQUENCE: 43
cgtttttttt ttttccatct tt                                             22

<210> SEQ ID NO 44
<211> LENGTH: 23
<212> TYPE: RNA
<213> ORGANISM: Homo sapiens

<400> SEQUENCE: 44
uagcaccauu ugaaaucagu guu                                            23

<210> SEQ ID NO 45
<211> LENGTH: 81
<212> TYPE: RNA
<213> ORGANISM: Homo sapiens

<400> SEQUENCE: 45
cuucaggaag cugguuucau auggugguuu agauuuaaau agugauuguc uagcaccauu     60
ugaaaucagu guucuugggg g                                              81
```

<210> SEQ ID NO 46
<211> LENGTH: 81
<212> TYPE: RNA
<213> ORGANISM: Homo sapiens

<400> SEQUENCE: 46
cuucuggaag cugguuucac augguggcuu agauuuuucc aucuuuguau cuagcaccau    60
uugaaaucag uguuuuagga g                                             81

<210> SEQ ID NO 47
<211> LENGTH: 22
<212> TYPE: RNA
<213> ORGANISM: Homo sapiens

<400> SEQUENCE: 47
uguaaacauc cuacacucag cu                                            22

<210> SEQ ID NO 48
<211> LENGTH: 88
<212> TYPE: RNA
<213> ORGANISM: Homo sapiens

<400> SEQUENCE: 48
accaaguuuc aguucaugua aacauccuac acucagcugu aauacaugga uuggcuggga    60
gguggauguu uacuucagcu gacuugga                                      88

<210> SEQ ID NO 49
<211> LENGTH: 22
<212> TYPE: RNA
<213> ORGANISM: Homo sapiens

<400> SEQUENCE: 49
uccuucauuc caccggaguc ug                                            22

<210> SEQ ID NO 50
<211> LENGTH: 110
<212> TYPE: RNA
<213> ORGANISM: Homo sapiens

<400> SEQUENCE: 50
aaagauccuc agacaaucca ugugcuucuc uugccuuca uuccaccgga gucugucuca     60
uacccaacca gauuucagug gagugaaguu caggaggcau ggagcugaca             110

<210> SEQ ID NO 51
<211> LENGTH: 28
<212> TYPE: DNA
<213> ORGANISM: Artificial sequence
<220> FEATURE:
<223> OTHER INFORMATION: Synthetic

<400> SEQUENCE: 51
cagtcatttg ggtccttcat tccaccgg                                      28

<210> SEQ ID NO 52
<211> LENGTH: 22
<212> TYPE: DNA
<213> ORGANISM: Artificial sequence
<220> FEATURE:
<223> OTHER INFORMATION: Synthetic

<400> SEQUENCE: 52 cgttttttt ttttcagact cc                                              22

<210> SEQ ID NO 53
<211> LENGTH: 28
<212> TYPE: DNA
<213> ORGANISM: Artificial sequence
<220> FEATURE:
<223> OTHER INFORMATION: Synthetic

<400> SEQUENCE: 53
cagtcatttg ggtttgttcg ttcggctc                                       28

<210> SEQ ID NO 54
<211> LENGTH: 23
<212> TYPE: DNA
<213> ORGANISM: Artificial sequence
<220> FEATURE:
<223> OTHER INFORMATION: Synthetic

<400> SEQUENCE: 54
ccgttttttt ttttcacgc gag                                             23

<210> SEQ ID NO 55
<211> LENGTH: 22
<212> TYPE: RNA
<213> ORGANISM: Homo Sapiens

<400> SEQUENCE: 55
uagcuuauca gacugauguu ga                                             22

<210> SEQ ID NO 56
<211> LENGTH: 28
<212> TYPE: DNA
<213> ORGANISM: Artificial Sequence
<220> FEATURE:
<223> OTHER INFORMATION: Synthetic

<400> SEQUENCE: 56
cagtcatttg ggtagcttat cagactga                                       28

<210> SEQ ID NO 57
<211> LENGTH: 23
<212> TYPE: DNA
<213> ORGANISM: Artificial Sequence
<220> FEATURE:
<223> OTHER INFORMATION: Synthetic

<400> SEQUENCE: 57
ccgttttttt ttttcaaca tca                                             23

<210> SEQ ID NO 58
<211> LENGTH: 21
<212> TYPE: RNA
<213> ORGANISM: Homo Sapiens

<400> SEQUENCE: 58
ugagaugaag cacuguagcu c                                              21

<210> SEQ ID NO 59
<211> LENGTH: 23
<212> TYPE: RNA
<213> ORGANISM: Homo Sapiens

<400> SEQUENCE: 59
agcuacauug ucugcugggu uuc                                            23

```
<210> SEQ ID NO 60
<211> LENGTH: 22
<212> TYPE: RNA
<213> ORGANISM: Homo Sapiens

<400> SEQUENCE: 60
uguaaacauc cccgacugga ag                                              22

<210> SEQ ID NO 61
<211> LENGTH: 22
<212> TYPE: RNA
<213> ORGANISM: Homo Sapiens

<400> SEQUENCE: 61
aacuggcccu caaagucccg cu                                              22

<210> SEQ ID NO 62
<211> LENGTH: 22
<212> TYPE: RNA
<213> ORGANISM: Homo Sapiens

<400> SEQUENCE: 62
ugaaacauac acgggaaacc uc                                              22

<210> SEQ ID NO 63
<211> LENGTH: 22
<212> TYPE: RNA
<213> ORGANISM: Homo Sapiens

<400> SEQUENCE: 63
ugggucuuug cgggcgagau ga                                              22

<210> SEQ ID NO 64
<211> LENGTH: 21
<212> TYPE: RNA
<213> ORGANISM: Homo Sapiens

<400> SEQUENCE: 64
ucagugcaug acagaacuug g                                               21

<210> SEQ ID NO 65
<211> LENGTH: 22
<212> TYPE: RNA
<213> ORGANISM: Homo Sapiens

<400> SEQUENCE: 65
uguaaacauc cucgacugga ag                                              22

<210> SEQ ID NO 66
<211> LENGTH: 22
<212> TYPE: RNA
<213> ORGANISM: Homo Sapiens

<400> SEQUENCE: 66
cugugcgugu gacagcggcu ga                                              22

<210> SEQ ID NO 67
<211> LENGTH: 21
<212> TYPE: RNA
<213> ORGANISM: Homo Sapiens

<400> SEQUENCE: 67
```
cagcagcaca cugugguuug u                                           21

<210> SEQ ID NO 68
<211> LENGTH: 22
<212> TYPE: RNA
<213> ORGANISM: Homo Sapiens

<400> SEQUENCE: 68
cagugcaaug uuaaaagggc au                                          22

<210> SEQ ID NO 69
<211> LENGTH: 22
<212> TYPE: RNA
<213> ORGANISM: Homo Sapiens

<400> SEQUENCE: 69
uccuguacug agcugccccg ag                                          22

<210> SEQ ID NO 70
<211> LENGTH: 22
<212> TYPE: RNA
<213> ORGANISM: Homo Sapiens

<400> SEQUENCE: 70
ucguaccgug aguaauaaug cg                                          22

<210> SEQ ID NO 71
<211> LENGTH: 23
<212> TYPE: RNA
<213> ORGANISM: Homo Sapiens

<400> SEQUENCE: 71
uacccuguag aaccgaauuu gug                                         23

<210> SEQ ID NO 72
<211> LENGTH: 22
<212> TYPE: RNA
<213> ORGANISM: Homo Sapiens

<400> SEQUENCE: 72
aaaccguuac cauuacugag uu                                          22

<210> SEQ ID NO 73
<211> LENGTH: 106
<212> TYPE: RNA
<213> ORGANISM: Homo Sapiens

<400> SEQUENCE: 73
gcgcagcgcc cugucuccca gccugaggug cagugcugca ucucugguca guugggaguc      60
ugagaugaag cacuguagcu caggaagaga gaaguuguuc ugcagc                    106

<210> SEQ ID NO 74
<211> LENGTH: 110
<212> TYPE: RNA
<213> ORGANISM: Homo Sapiens

<400> SEQUENCE: 74
ugaacaucca ggucgggggc augaaccugg cauacaaugu agauuucugu guucguuagg      60
caacagcuac auugucugcu ggguuucagg cuaccuggaa acauguucuc                110

<210> SEQ ID NO 75
<211> LENGTH: 70

<212> TYPE: RNA
<213> ORGANISM: Homo Sapiens

<400> SEQUENCE: 75
guuguuguaa acauccccga cuggaagcug uaagacacag cuaagcuuuc agucagaugu    60
uugcugcuac                                                          70

<210> SEQ ID NO 76
<211> LENGTH: 83
<212> TYPE: RNA
<213> ORGANISM: Homo Sapiens

<400> SEQUENCE: 76
guggucucag aaucgggguu uugagggcga gaugaguuua uguuuauuacc aacuggcccu   60 caaagucccg cuuuuggggu cau                                           83

<210> SEQ ID NO 77
<211> LENGTH: 81
<212> TYPE: RNA
<213> ORGANISM: Homo Sapiens

<400> SEQUENCE: 77
gauacucgaa ggagagguug uccguguugu cuucucuuua uuuaugauga aacauacacg   60
ggaaaccucu uuuuaguau c                                              81

<210> SEQ ID NO 78
<211> LENGTH: 88
<212> TYPE: RNA
<213> ORGANISM: Homo Sapiens

<400> SEQUENCE: 78
cgaggauggg agcugagggc uggucuuug cgggcgagau gagggugucg gaucaacugg    60
ccuacaaagu cccaguucuc ggcccccg                                      88

<210> SEQ ID NO 79
<211> LENGTH: 87
<212> TYPE: RNA
<213> ORGANISM: Homo Sapiens

<400> SEQUENCE: 79 ugucccccc ggcccagguu cugugauaca cuccgacucg ggcucuggag cagucagugc    60
augacagaac uugggcccgg aaggacc                                       87

<210> SEQ ID NO 80
<211> LENGTH: 71
<212> TYPE: RNA
<213> ORGANISM: Homo Sapiens

<400> SEQUENCE: 80
gcgacuguaa acauccucga cuggaagcug ugaagccaca gaugggcuuu cagucggaug   60
uuugcagcug c                                                        71

<210> SEQ ID NO 81
<211> LENGTH: 110
<212> TYPE: RNA
<213> ORGANISM: Homo Sapiens

<400> SEQUENCE: 81
acccggcagu gccuccaggc gcagggcagc cccugcccac cgcacacugc gcugcccag    60

```
acccacugug cgugugacag cggcugaucu gugccugggc agcgcgaccc            110

<210> SEQ ID NO 82
<211> LENGTH: 112
<212> TYPE: RNA
<213> ORGANISM: Homo Sapiens

<400> SEQUENCE: 82
ccaccccggu ccugcucccg ccccagcagc acacugguggu uuguacggca cuguggccac   60
guccaaacca cacuggguug uuagagcgag gguggggag gcaccgccga gg            112

<210> SEQ ID NO 83
<211> LENGTH: 89
<212> TYPE: RNA
<213> ORGANISM: Homo Sapiens

<400> SEQUENCE: 83
ugcugcuggc cagagcucuu uucacauugu gcuacugucu gcaccuguca cuagcagugc   60
aauguuaaaa gggcauuggc cguguagug                                    89

<210> SEQ ID NO 84
<211> LENGTH: 68
<212> TYPE: RNA
<213> ORGANISM: Homo Sapiens

<400> SEQUENCE: 84
gcauccugua cugagcugcc ccgaggcccu ucaugcugcc cagcucgggg cagcucagua   60
caggauac                                                           68

<210> SEQ ID NO 85
<211> LENGTH: 85
<212> TYPE: RNA
<213> ORGANISM: Homo Sapiens

<400> SEQUENCE: 85
cgcuggcgac gggacauuau uacuuuuggu acgcgcugug acacuucaaa cucguaccgu   60
gaguaauaau gcgccgucca cggca                                        85

<210> SEQ ID NO 86
<211> LENGTH: 110
<212> TYPE: RNA
<213> ORGANISM: Homo Sapiens

<400> SEQUENCE: 86
ccagagguug uaacguuguc uauauauacc cuguagaacc gaauuugugu gguauccgua   60
uagucacaga uucgauucua ggggaauaua uggucgaugc aaaaacuuca             110

<210> SEQ ID NO 87
<211> LENGTH: 72
<212> TYPE: RNA
<213> ORGANISM: Homo Sapiens

<400> SEQUENCE: 87
cuugggaaug gcaaggaaac cguuaccauu acugaguuua guaaugguaa ugguucucuu   60
gcuauaccca ga                                                      72
```